(12) United States Patent
Sliwkowski et al.

(10) Patent No.: US 8,163,287 B2
(45) Date of Patent: Apr. 24, 2012

(54) COMBINATION THERAPY OF HER EXPRESSING TUMORS

(75) Inventors: Mark X. Sliwkowski, San Carlos, CA (US); Stephen M. Kelsey, Montara, CA (US)

(73) Assignee: Genentech, Inc., South San Francisco, CA (US)

( * ) Notice: Subject to any disclaimer, the term of this patent is extended or adjusted under 35 U.S.C. 154(b) by 1237 days.

(21) Appl. No.: 11/490,438

(22) Filed: Jul. 19, 2006

(65) Prior Publication Data

US 2007/0020261 A1 Jan. 25, 2007

Related U.S. Application Data

(60) Provisional application No. 60/701,852, filed on Jul. 22, 2005.

(51) Int. Cl.
*A61K 39/395* (2006.01)
*A01N 43/42* (2006.01)
*A01N 43/54* (2006.01)
*C07D 239/72* (2006.01)

(52) U.S. Cl. ............ 424/143.1; 424/130.1; 424/133.1; 424/136.1; 424/141.1; 424/155.1; 424/156.1; 424/174.1

(58) Field of Classification Search ............ 424/130.1, 424/133.1, 136.1, 141.1, 143.1, 155.1, 156.1, 424/174.1
See application file for complete search history.

(56) References Cited

U.S. PATENT DOCUMENTS

| | | | |
|---|---|---|---|
| 5,648,237 A | 7/1997 | Carter | |
| 5,677,171 A | 10/1997 | Hudziak et al. | |
| 5,720,937 A | 2/1998 | Hudziak et al. | |
| 5,720,954 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,777,195 A | 7/1998 | Fienberg et al. | |
| 5,821,337 A | 10/1998 | Carter et al. | |
| 6,015,567 A | 1/2000 | Hudziak et al. | |
| 6,054,297 A | 4/2000 | Carter et al. | |
| 6,127,526 A | 10/2000 | Blank | |
| 6,165,464 A | 12/2000 | Hudziak et al. | |
| 6,267,958 B1 | 7/2001 | Andya et al. | |
| 6,333,169 B1 | 12/2001 | Hudziak et al. | |
| 6,333,398 B1 | 12/2001 | Blank | |
| 6,339,142 B1 | 1/2002 | Basey et al. | |
| 6,387,371 B1 | 5/2002 | Hudziak et al. | |
| 6,399,063 B1 | 6/2002 | Hudziak et al. | |
| 6,407,213 B1 | 6/2002 | Carter et al. | |
| 6,417,335 B1 | 7/2002 | Basey et al. | |
| 6,489,447 B1 | 12/2002 | Basey et al. | |
| 6,573,043 B1 | 6/2003 | Cohen et al. | |
| 6,627,196 B1 | 9/2003 | Baughman et al. | |
| 6,632,979 B2 | 10/2003 | Erickson et al. | |
| 6,639,055 B1 | 10/2003 | Carter et al. | |
| 6,685,940 B2 | 2/2004 | Andya et al. | |
| 6,719,971 B1 | 4/2004 | Carter et al. | |
| 6,797,814 B2 | 9/2004 | Blank | |
| 6,800,738 B1 | 10/2004 | Carter et al. | |
| 6,821,515 B1 | 11/2004 | Cleland et al. | |
| 6,900,221 B1 * | 5/2005 | Norris et al. ............... | 514/266.4 |
| 6,905,830 B2 | 6/2005 | Cohen et al. | |
| 6,949,245 B1 | 9/2005 | Sliwkowski | |
| 6,984,494 B2 | 1/2006 | Ralph | |
| 7,018,809 B1 | 3/2006 | Carter | |
| 7,041,292 B1 | 5/2006 | Sliwkowski | |
| 7,060,268 B2 | 6/2006 | Andya et al. | |
| 7,074,404 B2 | 7/2006 | Basey et al. | |
| 7,097,840 B2 | 8/2006 | Erickson et al. | |
| 7,129,051 B2 | 10/2006 | Cohen et al. | |
| 7,279,287 B2 | 10/2007 | Ralph | |
| 7,371,376 B1 | 5/2008 | Fendly | |
| 7,371,379 B2 | 5/2008 | Baughman et al. | |
| 7,449,184 B2 * | 11/2008 | Allison et al. ............. | 424/138.1 |
| 7,485,302 B2 | 2/2009 | Adams et al. | |
| 7,498,030 B2 | 3/2009 | Adams et al. | |
| 7,501,122 B2 | 3/2009 | Adams et al. | |
| 2001/0014326 A1 | 8/2001 | Andya et al. | |
| 2002/0001587 A1 | 1/2002 | Erickson et al. | |
| 2002/0032317 A1 | 3/2002 | Blank | |
| 2002/0035736 A1 | 3/2002 | Erickson et al. | |
| 2002/0090662 A1 | 7/2002 | Ralph | |
| 2003/0147884 A1 | 8/2003 | Paton et al. | |
| 2003/0152987 A1 | 8/2003 | Cohen et al. | |
| 2003/0202972 A1 | 10/2003 | Andya et al. | |
| 2003/0228663 A1 | 12/2003 | Lowman et al. | |
| 2004/0037823 A9 | 2/2004 | Paton et al. | |
| 2004/0082047 A1 | 4/2004 | Emery et al. | |
| 2004/0106161 A1 | 6/2004 | Bossenmaier et al. | |

(Continued)

FOREIGN PATENT DOCUMENTS

WO    WO 98/17797    4/1998

(Continued)

OTHER PUBLICATIONS

Baselga, J. et al., Oncology, 63(supple 1): 6-16, 2002.*
Kim, T.E. et al, Current Opinion in Investigational Drugs, 3(9): 1385-1395, 2002.*
Freiss, T et al., "Combination Treatment with Erlotinib and Pertzumab Against Human Tumor Xenografts is Superior to Monotherapy" clinical Cancer Research, The American Association for Cancer Research, Us, vol. 11, No. 14, (Jul. 15, 2005), pp. 5300-539, XP002393212 ISSN: 1078-0432.
Mass, R. D., "The Her Receptor Family: A Rich Target for Therapeutic Development" International Journal of Radiation Oncology Biology Physics, Pergamon Press, Us., vol. 58, No. 3 (Mar. 1, 2004), pp. 932-940, XP008060823 ISSN:0360-3016.
Agus, et al., "Clinical activity in a phase 1 trial of HER-2 targeted rhuMab 2C4 (pertuzumab) in patients with advanced solid malignancies (AST)", Proceedings of the AACR, Abstract No. 771, vol. 22, p. 192, (2003).

(Continued)

*Primary Examiner* — Alana Harris Dent
*Assistant Examiner* — Anne Holleran
(74) *Attorney, Agent, or Firm* — Arnold & Porter LLP; Wendy Lee; Ginger R. Dreger

(57) ABSTRACT

The invention relates to tumors expressing HER2 and EGFR, using HER2-dimerization inhibitors (HDIs) and EGFR inhibitors.

45 Claims, 17 Drawing Sheets

U.S. PATENT DOCUMENTS

| | | |
|---|---|---|
| 2004/0258685 A1 | 12/2004 | Brunetta et al. |
| 2005/0002928 A1 | 1/2005 | Hellmann |
| 2005/0038231 A1 | 2/2005 | Fahrner et al. |
| 2005/0063972 A1 | 3/2005 | Basey et al. |
| 2005/0100944 A1 | 5/2005 | Cohen et al. |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2005/0244929 A1 | 11/2005 | Carter |
| 2005/0276812 A1 | 12/2005 | Ebens et al. |
| 2006/0013819 A1 | 1/2006 | Kelsey et al. |
| 2006/0018898 A1 | 1/2006 | Waldmann et al. |
| 2006/0034840 A1 | 2/2006 | Agus |
| 2006/0034842 A1 | 2/2006 | Adams et al. |
| 2006/0046270 A1 | 3/2006 | Ralph |
| 2006/0067930 A1 | 3/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |
| 2006/0090662 A1 | 5/2006 | Biggs et al. |
| 2006/0099201 A1 | 5/2006 | Andya et al. |
| 2006/0121044 A1 | 6/2006 | Amler et al. |
| 2006/0165702 A1 | 7/2006 | Allison et al. |
| 2006/0182739 A1 | 8/2006 | Basey et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0228745 A1 | 10/2006 | Mass |
| 2006/0275305 A1 | 12/2006 | Bryant |
| 2006/0275306 A1 | 12/2006 | Andya et al. |
| 2007/0009976 A1 | 1/2007 | Lenz et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0166753 A1 | 7/2007 | Mass |
| 2007/0184055 A1 | 8/2007 | Sliwkowski |
| 2007/0202516 A1 | 8/2007 | Mass |
| 2007/0224203 A1 | 9/2007 | Friess et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0102069 A1 | 5/2008 | Friess et al. |
| 2008/0108096 A1 | 5/2008 | Ralph |
| 2008/0112957 A1 | 5/2008 | Fendly et al. |
| 2008/0112958 A1 | 5/2008 | Mass |
| 2008/0160026 A1 | 7/2008 | Ashkenazi et al. |
| 2008/0171040 A1 | 7/2008 | Ebens, et al. |
| 2008/0187533 A1 | 8/2008 | Hellmann |
| 2008/0226659 A1 | 9/2008 | Erickson et al. |
| 2008/0241146 A1 | 10/2008 | Ashkenazi et al. |
| 2008/0317753 A1 | 12/2008 | Amler et al. |

FOREIGN PATENT DOCUMENTS

| | | |
|---|---|---|
| WO | WO 99/31140 | 6/1999 |
| WO | WO 99/48527 | 9/1999 |
| WO | WO 00/69467 | 11/2000 |
| WO | WO 01/00238 | 1/2001 |
| WO | WO 01/00244 | 1/2001 |
| WO | WO 01/00245 | 1/2001 |
| WO | WO 01/15730 | 3/2001 |
| WO | WO 01/89566 | 11/2001 |
| WO | WO 03/087131 | 10/2003 |
| WO | WO 2004/008099 A2 | 1/2004 |
| WO | WO 2004/24866 | 3/2004 |
| WO | WO 2004/048525 | 6/2004 |
| WO | WO 2005/16968 | 2/2005 |
| WO | WO 2005/099756 | 10/2005 |
| WO | WO 2006/007398 A1 | 1/2006 |
| WO | WO 2006/033700 A2 | 3/2006 |
| WO | WO 2006/044908 A2 | 4/2006 |
| WO | WO 2006/063042 A2 | 6/2006 |
| WO | WO 2006/078307 | 7/2006 |
| WO | WO 2006/078307 A1 | 7/2006 |
| WO | WO 2006/091693 | 8/2006 |
| WO | WO 2006/096861 | 9/2006 |
| WO | WO 2007/003420 | 1/2007 |
| WO | WO 2007/013950 | 2/2007 |
| WO | WO 2007/019899 | 2/2007 |
| WO | WO 2007/107329 | 9/2007 |
| WO | WO 2007/145862 | 12/2007 |
| WO | WO 2008/031531 | 3/2008 |

OTHER PUBLICATIONS

Agus, et al., "Clinical activity in a phase 1 trial of HER-2 targeted rhuMab 2C4 (pertuzumab) in patients with advanced solid malignancies (AST)", pp. 1-32, (2003).

Agus, et al., "Efficacy and safety of single agent pertuzumab (rhuMAb 2C4), a HER dimerization inhibitor, in hormone refractory prostate cancer after failure of taxane-based therapy", Journal of CO, Abstract 4624, 23(16s): 408s, (2005).

Agus, et al, "Phase 1 clinical study of pertuzumab, a novel HER dimerzation inhibitor, in patients with advanced cancer", Journal of CO, 23 (11): 2534-2543, (2005).

Agus, et al., "Efficacy and safety of single agent pertuzumab (rhuMAb 2C4), a HER dimerization inhibitor, in hormone refractory prostate cancer after failure of taxane-based therapy", poster 4624 from $1^{st}$ annual meeting of the ASCO, (2005).

Allison, et al., "Pharmacokinetics (PK) of pertuzumab (rhuMAb 2C4) in phase II studies of ovarian, breast, prostate and lung cancers", poster 2532 presented at the 2005 ASCO meeting, (2005).

Allison, et al., "Pharmacokinetics (PK) of pertuzumab (rhuMAb 2C4) in phase 11 studies of ovarian, breast, prostate and lung cancers", Journal of CO, 23(16s): 2532, (2005).

Allison, et al., "Pharmacokinetics of HER-2 targeted rhuMAb 2C4 (pertuzumab) in patients with advanced solid malignancies: Phase la results", meeting proceedings of the ASCO, Absrtact 790, 22: 197, (2003).

Amler, et al., "Identification of a predictive expression pattern for phosphorylated HER2 as a potential diagnostic marker for pertuzumab (OMNITARG) activity in ovarian cancer", poster 4497 presented at the Apr. 2006 AACR, (2006).

Arpino, et al, "Complete disappearance of ER+/HER2+ breast cancer xenografts with the combination of gefitinib, and pertuzumab to block HER2 cross-talk with ER and restore tamoxifen inhibitor", Breast Cancer Research and Treatment, Abstract 23, 88 (Suppl. I ): SI5, (2004).

Bossenmaier, et al, "Presence of HER2/HER3 heterodimers predicts antitumor effects of pertuzumab (OMNITARG) in different human xenograft models", Proc. AACR, Abstract 5342, 45:1232, (2004).

Cortes, et al., "Open label, randomized, pahse 11 study of pertuzumab (OMNITARGT) in patients with metastatic breast cancer (MBC) with low expression of HER2", poster 3068 from the $41^{st}$ ASCO, (2005).

Cortes, et al., "Open label, randomized, pahse II study of pertuzumab (P) in patients (pts) with metastatic breast cancer (MBC) with low expression of HER2", JCO, Abstract 3068 from the $41^{st}$ ASCO, 23(16s):208s, (2005).

De bobno et al., "An open label, phase II, multicenter study to evaluate the efficacy and safety of pertuzumab I chemotherapy-naïve patients with hormone-refractory prostate cancer (HRPC)", poster 4609 from ASCO, (2005).

Friess, et al., "Combination treatment with erlotinib and pertuzumab against human tumor xenografts is superior to monotherapy", CCR, 11(15): 5300-5309, (2005).

Gordon, et al., "Clinical activity of pertuzumab (rhuMAb 2C4), a HER dimerzation inhibitor, in advanced ovarian cancer: potential predictive relationship with tumor HER2 activation status", JCO, 24(6): 4324-4332, (2006).

Gordon, et al., "Clinical activity of pertuzumab (rhuMAb 2C4), in advanced, refractory or recurrent ovarian cancer (OC), and the role of HER2 activation status", JCO, Abstract 5051, 23(16s): 467s, (2005).

Gordon, et al., "Clinical activity of single agent pertuzumab (rhuMab 2C4), a GER dimerzation inhibitor, in advanced ovarian cancer (OC): potential predictive relationship with tumor HER2 activation status", EJC, Abstract 903, 3(2): 259-260, (2005).

Hasmann, et al., "Pertuzumab (Omnitarg) potentiates antitumor effects on NSCLS xenografts without increasing toxicity when combined with cytotoxic chemotherapy agents", AACR, Abstract B213, 9(16), (2003).

Herbst, et al, "Efficacy and safety of single agent pertuzumab (rhuMAb 2C4), a HER dimerzation inhibitor, in non-small cell lung cancer (NSCLC) patients after prior chemotherapy", Abstract 0-187, 49: S62, (2005).

Makhija et al., "Results from a Ph II randomized, placebo-controlled, double—blind trial suggest improved PFS with the addition of pertuzumab to gemcitabine in patients with platinum-resistant ovarian, fallopian tube, or primary peritoneal cancer", ASCO, pp. 1-28, (2007).

Makhija et al., "Results from a Ph II randomized, placebo-controlled, double—blind trial suggest improved PFS with the addition of pertuzumab to gemcitabine in patients with platinum-resistant ovarian, fallopian tube, or primary peritoneal cancer", J. Clin. Oncol., Absrtact 5507, 25(18s): 5507, (2007).

Malik, et al., "Dose-response studies of recombinant humanized monoclonal antibody 2C4 (pertuzumab) in tumor xenograft models" poster 773, (2003).

Nahta, et al., "The HER-2 targeting antibodies trastuzumab and pertuzumab synergistically inhibit the survival of breast cancer cells", Cancer research, 64 (7): 2343-2346, (2004).

Ng, et al., "Rationale for fixed dosing of pertuzumab by population pharmacokinetic (POP PK) modeling", Clinical Pharmacology & Therapeutics, Abstract PI-97, 77(2): P33, (2005).

Valle, et al., "A Phase lb study of pertuzumab (P), a recombinant humanized antibody to HER2, and capecitabine (C) in patients with advanced solid tumors", EJC, Abstract 287, 2(8): 88, (2004).

Clinical Trial Search, A Study of pertuzumab in combination with tarceva (erlotinib) in patients with locally advanced or metastatic non-small cell lung cancer, (2006).

ClinicalTrials.gov, Safety and effect of pertuzumab in patients with advanced non small cell lung cancer, which has progressed after prior chemotherapy, pp. 1-4, (2003).

ClinicalTrials.gov, Pertuzumab, cetuximab and irinotecan in treating patients with previously treated locally advanced or metastatic colorectal cancer, pp. 1-6, (2007).

* cited by examiner

VARIABLE LIGHT

```
                  10          20              30              40
2C4      DTVMTQSHKIMSTSVGDRVSITC  [KASQDVSIGVA]  WYQQRP
           **   ****  *           *                 *
574      DIQMTQSPSSLSASVGDRVTITC  [KASQDVSIGVA]  WYQQKP
                                       *   **  ***
hum κI   DIQMTQSPSSLSASVGDRVTITC  [RASQSISNYLA]  WYQQKP 50              60          70              80
2C4      GQSPKLLIY  [SASYRYT]  GVPDRFTGSGSGTDFTFTISSVQA
           **                       *         *        *  * *
574      GKAPKLLIY  [SASYRYT]  GVPSRFSGSGSGTDFTLTISSLQP
                     * *****
hum κI   GKAPKLLIY  [AASSLES]  GVPSRFSGSGSGTDFTLTISSLQP 90          100
2C4      EDLAVYYC  [QQYYIYPYT]  FGGGTKLEIK  (SEQ ID NO:1)
           * *                    *    *
574      EDFATYYC  [QQYYIYPYT]  FGQGTKVEIK  (SEQ ID NO:3)
                     *** *
hum κI   EDFATYYC  [QQYNSLPWT]  FGQGTKVEIK  (SEQ ID NO:5)
```

FIG. 2A

VARIABLE HEAVY

```
                  10          20              30              40
2C4      EVQLQQSGPELVKPGTSVKISCKAS  [GFTFTDYTMD]  WVKQS
           **   **   *   *  ***  *                   * *
574      EVQLVESGGGLVQPGGSLRLSCAAS  [GFTFTDYTMD]  WVRQA
                                       ** *  *
hum III  EVQLVESGGGLVQPGGSLRLSCAAS  [GFTFSSYAMS]  WVRQA 50    a         60              70              80
2C4      HGKSLEWIG  [DVNPNSGGSIYNQRFKG]  KASLTVDRSSRIVYM
          *  *  **                         *** *    ****  *
574      PGKGLEWVA  [DVNPNSGGSIYNQRFKG]  RFTLSVDRSKNTLYL
                     ****** *** ****         * * *
hum III  PGKGLEWVA  [VISGDGGSTYYADSVKG]  RFTISRDNSKNTLYL abc         90        100ab          110
2C4      ELRSLTFEDTAVYYCAR  [NLGPSFYFDY]  WGQGTTLTVSS  (SEQ ID NO:2)
           ***   **                                **
574      QMNSLRAEDTAVYYCAR  [NLGPSFYFDY]  WGQGTLVTVSS  (SEQ ID NO:4)
                                ********
hum III  QMNSLRAEDTAVYYCAR  [GRVGYSLYDY]  WGQGTLVTVSS  (SEQ ID NO:6)
```

FIG. 2B

Amino Acid Sequence for Pertuzumab Light Chain

```
1         10        20        30        40        50        60
|         |         |         |         |         |         |
DIQMTQSPSSLSASVGDRVTITCKASQDVSIGVAWYQQKPGKAPKLLIYSASYRYTGVPS 70        80        90        100       110       120
          |         |         |         |         |         |
RFSGSGSGTDFTLTISSLQPEDFATYYCQQYYIYPYTFGQGTKVEIKRTVAAPSVFIFPP 130       140       150       160       170       180
          |         |         |         |         |         |
SDEQLKSGTASVVCLLNNFYPREAKVQWKVDNALQSGNSQESVTEQDSKDSTYSLSSTLT 190       200       210
          |         |         |
LSKADYEKHKVYACEVTHQGLSSPVTKSFNRGEC
```

FIG. 3A

Amino Acid Sequence for Pertuzumab Heavy Chain

```
  1         10        20        30        40        50        60
  |         |         |         |         |         |         |
EVQLVESGGGLVQPGGSLRLSCAASGFTFTDYTMDWVRQAPGKGLEWVADVNPNSGGSIY 70        80        90       100       110       120
            |         |         |         |         |         |
NQRFKGRFTLSVDRSKNTLYLQMNSLRAEDTAVYYCARNLGPSFYFDYWGQGTLVTVSSA 130       140       150       160       170       180
            |         |         |         |         |         |
STKGPSVFPLAPSSKSTSGGTAALGCLVKDYFPEPVTVSWNSGALTSGVHTFPAVLQSSG 190       200       210       220       230       240
            |         |         |         |         |         |
LYSLSSVVTVPSSSLGTQTYICNVNHKPSNTKVDKKVEPKSCDKTHTCPPCPAPELLGGP 250       260       270       280       290       300
            |         |         |         |         |        *|
SVFLFPPKPKDTLMISRTPEVTCVVVDVSHEDPEVKFNWYVDGVEVHNAKTKPREEQYNS 310       320       330       340       350       360
            |         |         |         |         |         |
TYRVVSVLTVLHQDWLNGKEYKCKVSNKALPAPIEKTISKAKGQPREPQVYTLPPSREEM 370       380       390       400       410       420
            |         |         |         |         |         |
TKNQVSLTCLVKGFYPSDIAVEWESNGQPENNYKTTPPVLDSDGSFFLYSKLTVDKSRWQ 430       440       448
            |         |         |
QGNVFSCSVMHEALHNHYTQKSLSLSPG
```

FIG. 3B

```
1                          15            30                45
VHSDIQMTQSPSSLSASVGDRVTITCKASQDVSIGVAWYQQKPGK 46                          60            75                90
APKLLIYSASYRYTGVPSRFSGSGSGTDFTLTISSLQPEDFATYY 91                          105           120              135
CQQYYIYPYTFGQGTKVEIKRTVAAPSVFIFPPSDEQLKSGTASV 136                         150           165              180
VCLLNNFYPREAKVQWKVDNALQSGNSQESVTEQDSKDSTYSLSS 181                         195           210      217
TLTLSKADYEKHKVYACEVTHQGLSSPVTKSFNRGEC
```

LIGHT CHAIN

```
1                          15                         30                         45
DIQMTQSPSSLSASVGDRVTITCRASQDVNTAVAWYQQKPGKAPK 46                         60                         75                         90
LLIYSASFLYSGVPSRFSGSRSGTDFTLTISSLQPEDFATYYCQQ 91                         105                        120                        135
HYTTPPTFGQGTKVEIKRTVAAPSVFIFPPSDEQLKSGTASVVCL 136                        150                        165                        180
LNNFYPREAKVQWKVDNALQSGNSQESVTEQDSKDSTYSLSSTLT 181                        195                        210   214
LSKADYEKHKVYACEVTHQGLSSPVTKSFNRGEC
```

(SEQ ID NO: 1)

FIG. 6A

HEAVY CHAIN

```
1                        15                        30                        45
E V Q L V E S G G G L V Q P G G S L R L S C A A S G F N I K D T Y I H W V R Q A P G K G L 46                       60                        75                        90
E W V A R I Y P T N G Y T R Y A D S V K G R F T I S A D T S K N T A Y L Q M N S L R A E D 91                       105                       120                       135
T A V Y Y C S R W G G D G F Y A M D Y W G Q G T L V T V S S A S T K G P S V F P L A P S S 136                      150                       165                       180
K S T S G G T A A L G C L V K D Y F P E P V T V S W N S G A L T S G V H T F P A V L Q S S 181                      195                       210                       225
G L Y S L S S V V T V P S S S L G T Q T Y I C N V N H K P S N T K V D K K V E P K S C D K 226                      240                       255                       270
T H T C P P C P A P E L L G G P S V F L F P P K P K D T L M I S R T P E V T C V V V D V S 271                      285                       300                       315
H E D P E V K F N W Y V D G V E V H N A K T K P R E E Q Y N S T Y R V V S V L T V L H Q D 316                      330                       345                       360
W L N G K E Y K C K V S N K A L P A P I E K T I S K A K G Q P R E P Q V Y T L P P S R E E 361                      375                       390                       405
M T K N Q V S L T C L V K G F Y P S D I A V E W E S N G Q P E N N Y K T T P P V L D S D G 406                      420                       435                       449
S F F L Y S K L T V D K S R W Q Q G N V F S C S V M H E A L H N H Y T Q K S L S L S P G
                                                                          (SEQ ID NO: 2)
```

FIG. 6B

| Xenograft model | Tumor origin | TCR Omnitarg | TCR Tarceva |
|---|---|---|---|
| | lung ca | 0.29 | 0.71 |
| | lung ca | 0.39 | 0.59 |
| | lung ca | 0.45 | 0.36 |
| | lung ca | 0.46 | 0.86 |
| | lung ca | 0.59 | 0.52 |
| | lung ca | 0.62 | 0.53 |
| | lung ca | 0.7 | 0.62 |
| | lung ca | 0.7 | 0.59 |
| | lung ca | 0.79 | 0.61 |
| | lung ca | 0.86 | 0.53 |
| | lung ca | 0.87 | 0.02 |
| | lung ca | 0.92 | 0.45 |
| | lung ca | 0.93 | 0.32 |
| | lung ca | 1 | 0.41 |
| | lung ca | 1 | 0.9 |
| | lung ca | 1 | 0.75 |
| | colon ca | 0.56 | 0.15 |
| KPL-4 | breast ca | 0.51 | 0.52 |
| Calu-3 | lung ca | 0.18 | 0.21 |
| NCI-H322M | lung ca | 1.02 | 0.08 |
| NCI-H441 (KAM) | lung ca | 0.72 | 0.57 |
| NCI-H522 | lung ca | 0.25 | 0.2 |
| QG56 | lung ca | 0.41 | 0.46 |
| IGROV-1 | ovarian ca | 0.46 | 0.23 |
| SKOV-3 | ovarian ca | 0.99 | 0.91 |
| OVCAR-5 | ovarian ca | 0.73 | 0.49 |

- Oncotest models

COMBINATION THERAPY OF HER EXPRESSING TUMORS

This is a non-provisional application filed under 37 C.F.R. 1.53(b), claiming priority under U.S.C. Section 119(e) to Provisional Application Ser. No. 60/701,852, filed on Jul. 22, 2005, which application is fully incorporated herein.

FIELD OF THE INVENTION

The present invention relates to the treatment of HER expressing tumors. In particular, the invention relates to the treatment of tumors expressing HER2 and EGFR using HER dimerization inhibitors (HDIs) and EGFR inhibitors. The invention further concerns the selection of patients for treatment with various types of HER inhibitors, such as HER antibodies, or their combinations, and the treatment of the patients selected.

BACKGROUND OF THE INVENTION

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR (ErbB1, HER1), encoded by the erbB1 gene, is a member of the type 1 tyrosine kinase family of growth factor receptors, which play critical roles in cellular growth, differentiation, and survival. Activation of these receptors typically occurs via specific ligand binding, resulting in hetero- or homodimerization between receptor family members, with subsequent autophosphorylation of the tyrosine kinase domain. This activation triggers a cascade of intracellular signaling pathways involved in both cellular proliferation (the ras/raf/MAP kinase pathway) and survival (the PI3 kinase/Akt pathway).

EGFR has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn *Pharmac. Ther.* 64:127-154 (1994). A number of human malignancies are associated with aberrant or overexpression of EGFR and/or overexpression of its specific ligands e.g. transforming growth factor α (Gullick, Br Med Bull 1991; 47:87-98; Modijtahedi and Dean, Int J Oncol 1994, 4:277-96; Salomon et al., Crit Rev Oncol Hematol 1995; 19:183-232). EGFR overexpression has been associated with an adverse prognosis in a number of human cancers, including NSCLC. In some instances, overexpression of tumor EGFR has been correlated with both chemoresistance and a poor prognosis (Lei et al., Anticancer Res 1999; 19:221-8; Veale et al., *Br J Cancer* 1993; 68:162-5). Monoclonal antibodies directed against the EGFR or its ligands, TGF-α and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995). Epidermal growth factor (EGF) regulates cell proliferation and differentiation by binding to the extracellular region of EGFR, comprising domains I-IV. This binding results in dimerization of the receptor tyrosine kinase. Study of the crystal structure of a 2:2 complex of human EGF and the EGFR extracellular region has shown that EGFR domains I-III are arranged in a C shape, and EGF is docked between domains I and III. The 1:1 EGF/EGFR complex dimerizes through a direct receptor-receptor interaction, in which a protruding beta-hairpin arm of each domain II holds the body of the other. See, Ogiso et al., *Cell* 110(6):775-87 (2002). In an unactivated state, EGFR is in an autoinhibited configuration, where the dimerization interface is completely occluded by intramolecular interactions. To activate the receptor, EGF binding must promote a large domain rearrangement that exposes this dimerization interface (Ferguson et al., *Mol. Cell.* 11(2):507-17 (2003)).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science,* 235:177-182 (1987); Slamon et al., *Science,* 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765-767 (1986); Fukushige et al., *Mol Cell Biol.,* 6:955-958 (1986); Guerin et al., *Oncogene Res.,* 3:21-31 (1988); Cohen et al., *Oncogene,* 4:81-88 (1989); Yonemura et al., *Cancer Res.,* 51:1034 (1991); Borst et al., *Gynecol. Oncol.,* 38:364 (1990); Weiner et al., *Cancer Res.,* 50:421-425 (1990); Kern et al., *Cancer Res.,* 50:5184 (1990); Park et al., *Cancer Res.,* 49:6605 (1989); Zhau et al., *Mol. Carcinog.,* 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human HER2 protein products have been described.

Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580(1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al. *PNAS (USA)* 86:9193-9197 (1989)) and HER4 (EP Pat Appln No 599,274; Plowman et al., *Proc. Natl. Acad. Sci. USA*, 90:1746-1750 (1993); and Plowman et al., *Nature*, 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science*, 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et al *Nature* 387:512-516 (1997)); neuregulin-3 which binds HER4 (Zhang et al. *PNAS (USA)* 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20): 14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

Patent publications related to HER antibodies include: U.S. Pat. No. 5,677,171, U.S. Pat. No. 5,720,937, U.S. Pat. No. 5,720,954, U.S. Pat. No. 5,725,856, U.S. Pat. No. 5,770,195, U.S. Pat. No. 5,772,997, U.S. Pat. No. 6,165,464, U.S. Pat. No. 6,387,371, U.S. Pat. No. 6,399,063, US2002/0192211A1, U.S. Pat. No. 6,015,567, U.S. Pat. No. 6,333,169, U.S. Pat. No. 4,968,603, U.S. Pat. No. 5,821,337, U.S. Pat. No. 6,054,297, U.S. Pat. No. 6,407,213, U.S. Pat. No. 6,719,971, U.S. Pat. No. 6,800,738, US2004/0236078A1, U.S. Pat. No. 5,648,237, U.S. Pat. No. 6,267,958, U.S. Pat. No. 6,685,940, U.S. Pat. No. 6,821,515, WO98/17797, U.S. Pat. No. 6,127,526, U.S. Pat. No. 6,333,398, U.S. Pat. No. 6,797,814, U.S. Pat. No. 6,339,142, U.S. Pat. No. 6,417,335, U.S. Pat. No. 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,196B1, U.S. Pat. No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. No. 5,985,553, U.S. Pat. No. 5,747,261, U.S. Pat. No. 4,935,341, U.S. Pat. No. 5,401,638, U.S. Pat. No. 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. No. 5,571,894, U.S. Pat. No. 5,939,531, EP 502,812 B1, WO 93/03741, EP 554,441 B1, EP 656,367 A1, U.S. Pat. No. 5,288,477, U.S. Pat. No. 5,514,554, U.S. Pat. No. 5,587,458, WO 93/12220, WO 93/16185, U.S. Pat. No. 5,877,305, WO 93/21319, WO 93/21232, U.S. Pat. No. 5,856,089, WO 94/22478, U.S. Pat. No. 5,910,486, U.S. Pat. No. 6,028,059, WO 96/07321, U.S. Pat. No. 5,804,396, U.S. Pat. No. 5,846,749, EP 711,565, WO 96/16673, U.S. Pat. No. 5,783,404, U.S. Pat. No. 5,977,322, U.S. Pat. No. 6,512,097, WO 97/00271, U.S. Pat. No. 6,270,765, U.S. Pat. No. 6,395,272, U.S. Pat. No. 5,837,243, WO 96/40789, U.S. Pat. No. 5,783,186, U.S. Pat. No. 6,458,356, WO 97/20858, WO 97/38731, U.S. Pat. No. 6,214,388, U.S. Pat. No. 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. No. 5,705,157, U.S. Pat. No. 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467.

U.S. Application Publication No. 2005010 (published May 12, 2005) and its PCT counterpart, WO 20054432, concern method for treating cancer, including lung cancer, bone cancer and ovarian cancer, with a combination of an ErbB2 ligand and an ErbB antibody.

U.S. Application Publication No. 20050119288 (published Jun. 2, 2005) and its PCT counterpart, WO 200516347, are directed to a method for treating overexpression of the erbB2 receptor by administering a therapeutically effective amount of a first inhibitor of the erbB2 receptor; and subsequently, after an interval comprising less than 24 hours, from one to six therapeutically effective amounts of a second inhibitor of the erbB2 receptor.

WO 2006026313, published Mar. 9, 2006, concerns method for treating cancer by administering 4-quinazolinamines, which are dual inhibitors of EGFR and ErbB2, in combination with at least one other ErbB family inhibitor.

SUMMARY OF THE INVENTION

In one aspect, the invention relates to the treatment of tumor comprising administering to a human subject with a tumor expressing EGFR and HER2, an effective amount of a HER2-dimerization inhibitor and an EGFR inhibitor, wherein the subject's tumor does not show a complete response to treatment with the HER2 dimerization inhibitor or the EGFR inhibitor when administered as a single agent.

In one embodiment, the tumor shows a partial response to treatment with the EGFR inhibitor administered as a single agent.

In another embodiment, the tumor shows a partial response to treatment with the HER2-dimerization inhibitor administered as a single agent.

In yet another embodiment, the tumor shows a partial response to both the EGFR inhibitor and the HER2-dimerization inhibitor when they are administered alone.

In a further embodiment, the tumor treated additionally expresses HER3.

In a still further embodiment, the tumor is refractory to chemotherapy and/or radiation therapy.

In an additional embodiment, the tumor displays HER2 receptor overexpression or amplification.

In an alternative embodiment, the tumor does not display HER2 receptor overexpression or amplification.

The tumor may, for example, be selected from the group consisting of carcinoma, lymphoma, blastoma, sarcoma, neuroendocrine tumors, mesothelioma, schwannoma, meningioma, adenocarcinoma, melanoma, leukemia, and lymphoid malignancies.

In a more specific embodiment, the tumor may be selected from the group consisting of lung cancer, hepatocellular cancer, gastric or stomach cancer, pancreatic cancer, glioblastoma, cervical cancer, ovarian cancer, liver cancer, bladder cancer, hepatoma, breast cancer, colon cancer, rectal cancer, colorectal cancer, endometrial and uterine carcinoma, salivary gland carcinoma, kidney cancer, prostate cancer, vulval cancer, thyroid cancer, hepatic carcinoma, anal carcinoma, penile carcinoma, testicular cancer, esophagael cancer, tumors of the biliary tract, and head and neck cancer.

In a further embodiment, the tumor is lung cancer, such as, for example, small-cell lung cancer (SCLC), non-small cell lung cancer (NSCLC), adenocarcinoma of the lung, or squamous carcinoma of the lung.

In a still further embodiment, the tumor is pancreatic cancer.

In another embodiment, the tumor is colon cancer.

In a different embodiment, the tumor is metastatic tumor.

In yet another embodiment, the HER2 dimerization inhibitor is a HER2 antibody, such as, for example, an antibody which binds to domain II of HER2 extracellular domain (SEQ ID NO: 2), or to a junction between domains I, II and III (SEQ ID NOs: 1, 2 and 3) of HER2 extracellular domain.

In a particular embodiment, the HER2 antibody is a humanized 2C4 antibody.

In another embodiment, the HER2 antibody comprises at least one sequence selected from the variable light chain sequences of SEQ ID NOs: 5 and 7, the variable heavy chain sequences of SEQ ID NOs: 6 and 8, the variable region sequences from within the pertuzumab light and heavy chain sequences of SEQ ID NOS: 11 and 12, and the variable region sequences from within the variant pertuzumab light and heavy chain sequences of SEQ ID NOs: 13 and 14, respectively.

In a preferred embodiment, the HER2 antibody is rhuMAb 2C4 (pertuzumab).

The EGFR inhibitor may, for example, be an EGFR antibody.

In one embodiment, the EGFR inhibitor blocks the formation of EGFR-EGFR homodimers but not the formation of EGFR-HER2 heterodimers.

In another embodiment, the EGFR inhibitor is a compound of formula I;

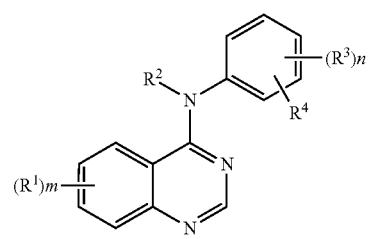

I wherein:
X is halo or hydroxy;
m is 1, 2, or 3;
each $R^1$ is independently selected from the group consisting of hydrogen, halo, hydroxy, hydroxyamino, carboxy, nitro, guanidino, ureido, cyano, trifluoromethyl, and —($C_1$-$C_4$ alkylene)-W-(phenyl) wherein W is a single bond, O, S or NH;
or each $R^1$ is independently selected from $R^9$ and $C_1$-$C_4$ alkyl substituted by cyano, wherein $R^9$ is selected from the group consisting of $R^5$, —$OR^6$, —$NR^6R^6$, —$C(O)R^7$, —$NHOR^5$, —OC(O)R⁶, cyano, A and —YR⁵; R⁵ is $C_1$-$C_4$ alkyl; R⁶ is independently hydrogen or R⁵; R⁷ is R⁵, —OR⁶ or —NR⁶R⁶; A is selected from piperidino, morpholino, pyrrolidino, 4-R⁶-piperazin-1-yl, imidazol-1-yl, 4-pyridon-1-yl, —($C_1$-$C_4$ alkylene)(CO2H), phenoxy, phenyl, phenylsulfanyl, $C_2$-$C_4$ alkenyl, and —($C_1$-$C_4$ alkylene)C(O)NR⁶R⁶; and Y is S, SO, or $SO_2$; wherein the alkyl moieties in R⁵, —OR⁶ and —NR⁶R⁶ are optionally substituted by one to three halo substituents and the alkyl moieties in R⁵, OR⁶ and —NR⁶R⁶ are optionally substituted by 1 or 2 R⁹ groups, and wherein the alkyl moieties of said optional substituents are optionally substituted by halo or R⁹, with the proviso that two heteroatoms are not attached to the same carbon atom;

or each R¹ is independently selected from —NHSO₂R⁵, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and R¹⁰—($C_2$-$C_4$)-alkanoylamino wherein R¹⁰ is selected from halo, —OR⁶, $C_2$-$C_4$ alkanoyloxy, —C(O)R⁷, and —NR⁶R⁶; and wherein said —NHSO₂R⁵, phthalimido-($C_1$-$C_4$-alkylsulfonylamino, benzamido, benzenesulfonylamino, 3-phenylureido, 2-oxopyrrolidin-1-yl, 2,5-dioxopyrrolidin-1-yl, and R¹⁰—($C_2$-$C_4$)-alkanoylamino R¹ groups are optionally substituted by 1 or 2 substituents independently selected from halo, $C_1$-$C_4$ alkyl, cyano, methanesulfonyl and $C_1$-$C_4$ alkoxy;

or two R¹ groups are taken together with the carbons to which they are attached to form a 5-8 membered ring that includes 1 or 2 heteroatoms selected from O, S and N;

R² is hydrogen or $C_1$-$C_6$ alkyl optionally substituted by 1 to 3 substituents independently selected from halo, $C_1$-$C_4$ alkoxy, —NR⁶R⁶, and —SO₂R⁵;

n is 1 or 2 and each R³ is independently selected from hydrogen, halo, hydroxy, $C_1$-$C_6$ alkyl, —NR⁶R⁶, and $C_1$-$C_4$ alkoxy, wherein the alkyl moieties of said R³ groups are optionally substituted by 1 to 3 substituents independently selected from halo, $C_1$-$C_4$ alkoxy, —NR⁶R⁶, and —SO₂R; and, R⁴ is azido or -(ethynyl)-R¹¹ wherein R¹¹ is hydrogen or $C_1$-$C_6$ alkyl optionally substituted by hydroxy, —OR⁶, or —NR⁶R⁶.

In another particular embodiment, the EGFR inhibitor is a compound of formula I selected from the group consisting of:
(6,7-dimethoxyquinazolin-4-yl)-(3-ethynylphenyl)-amine; (6,7-dimethoxyquinazolin-4-yl)-[3-(3'-hydroxypropyn-1-yl)phenyl]-amine; [3-(2'-(aminomethyl)-ethynyl]phenyl]-(6,7-dimethoxyquinazolin-4-yl)-amine; (3-ethynylphenyl)-(6-nitroquinazolin-4-yl)-amine; (6,7-dimethoxyquinazolin-4-yl)-(4-ethynylphenyl)-amine; (6,7-dimethoxyquinazolin-4-yl)-(3-ethynyl-2-methylphenyl)-amine; (6-aminoquinazolin-4-yl)-(3-ethynylphenyl)-amine; (3-ethynylphenyl)-(6-methanesulfonylamino-quinazolin-4-yl)-amine; (3-ethynylphenyl)-(6,7-methylenedioxyquinazolin-4-yl)-amine; (6,7-dimethoxyquinazolin-4-yl)-(3-ethynyl-6-methylphenyl)-amine; (3-ethynylphenyl)-(7-nitroquinazolin-4-yl)-amine; (3-ethynylphenyl)-[6-(4'-toluenesulfonylamino)quinazolin-4-yl]-amine; (3-ethynylphenyl)-{6-[2'-phthalimido-eth-1'-yl-sulfonylamino]quinazolin-4-yl}-amine; (3-ethynylphenyl)-(6-guanidinoquinazolin-4-yl)-amine; (7-aminoquinazolin-4-yl)-(3-ethynylphenyl)-amine; (3-ethynylphenyl)-(7-methoxyquinazolin-4-yl)-amine; (6-carbomethoxyquinazolin-4-yl)-(3-ethynylphenyl)-amine; (7-carbomethoxyquinazolin-4-yl)-(3-ethynylphenyl)-amine; [6,7-bis(2-methoxyethoxy)quinazolin-4-yl]-(3-ethynylphenyl)-amine; (3-azidophenyl)-(6,7-dimethoxyquinazolin-4-yl)-amine; (3-azido-5-chlorophenyl)-(6,7-dimethoxyquinazolin-4-yl)-amine; (4-azidophenyl)-(6,7-dimethoxyquinazolin-4-yl)-amine; (3-ethynylphenyl)-(6-methansulfonyl-quinazolin-4-yl)-amine; (6-ethansulfanyl-quinazolin-4-yl)-(3-ethynylphenyl)-amine; (6,7-dimethoxy-quinazolin-4-yl)-(3-ethynyl-4-fluoro-phenyl)-amine; (6,7-dimethoxy-quinazolin-4-yl)-[3-(propyn-1'-yl)-phenyl]-amine; [6,7-bis-(2-methoxy-ethoxy)-quinazolin-4-yl]-(5-ethynyl-2-methyl-phenyl)-amine; [6,7-bis-(2-methoxy-ethoxy)-quinazolin-4-yl]-(3-ethynyl-4-fluoro-phenyl)-amine; [6,7-bis-(2-chloro-ethoxy)-quinazolin-4-yl]-(3-ethynyl-phenyl)-amine; [6-(2-chloro-ethoxy)-7-(2-methoxy-ethoxy)-quinazolin-4-yl]-(3-ethynyl-phenyl)-amine; [6,7-bis-(2-acetoxy-ethoxy)-quinazolin-4-yl]-(3-ethynyl-phenyl)-amine; 2-[4-(3-ethynyl-phenylamino)-7-(2-hydroxy-ethoxy)-quinazolin-6-yloxy]-ethanol; [6-(2-acetoxy-ethoxy)-7-(2-methoxy-ethoxy)-quinazolin-4-yl]-(3-ethynyl-phenyl)-amine; [7-(2-chloro-ethoxy)-6-(2-methoxy-ethoxy)-quinazolin-4-yl]-(3-ethynyl-phenyl)-amine; [7-(2-acetoxy-ethoxy)-6-(2-methoxy-ethoxy)-quinazolin-4-yl]-(3-ethynyl-phenyl)-amine; 2-[4-(3-ethynyl-phenylamino)-6-(2-hydroxy-ethoxy)-quinazolin-7-yloxy]-ethanol; 2-[4-(3-ethynyl-phenylamino)-7-(2-methoxy-ethoxy)-quinazolin-6-yloxy]-ethanol; 2-[4-(3-ethynyl-phenylamino)-6-(2-methoxy-ethoxy)-quinazolin-7-yloxy]-ethanol; [6-(2-acetoxy-ethoxy)-7-(2-methoxy-ethoxy)-quinazolin-4-yl]-(3-ethynyl-phenyl)-amine; (3-ethynyl-phenyl)-{6-(2-methoxy-ethoxy)-7-[2-(4-methyl-piperazin-1-yl)-ethoxy]-quinazolin-4-yl}-amine; (3-ethynyl-phenyl)-[7-(2-methoxy-ethoxy)-6-(2-morpholin-4-yl)-ethoxy)-quinazolin-4-yl]-amine; (6,7-diethoxyquinazolin-1-yl)-(3-ethynylphenyl)-amine; (6,7-dibutoxyquinazolin-1-yl)-(3-ethynylphenyl)-amine; (6,7-diisopropoxyquinazolin-1-yl)-(3-ethynylphenyl)-amine; (6,7-diethoxyquinazolin-1-yl)-(3-ethynyl-2-methyl-phenyl)-amine; [6,7-bis-(2-methoxy-ethoxy)-quinazolin-1-yl]-(3-ethynyl-2-methyl-phenyl)-amine; (3-ethynylphenyl)-[6-(2-hydroxy-ethoxy)-7-(2-methoxy-ethoxy)-quinazolin-1-yl]-amine; [6,7-bis-(2-hydroxy-ethoxy)-quinazolin-1-yl]-(3-ethynylphenyl)-amine; 2-[4-(3-ethynyl-phenylamino)-6-(2-methoxy-ethoxy)-quinazolin-7-yloxy]-ethanol; (6,7-dipropoxy-quinazolin-4-yl)-(3-ethynyl-phenyl)-amine; (6,7-diethoxy-quinazolin-4-yl)-(3-ethynyl-5-fluoro-phenyl)-amine; (6,7-diethoxy-quinazolin-4-yl)-(3-ethynyl-4-fluoro-phenyl)-amine; (6,7-diethoxy-quinazolin-4-yl)-(5-ethynyl-2-methyl-phenyl)-amine; (6,7-diethoxy-quinazolin-4-yl)-(3-ethynyl-4-methyl-phenyl)-amine; (6-aminomethyl-7-methoxy-quinazolin-4-yl)-(3-ethynyl-phenyl)-amine; (6-aminomethyl-7-methoxy-quinazolin-4-yl)-(3-ethynylphenyl)-amine; (6-aminocarbonylmethyl-7-methoxy-quinazolin-4-yl)-(3-ethynylphenyl)-amine; (6-aminocarbonylethyl-7-methoxy-quinazolin-4-yl)-(3-ethynylphenyl)-amine; (6-aminocarbonylmethyl-7-ethoxy-quinazolin-4-yl)-(3-ethynylphenyl)-amine; (6-aminocarbonylethyl-7-ethoxy-quinazolin-4-yl)-(3-ethynylphenyl)-amine; (6-aminocarbonylmethyl-7-isopropoxy-quinazolin-4-yl)-(3-ethynylphenyl)-amine; (6-aminocarbonylmethyl-7-propoxy-quinazolin-4-yl)-(3-ethynylphenyl)-amine; (6-aminocarbonylmethyl-7-methoxy-quinazolin-4-yl)-(3-ethynylphenyl)-amine; (6-aminocarbonylethyl-7-isopropoxy-quinazolin-4-yl)-(3-ethynylphenyl)-amine; and (6-aminocarbonylethyl-7-propoxy-quinazolin-4-yl)-(3-ethynylphenyl)-amine; (6,7-diethoxyquinazolin-1-yl)-(3-ethynylphenyl)-amine; (3-ethynylphenyl)-[6-(2-hydroxy-ethoxy)-7-(2-methoxy-ethoxy)-quinazolin-1-yl]-amine; [6,7-bis-(2-hydroxy-ethoxy)-quinazolin-1-yl]-(3-ethynylphenyl)-amine; [6,7-bis-(2-methoxy-ethoxy)-quinazolin-1-yl]-(3- ethynylphenyl)-amine; (6,7-dimethoxyquinazolin-1-yl)-(3-ethynylphenyl)-amine; (3-ethynylphenyl)-(6-methanesulfonylamino-quinazolin-1-yl)-amine; and (6-amino-quinazolin-1-yl)-(3-ethynylphenyl)-amine.

In a specific embodiment, the EGFR inhibitor of formula I is N-(3-ethynylphenyl)-6,7-bis(2-methoxyethoxy)-4-quinazolinamine.

In another specific embodiment, the EGFR inhibitor N-(3-ethynylphenyl)-6,7-bis(2-methoxyethoxy)-4-quinazolinamine is an HCl salt form.

In yet another specific embodiment, the EGFR inhibitor N-(3-ethynylphenyl)-6,7-bis(2-methoxyethoxy)-4-quinazolinamine is erlotinib, which is present in a substantially homogeneous crystalline polymorph form that exhibits an X-ray powder diffraction pattern having characteristic peaks expressed in degrees 2-theta at approximately 6.26, 12.48, 13.39, 16.96, 20.20, 21.10, 22.98, 24.46, 25.14 and 26.91.

In a further embodiment, the EGFR inhibitor blocks the formation of EGFR-EGFR homodimers and EGFR-HER2 heterodimers.

In a still further embodiment, the EGFR inhibitor is an EGFR antibody, such as, for example, cetuximab.

In another embodiment of the methods of the present invention, the patient is administered an effective amount of pertuzumab and erlotinib, where pertuzumab and erlotinib may exhibit a synergistic anti-tumor activity. In this embodiment, the tumor may be non-small cell lung carcinoma (NSCLC), for example. In another embodiment, NSCLC may be metastatic NSCLC, or poor-risk stage II or stage III NSCLC.

In other embodiments, the cancer is pancreatic cancer, or ovarian cancer, or breast cancer. In a further embodiment of the methods treating pancreatic, ovarian, or breast cancer, the patent is administered an effective amount of pertuzumab and cetuximab, where the combination may, but does not have to, exhibit a synergistic anti-tumor activity.

In further embodiments, the cancer is colorectal cancer or colon cancer, including metastatic colon cancer, or stage II-stage IV colon cancer, or colon cancer that is unsuitable for chemotherapy.

In a still further embodiment, the cancer is breast cancer.

In other embodiments, the HER2 dimerization inhibitor and the EGFR inhibitor are administered simultaneously or consecutively.

In all embodiments, if desired, the patient may be further treated with at least one chemotherapeutic agents and/or subjected to radiation therapy and/or standard of care treatment.

In another aspect, the invention concerns a method for the treatment of cancer comprising administering to a human subject, an effective amount of a HER2-dimerization inhibitor and an EGFR inhibitor, wherein the subject's cancer is not driven solely by EGFR, and the cancer is selected from the group consisting of non-small cell lung cancer (NSCLC) and pancreatic cancer.

In a further aspect, the invention concerns a method for the treatment of cancer comprising administering to a human subject an effective amount of pertuzumab and erlotinib, wherein the subject's cancer is not driven solely by EGFR, and the cancer is selected from the group consisting of non-small cell lung cancer (NSCLC) and pancreatic cancer.

In a still further aspect, the invention concerns a method for the treatment of EGFR and HER2 expressing cancer comprising administering to a human subject, an effective amount of a HER2-dimerization inhibitor and an EGFR inhibitor, wherein the subject's cancer is refractory or responds poorly to an EGFR inhibitor In another aspect, the invention concerns a method for the treatment of EGFR and HER2 expressing cancer comprising administering to a human subject, an effective amount of a HER2-dimerization inhibitor and an EGFR inhibitor, wherein the subject's tumor s refractory or responds poorly to a HER2-dimerization inhibitor.

BRIEF DESCRIPTION OF THE DRAWINGS

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 5 and 6, respectively); $V_L$ and $V_H$ domains of variant 574/pertuzumab (SEQ ID Nos. 7 and 8, respectively), and human $V_L$ and $V_H$ consensus frameworks (hum κ1, light kappa subgroup I; humIII, heavy subgroup III) (SEQ ID Nos. 9 and 10, respectively). Asterisks identify differences between variable domains of pertuzumab and murine monoclonal antibody 2C4 or between variable domains of pertuzumab and the human framework. Complementarity Determining Regions (CDRs) are in brackets.

FIGS. 3A and 3B show the amino acid sequences of pertuzumab light chain (FIG. 3A; SEQ ID NO. 11) and heavy chain (FIG. 3B; SEQ ID No. 12). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIGS. 5A and 5B depict a variant pertuzumab light chain sequence (SEQ ID No. 13) and a variant pertuzumab heavy chain sequence (SEQ ID No. 14), respectively.

FIGS. 6A and 6B depict the amino acid sequence of trastuzumab light chain (SEQ ID NO: 15) and heavy chain (SEQ ID NO: 16).

DETAILED DESCRIPTION OF THE PREFERRED EMBODIMENT

Figure 1:
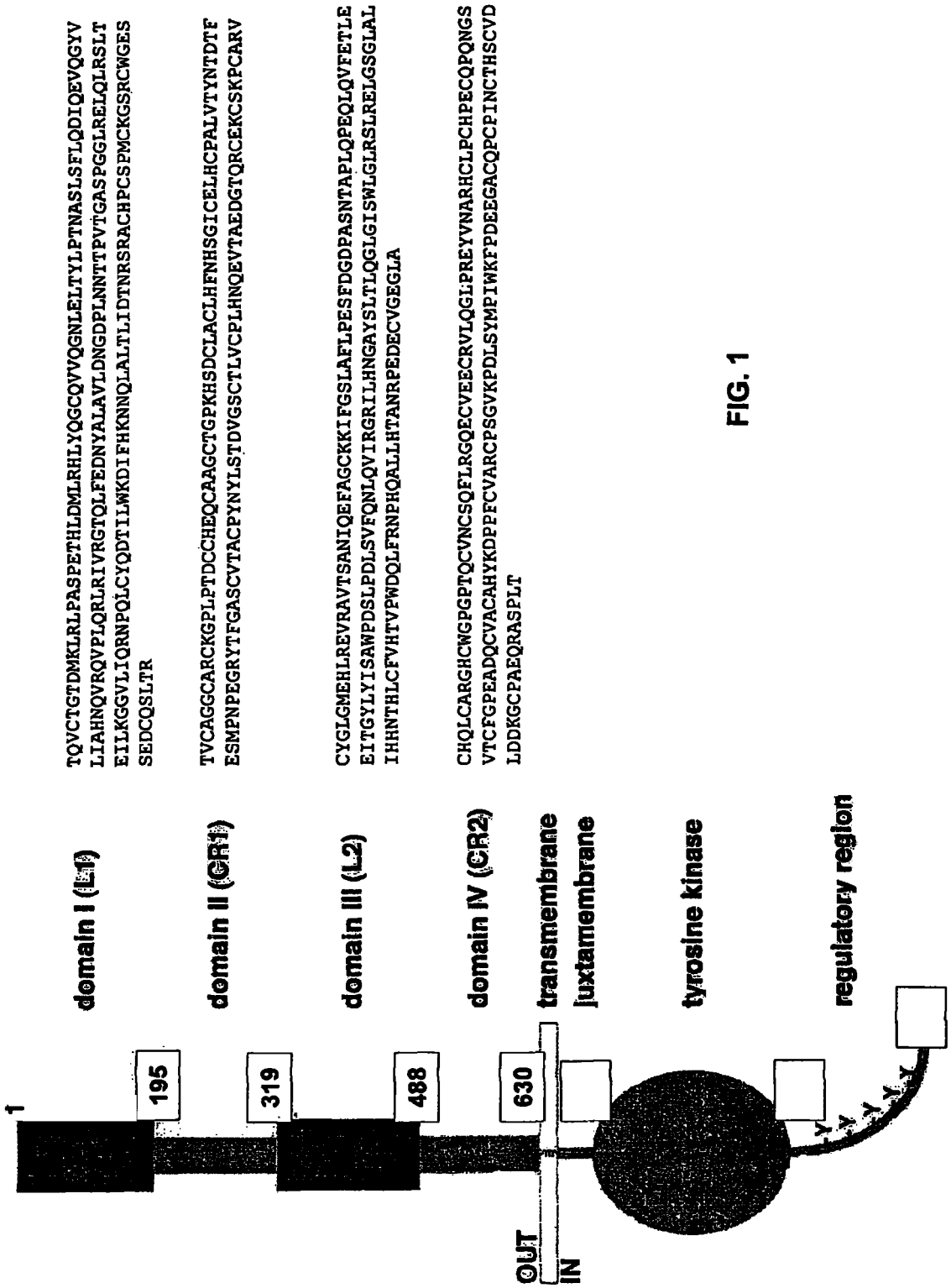
FIG. 1 provides a schematic of the HER2 protein structure, and amino acid sequences for Domains I-IV (SEQ ID Nos. 1-4, respectively) of the extracellular domain thereof.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Before the present methods, kits and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

I. DEFINITIONS

A "HER receptor" is a receptor protein tyrosine kinase which belongs to the HER receptor family and includes EGFR (ErbB1, HER1), HER2 (ErbB2), HER3 (ErbB3) and HER4 (ErbB4) receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor.

The terms "ErbB1", "HER1", "epidermal growth factor receptor" and "EGFR" are used interchangeably herein and refer to EGFR as disclosed, for example, in Carpenter et al. Ann. Rev. Biochem. 56:881-914 (1987), including naturally occurring mutant forms thereof (e.g. a deletion mutant EGFR as in Ullrich et al, Nature (1984) 309:418425 and Humphrey et al. PNAS (USA) 87:4207-4211 (1990)), as well we variants thereof, such as EGFRvIII. Variants of EGFR also include deletional, substitutional and insertional variants, for example those described in Lynch et al (New England Journal of Medicine 2004, 350:2129), Paez et al (Science 2004, 304: 1497), and Pao et al (PNAS 2004, 101:13306).

The expressions "ErbB2" and "HER2" are used interchangeably herein and refer to human HER2 protein described, for example, in Semba et al., PNAS (USA) 82:6497-6501 (1985) and Yamamoto et al. Nature 319:230-234 (1986) (GenBank accession number X03363). The term "AerbB2" refers to the gene encoding human HER2 and Aneu≈refers to the gene encoding rat p185$^{neu}$. Preferred HER2 is native sequence human HER2.

Herein, "HER2 extracellular domain" or "HER2 ECD" refers to a domain of HER2 that is outside of a cell, either anchored to a cell membrane, or in circulation, including fragments thereof. In one embodiment, the extracellular domain of HER2 may comprise four domains: "Domain I" (amino acid residues from about 1-195, "Domain II" (amino acid residues from about 196-319), "Domain III" (amino acid residues from about 320-488), and "Domain IV" (amino acid residues from about 489-630) (residue numbering without signal peptide). See Garrett et al. Mol. Cell. 11: 495-505 (2003), Cho et al. Nature 421: 756-760 (2003), Franklin et al. Cancer Cell 5:317-328 (2004), and Plowman et al. Proc. Natl. Acad. Sci. 90:1746-1750 (1993), as well as FIG. 1 herein.

"ErbB3" and "HER3" refer to the receptor polypeptide as disclosed, for example, in U.S. Pat. Nos. 5,183,884 and 5,480, 968 as well as Kraus et al. PNAS (USA) 86:9193-9197 (1989).

The terms "ErbB4" and "HER4" herein refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., J. Biol. Chem. 247:7612-7621 (1972)); transforming growth factor alpha (TGF-α) (Marquardt et al., Science 223:1079-1082 (1984)); amphiregulin also known as schwanoma or keratinocyte autocrine growth factor (Shoyab et al. Science 243:1074-1076 (1989); Kimura et al. Nature 348:257-260 (1990); and Cook et al. Mol. Cell. Biol. 11:2547-2557 (1991)); betacellulin (Shing et al., Science 259:1604-1607 (1993); and Sasada et al. Biochem. Biophys. Res. Commun. 190:1173 (1993)); heparin-binding epidermal growth factor (HB-EGF) (Higashiyama et al., Science 251:936-939 (1991)); epiregulin (Toyoda et al., J. Biol. Chem. 270:7495-7500 (1995); and Komurasaki et al. Oncogene 15:2841-2848 (1997)); a heregulin (see below); neuregulin-2 (NRG-2) (Carraway et al., Nature 387:512-516 (1997)); neuregulin-3 (NRG-3) (Zhang et al., Proc. Natl. Acad. Sci. 94:9562-9567 (1997)); neuregulin-4 (NRG-4) (Harari et al. Oncogene 18:2681-89 (1999)); and cripto (CR-1) (Kannan et al. J. Biol. Chem. 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4, and heregulins.

"Heregulin" (HRG) when used herein refers to a polypeptide encoded by the heregulin gene product as disclosed in U.S. Pat. No. 5,641,869, or Marchionni et al., Nature, 362: 312-318 (1993). Examples of heregulins include heregulin-α, heregulin-β1, heregulin-β2 and heregulin-β3 (Holmes et al., Science, 256:1205-1210 (1992); and U.S. Pat. No. 5,641, 869); neu differentiation factor (NDF) (Peles et al. Cell 69: 205-216 (1992)); acetylcholine receptor-inducing activity (ARIA) (Falls et al. Cell 72:801-815 (1993)); glial growth factors (GGFs) (Marchionni et al., Nature, 362:312-318 (1993)); sensory and motor neuron derived factor (SMDF) (Ho et al. J. Biol. Chem. 270:14523-14532 (1995)); γ-heregulin (Schaefer et al. Oncogene 15:1385-1394 (1997)).

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.*, 269(20):14661-14665 (1994), for example. Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

A "HER inhibitor" is an agent which interferes with HER activation or function. Examples of HER inhibitors include HER antibodies (e.g. EGFR, HER2, HER3, or HER4 antibodies); EGFR-targeted drugs; small molecule HER antagonists; HER tyrosine kinase inhibitors; HER2 and EGFR dual tyrosine kinase inhibitors such as lapatinib/GW572016; antisense molecules (see, for example, WO2004/87207); and/or agents that bind to, or interfere with function of, downstream signaling molecules, such as MAPK or Akt (see FIG. 5). Preferably, the HER inhibitor is an antibody or small molecule which binds to a HER receptor.

Figure 4:
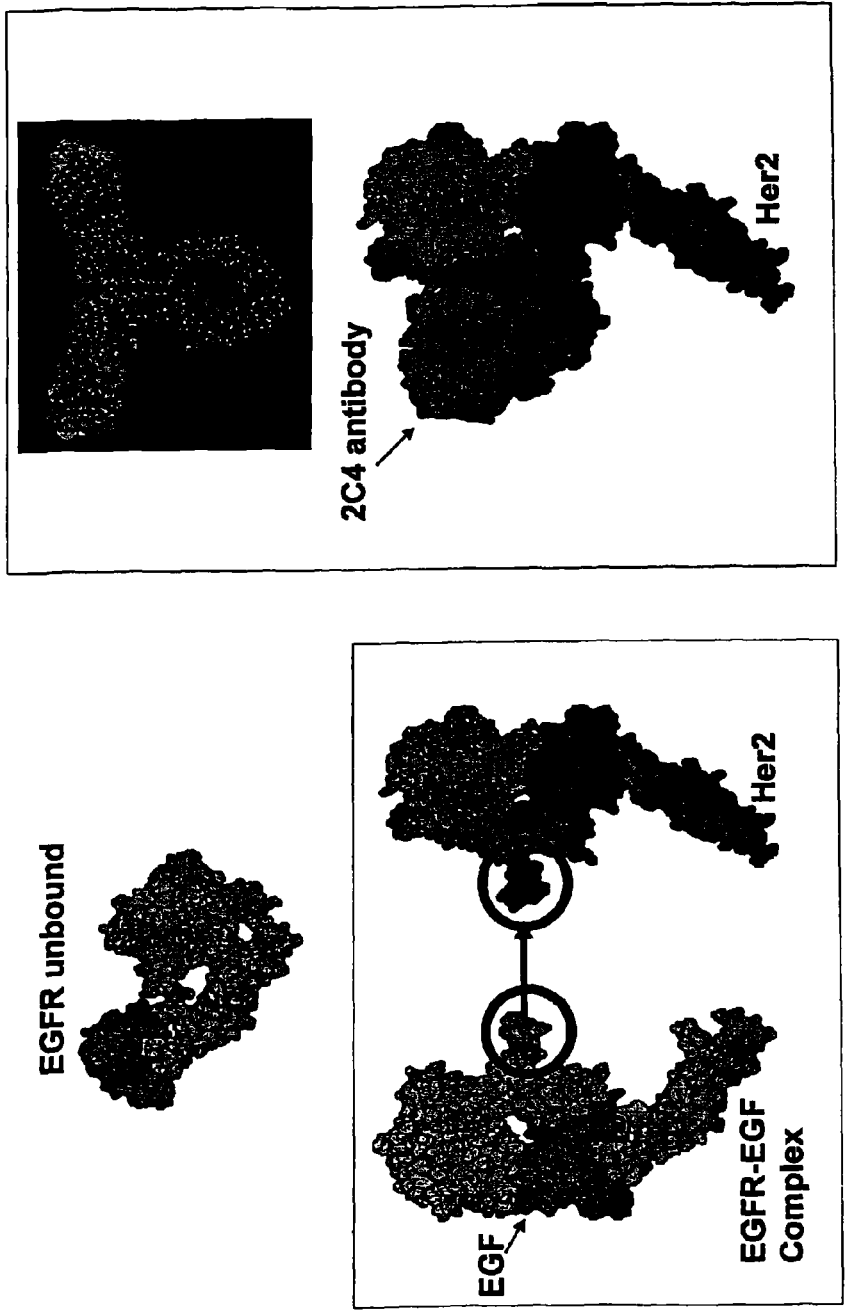
FIG. 4 depicts, schematically, binding of 2C4 at the heterodimeric binding site of HER2, thereby preventing heterodimerization with activated EGFR or HER3.

A "HER dimerization inhibitor" or "HDI" is an agent which inhibits formation of a HER homodimer or HER heterodimer. Preferably, the HER dimerization inhibitor is an antibody, for example an antibody which binds to HER2 at the heterodimeric binding site thereof. However, HER dimerization inhibitors also include peptide and non-peptide small molecules, and other chemical entities which inhibit the formation of HER homo- or heterodimers. The most preferred HER dimerization inhibitor herein is pertuzumab or MAb 2C4. Binding of 2C4 to the heterodimeric binding site of HER2 is illustrated in FIG. 4. Other examples of HER dimerization inhibitors include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; antibodies which bind to HER4 and inhibit dimerization thereof with one or more other HER receptors; peptide dimerization inhibitors (U.S. Pat. No. 6,417,168); antisense dimerization inhibitors; etc.

A "HER2 dimerization inhibitor" herein is a HER2 antibody or other HER2 antagonist, such as a peptide or on-peptide small molecule, which bind to HER2 and interferes with the formation of HER2-containing oligomers, including HER2 homo- and heterodimers, such as one or more of HER2-HER2, HER2-EGFR, HER2-HER3, and HER2-HER4 heterodimers. Preferably, the HER2 dimerization inhibitor is a molecule, such as an HER2 antibody or a peptide or non-peptide small molecule, that blocks the formation of all of HER2-HER2, HER2-EGFR and HER2-HER3 heterodimers, for example by binding to HER2 at a location required for heterodimerization, such as the heterodimeric binding site shown in FIG. 4. A typical representative of such HER2 dimerization inhibitors is pertuzumab, which was also listed as a "HER dimerization inhibitor" in a broader sense.

As used herein, the term "EGFR inhibitor" refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N-8-(3-chloro-4-fluoro-phenyl)-N-2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Sugen); and AG1571 (SU 5271; Sugen).

A "HER antibody" or "HER antibody" is an antibody that binds to a HER receptor. Optionally, the HER antibody further interferes with HER activation or function. Preferably, the HER antibody binds to the HER2 receptor. A HER2 antibody of particular interest herein is pertuzumab. Another example of a HER2 antibody is trastuzumab. Examples of EGFR antibodies include cetuximab and ABX0303.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Phosphorylation" refers to the addition of one or more phosphate group(s) to a protein, such as a HER receptor, or substrate thereof.

An antibody which "inhibits HER dimerization" is an antibody which inhibits, or interferes with, formation of a HER dimer, regardless of the underlying mechanism. Preferably, such an antibody binds to HER2 at the heterodimeric binding site thereof. The most preferred dimerization inhibiting antibody herein is pertuzumab or MAb 2C4. Binding of 2C4 to the heterodimeric binding site of HER2 is illustrated in FIG. 4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; and antibodies which bind to HER4 and inhibit dimerization thereof with one or more other HER receptors.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. *Cancer Cell* 5:317-328 (2004).

The HER2 antibody may "inhibit HRG-dependent AKT phosphorylation" and/or inhibit "HRG- or TGFα-dependent MAPK phosphorylation" more effectively (for instance at least 2-fold more effectively) than trastuzumab (see Agus et al. *Cancer Cell* 2: 127-137 (2002) and WO01/00245, by way of example).

The HER2 antibody may be one which, like pertuzumab, does "not inhibit HER2 ectodomain cleavage" (Molina et al. *Cancer Res.* 61:4744-4749(2001)). Trastuzumab, on the other hand, can inhibit HER2 ectodomain cleavage.

A HER2 antibody that "binds to a heterodimeric binding site" of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III. Preferably the antibody that binds to domain II binds to the junction between domains I, II and III of HER2.

Herein "time to disease progression" or "TTP" refer to the time, generally measured in weeks or months, from the time of initial treatment until the cancer progresses or worsens. Such progression can be evaluated by the skilled clinician.

By "extending TTP" is meant increasing the time to disease progression in a treated patient relative to an untreated patient, relative to a patient treated with monotherapy with a HER dimerization inhibitor (such as, for example, pertuzumab) and/or with an EGFR inhibitor (e.g. erlotinib or gefitinib) alone as opposed to combination therapy, or relative to a patient treated with an approved anti-tumor agent for the treatment of cancer in question.

"Survival" refers to the patient remaining alive, and includes overall survival as well as progression free survival.

"Overall survival" refers to the patient remaining alive for a defined period of time, such as 1 year, 5 years, etc from the time of diagnosis or treatment.

"Progression free survival" refers to the patient remaining alive, without disease progression.

By "extending survival" is meant increasing overall or progression free survival in a treated patient relative to an untreated patient, relative to a patient treated with monotherapy with a HER dimerization inhibitor (such as, for example, pertuzumab) and/or with an EGFR inhibitor (e.g. erlotinib or gefitinib) alone as opposed to combination therapy, or relative to a patient treated with an approved anti-tumor agent for the treatment of the cancer in question.

An "objective response" refers to a measurable response, including complete response (CR) or partial response (PR).

By "complete response" or "CR" is intended the disappearance of all signs of cancer in response to treatment. This does not always mean the cancer has been cured.

"Partial response" or "PR" refers to a decrease in the size of one or more tumors or lesions, or in the extent of cancer in the body, in response to treatment.

The term "refractory tumor" or "refractory cancer" is used to refer to tumors that fail or are resistant to a certain treatment, such as "standard of care" treatment, e.g., treatment with chemotherapeutic agents alone, radiation alone or combinations thereof. For the purposes of this specification, refractory tumors also encompass tumors that appear to be inhibited by such treatment(s) but recur within 12 months from the completion of such treatment.

A tumor which "responds poorly" to treatment with an EGFR inhibitor alone does not show statistically significant improvement in response to such treatment when compared to no treatment or treatment with placebo in a recognized animal model or a human clinical trial, or which responds to initial treatment with an EGFR inhibitor (e.g. antibody) but grows as treatment is continued.

A tumor which "responds poorly" to treatment with a HER2-dimerization inhibitor alone does not show statistically significant improvement in response to such treatment when compared to no treatment or treatment with placebo in a recognized animal model or a human clinical trial, or which responds to initial treatment with a HER2-dimerization inhibitor (e.g. antibody) but grows as treatment is continued.

The term "standard of care" is used to refer to a treatment process that an ordinary skilled prudent physician uses to treat a certain disease, such as cancer. The standard of care varies depending on the type and stage of cancer, the patient's condition and treatment history, and the like, and will be apparent to those skilled in the art.

Protein "expression" refers to conversion of the information encoded in a gene into messenger RNA (mRNA) and then to the protein.

Herein, a sample or cell that "expresses" a protein of interest (such as a HER receptor or HER ligand) is one in which mRNA encoding the protein, or the protein, including fragments thereof, is determined to be present in the sample or cell.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced also increases in the proportion of the number of copies made of the particular gene expressed.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

A "native sequence" polypeptide is one which has the same amino acid sequence as a polypeptide (e.g., HER receptor or HER ligand) derived from nature, including naturally occurring or allelic variants. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "antibody" herein is used in the broadest sense and specifically covers monoclonal antibodies, polyclonal antibodies, multispecific antibodies (e.g. bispecific antibodies), and antibody fragments, so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816, 567), phage display technologies (see, e.g., Clackson et al., *Nature*, 352:624-628 (1991); Marks et al., *J. Mol. Biol.*, 222: 581-597 (1991); Sidhu et al., *J. Mol. Biol.* 338(2):299-310 (2004); Lee et al., *J. Mol. Biol.*340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/ 34096; WO 1996/33735; WO 1991/10741; Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855

(1984)). Chimeric antibodies of interest herein include "primatized" antibodies comprising variable domain antigen-binding sequences derived from a non-human primate (e.g. Old World Monkey, Ape etc) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or trastuzumab as described in Table 3 of U.S. Pat. No. 5,821,337 expressly incorporated herein by reference; humanized 520C9 (WO93/21319); and humanized 2C4 antibodies such as pertuzumab as described herein.

For the purposes herein, "trastuzumab," "HERCEPTIN®," and "huMAb4D5-8" refer to an antibody comprising the light and heavy chain amino acid sequences in SEQ ID NOS. 15 and 16, respectively.

Herein, "pertuzumab" and "OMNITARG™" refer to an antibody comprising the light and heavy chain amino acid sequences of SEQ ID NOS. 11 and 12, respectively.

Herein, "variant pertuzumab" refers to an antibody comprising the light and heavy chain amino acid sequences of SEQ ID NOS: 13 and 14, respectively.

An "intact antibody" herein is one which comprises two antigen binding regions, and an Fc region. Preferably, the intact antibody has a functional Fc region.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragment(s).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab=fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)), and regulates homeostasis of immunoglobulins.

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

A "naked antibody" is an antibody that is not conjugated to a heterologous molecule, such as a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "main species antibody" herein refers to the antibody structure in a composition which is the quantitatively predominant antibody molecule in the composition. In one embodiment, the main species antibody is a HER2 antibody, such as an antibody that binds to Domain II of HER2, antibody that inhibits HER dimerization more effectively than trastuzumab, and/or an antibody which binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 11 and 12 (pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g. deamidated antibody variant), a basic variant, an antibody with an amino-terminal leader extension (e.g. VHS-) on one or two light chains thereof, an antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moeities attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Where the antibody has an Fc region, an oligosaccharide structure may be attached to one or two heavy chains of the antibody, e.g. at residue 299 (298, Eu numbering of residues). For pertuzumab, G0 was the predominant oligosaccharide structure, with other oligosaccharide structures such as G0-F, G-1, Man5, Man6, G1-1, G1(1-6), G1(1-3) and G2 being found in lesser amounts in the pertuzumab composition.

Unless indicated otherwise, a "G1 oligosaccharide structure" herein includes G-1, G1-1, G1(1-6) and G1(1-3) structures.

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

A "deamidated" antibody is one in which one or more asparagine residues thereof has been derivatized, e.g. to an aspartic acid, a succinimide, or an iso-aspartic acid.

The terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer.

An "advanced" cancer is one which has spread outside the site or organ of origin, either by local invasion or metastasis.

A "recurrent" cancer is one which has regrown, either at the initial site or at a distant site, after a response to initial therapy.

For the purposes of the present invention, lung cancer, including non-small cell lung cancer (NSCLC) is classified using the Revised International System for Staging Lung Cancer, adopted in 1997 by the American Joint Committee on Cancer and the Union Internationale Centre 1 Cancer (Mountain CF: Revisions in the International System for Staging Lung Cancer. Chest 111(6): 1710-1717, 1997).

Stage 1 (T1): A tumor that is 3 cm or less in greatest dimension, surrounded by lung or visceral pleura, and without bronchoscopic evidence of invasion more proximal than the lobar bronchus (i.e., not in the main bronchus).

Stage 2 (T2): A tumor with any of the following features of size or extent: (a) more than 3 cm in greatest dimension, (b) involves the main bronchus, 2 cm or more distal to the carina, (c) invades the visceral pleura, (d) associated with atelectasis or obstructive pneumonitis that extends to the hilar region but does not involve the entire lung.

Stage 3 (T3): A tumor of any size that directly invades any of the following: chest wall (including superior sulcus tumors), diaphragm, mediastinal pleura, parietal pericardium; or tumor in the main bronchus less than 2 cm distal to the carina but without involvement of the carina; or associated atelectasis or obstructive pneumonitis of the entire lung.

Stage 4 (T4): A tumor of any size that invades any of the following: mediastinum, heart, great vessels, trachea, esophagus, vertebral body, carina; or separate tumor nodules in the same lobe; or tumor with a malignant pleural effusion.

Herein, a "subject" is a human subject. The subject may be a "cancer subject," i.e. one who is suffering or at risk for suffering from one or more symptoms of cancer.

A "tumor sample" herein is a sample derived from, or comprising tumor cells from, a patient's tumor. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

A "fixed" tumor sample is one which has been histologically preserved using a fixative.

A "formalin-fixed" tumor sample is one which has been preserved using formaldehyde as the fixative.

An "embedded" tumor sample is one surrounded by a firm and generally hard medium such as paraffin, wax, celloidin, or a resin. Embedding makes possible the cutting of thin sections for microscopic examination or for generation of tissue microarrays (TMAs).

A "paraffin-embedded" tumor sample is one surrounded by a purified mixture of solid hydrocarbons derived from petroleum.

Herein, a "frozen" tumor sample refers to a tumor sample which is, or has been, frozen.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A cancer or biological sample which "displays HER activation" is one which, in a diagnostic test, demonstrates activation or phosphorylation of a HER receptor. Such activation can be determined directly (e.g. by measuring HER phosphorylation by ELISA) or indirectly (e.g. by gene expression profiling or by detecting HER heterodimers, as described herein).

Herein, "gene expression profiling" refers to an evaluation of expression of one or more genes as a surrogate for determining HER phosphorylation directly.

A "phospho-ELISA assay" herein is an assay in which phosphorylation of one or more HER receptors, especially HER2, is evaluated in an enzyme-linked immunosorbent assay (ELISA) using a reagent, usually an antibody, to detect phosphorylated HER receptor, substrate, or downstream signaling molecule. Preferably, an antibody which detects phosphorylated HER2 is used. The assay may be performed on cell lysates, preferably from fresh or frozen biological samples.

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress or amplify HER receptor" is one which does not have higher than normal levels of HER receptor protein or gene compared to a noncancerous cell of the same tissue type. Antibodies that inhibit HER dimerization, such as pertuzumab, may be used to treat cancer which does not overexpress or amplify HER2 receptor.

A tumor is "not driven solely by EGFR" when signaling pathways other than signaling through EGFR contribute to the formation, development or spread of an EGFR-expressing tumor. Thus, for example, a tumor is not driven solely by EGFR, if signaling through HER2 also contributes to the pathogenesis of tumor.

Herein, an "anti-tumor agent" refers to a drug used to treat cancer. Non-limiting examples of anti-tumor agents herein include chemotherapeutic agents, HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125, HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

An "approved anti-tumor agent" is a drug used to treat cancer which has been accorded marketing approval by a regulatory authority such as the Food and Drug Administration (FDA) or foreign equivalent thereof.

Where a HER dimerization inhibitor is administered as a "single anti-tumor agent" it is the only anti-tumor agent administered to treat the cancer, i.e. it is not administered in combination with another anti-tumor agent, such as chemotherapy.

By "standard of care" herein is intended the anti-tumor agent or agents that are routinely used to treat a particular form of cancer. For example, for platinum-resistant ovarian cancer, the standard of care is topotecan or liposomal doxorubicin.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Examples of HER2 antibodies that induce apoptosis are 7C2 and 7F3.

The "epitope 2C4" is the region in the extracellular domain of HER2 to which the antibody 2C4 binds. In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds to the 2C4 epitope of HER2. Epitope 2C4 comprises residues from Domain II in the extracellular domain of HER2. 2C4 and pertuzumab binds to the extracellular domain of HER2 at the junction of domains I, II and III. Franklin et al. *Cancer Cell* 5:317-328 (2004).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive of the HER2 ECD, residue numbering including signal peptide).

The "epitope 7C2/7F3" is the region at the N terminus, within Domain I, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of the HER2 ECD, residue numbering including signal peptide).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); sorafenib (Bayer); SU-11248 (Pfizer); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

An "anti-hormonal agent" or "endocrine therapeutic" is an agent that acts to regulate, reduce, block, or inhibit the effects of hormones that can promote the growth of cancer. They may be hormones themselves. Examples include: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure antiestrogens without agonist properties, such as EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide.

An "antimetabolite chemotherapeutic agent" is an agent which is structurally similar to a metabolite, but can not be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODAθ), 6-mercaptopurine, methotrexate, 6-thioguanine, pemetrexed, raltitrexed, arabinosylcytosine ARA-C cytarabine (CYTOSAR-U®), dacarbazine (DTIC-DOME®), azocytosine, deoxycytosine, pyridmidene, fludarabine (FLUDARA®), cladrabine, 2-deoxy-D-glucose etc. The preferred antimetabolite chemotherapeutic agent is gemcitabine.

"Gemcitabine" or "2'-deoxy-2',2'-difluorocytidine monohydrochloride (b-isomer)" is a nucleoside analogue that exhibits antitumor activity. The empirical formula for gemcitabine HCl is C9H11F2N3O4 A HCl. Gemcitabine HCl is sold by Eli Lilly under the trademark GEMZAR®.

A "platinum-based chemotherapeutic agent" comprises an organic compound which contains platinum as an integral part of the molecule. Examples of platinum-based chemotherapeutic agents include carboplatin, cisplatin, and oxaliplatinum.

By "platinum-based chemotherapy" is intended therapy with one or more platinum-based chemotherapeutic agents, optionally in combination with one or more other chemotherapeutic agents.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

By "platinum-resistant" cancer is meant that the cancer patient has progressed while receiving platinum-based chemotherapy (i.e. the patient is "platinum refractory"), or the patient has progressed within 12 months (for instance, within 6 months) after completing a platinum-based chemotherapy regimen.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to vascular endothelial growth factor (VEGF), such as bevacizumab (AVASTIN®) (see U.S. Pat. No. 6,884,879B1).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ, colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2 (e.g. PROLEUKIN®), IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the HER2 receptor tyrosine kinase (Pfizer and OSI); dual-HER inhibitors such as EKB-569 (available from Wyeth) which preferentially binds EGFR but inhibits both HER2 and EGFR-overexpressing cells; GW572016 (available from Glaxo) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-I signaling; non-HER targeted TK inhibitors such as Imatinib mesylate (Gleevac®) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m² dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

II. USE OF INHIBITORS OF HER2 HETERODIMER FORMATION AND EGFR INHIBITORS

The present invention is based, at least in part, on the recognition that a combination of an inhibitor of HER2 heterodimer formation (HER2 dimerization inhibitor) and an EGFR inhibitor provides significant benefits in tumor treatment. In particular, the present invention is based on the finding that combination treatment with inhibitors of HER2 heterodimer formation, such as pertuzumab (OMNI-TARG™, Genentech, Inc.), and EGFR inhibitors, such as erlotinib (TARCEVA™, Genentech, Inc.) provides unexpected benefits in the treatment of cancer.

1. HER2 Dimerization Inhibitors

Typical representatives of HER2 dimerization inhibitors are antibodies or other molecules that bind to a HER2 receptor at a location that would otherwise participate in the formation of a HER2 oligomer, such as HER2 homo- and/or heterodimer. As a result of antibody binding, formation of the HER2/HER2 homodimers and/or EGFR/HER2 and/or HER2/HER3 heterodimer(s) will be inhibited, which provides therapeutic benefits for the patient. In a preferred embodiment, the antibody blocks the formation of all of HER2/HER2 homodimers and EGFR/HER2 and HER2/HER3 heterodimers.

A preferred dimerization inhibiting antibody herein is pertuzumab or a variant thereof. Binding of 2C4 to the heterodimeric binding site of HER2 is illustrated in FIG. 4. Pertuzumab (also known as recombinant human monoclonal antibody 2C4; OMNITARG™, Genentech, Inc, South San Francisco) represents the first in a new class of agents known as HER dimerization inhibitors (HDI) and functions to inhibit the ability of HER2 to form active heterodimers with other HER receptors (such as EGFR/EGFR, HER3 and HER4) and is active irrespective of HER2 expression levels. See, for example, Harari and Yarden, *Oncogene* 19:6102-14 (200); Yarden and Sliwkowski, *Nat Rev Mol Cell Biol* 2:127-37 (2001); Sliwkowski *Nat Struct Biol* 10:158-9 (2003); Cho et al., *Nature* 421:756-60 (2003); ad Malik et al., *Pro Am Soc Cancer Res* 44:176-7 (2003).

Pertuzumab blockade of the formation of HER2/HER3 heterodimers in tumor cells has been demonstrated to inhibit critical cell signaling, which results in reduced tumor proliferation and survival (Agus et al. *Cancer Cell* 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable, locally advanced, recurrent or metastatic solid tumors that had progressed during or after standard therapy were treated with pertuzumab given intravenously every 3 weeks. Pertuzumab was generally well tolerated. Tumor regression was achieved in 3 of 20 patients evaluable for response. Two patients had confirmed partial responses. Stable disease lasting for more than 2.5 months was observed in 6 of 21 patients (Agus et al. *Pro Am Soc Clin Oncol* 22:192 (2003)). At doses of 2.0-15 mg/kg, the pharmacokinetics of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. *Pro Am Soc Clin Oncol* 22:197 (2003)).

As mentioned above, in one embodiment, the methods and compositions of the present invention may use pertuzumab and/or pertuzumab variants as HER2 dimerization inhibitors. The preferred embodiment herein of a pertuzumab main species antibody is one comprising the variable light and variable heavy amino acid sequences in SEQ ID Nos. 3 and 4, and most preferably comprising a light chain amino acid sequence selected from SEQ ID No. 11 and 13, and a heavy chain amino acid sequence selected from SEQ ID No. 12 and 14 (including deamidated and/or oxidized variants of those sequences). In one embodiment, the composition comprises a mixture of the main species pertuzumab antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab=)2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS-. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX-10θ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialilated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

One can evaluate the ability of an antibody to block ligand activation of a HER2 receptor by studying HER2 dimers directly, or by evaluating HER2 activation, or downstream signaling, which results from HER2 dimerization, and/or by evaluating the antibody-HER2 binding site, etc. Assays for screening for antibodies with the ability to inhibit ligand activation of a HER2 receptor are described in Agus et al. *Cancer Cell* 2: 127-137 (2002) and WO01/00245 (Adams et al.). By way of example only, one may assay for: inhibition of HER2 dimer formation (see, e.g., FIG. 1A-B of Agus et al. *Cancer Cell* 2: 127-137 (2002); and WO01/00245); reduction in HER2 ligand activation of cells which express HER2 dimers (WO01/00245 and FIG. 2A-B of Agus et al. *Cancer Cell* 2: 127-137 (2002), for example); blocking of HER2 ligand binding to cells which express HER2 dimers (WO01/00245, and FIG. 2E of Agus et al. *Cancer Cell* 2: 127-137 (2002), for example); cell growth inhibition of cancer cells (e.g. MCF7, MDA-MD-134, ZR-75-1, MD-MB-175, T-47D cells) which express HER2 dimers in the presence (or absence) of HER2 ligand (WO01/00245 and FIGS. 3A-D of Agus et al. *Cancer Cell* 2: 127-137 (2002), for instance); inhibition of downstream signaling (for instance, inhibition of HRG-dependent AKT phosphorylation or inhibition of HRG- or TGFα-dependent MAPK phosphorylation) (see, WO01/00245, and FIG. 2C-D of Agus et al. *Cancer Cell* 2: 127-137 (2002), for example). One may also assess whether the antibody inhibits HER2 dimerization by studying the antibody-HER2 binding site, for instance, by evaluating a structure or model, such as a crystal structure, of the antibody bound to HER2 (See, for example, Franklin et al. *Cancer Cell* 5:317-328 (2004)).

2. EGFR Inhibitors

EGFR inhibitors are molecules that bind to and, optionally, inhibit a biological activity of an epidermal growth factor receptor (EGFR, ErbB1, EGFR).

In a particular embodiment, the EGFR inhibitor is a small molecule which has a general formula I (see, U.S. Pat. No. 5,757,498):

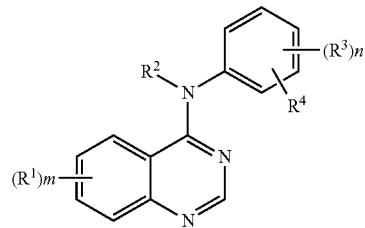

I wherein:
X is halo or hydroxy;
m is 1, 2, or 3;
each $R^1$ is independently selected from the group consisting of hydrogen, halo, hydroxy, hydroxyamino, carboxy, nitro, guanidino, ureido, cyano, trifluoromethyl, and —($C_1$-$C_4$ alkylene)-W-(phenyl) wherein W is a single bond, O, S or NH;

or each $R^1$ is independently selected from $R^9$ and $C_1$-$C_4$ alkyl substituted by cyano, wherein $R^9$ is selected from the group consisting of $R^5$, —$OR^6$, —$NR^6R^6$, —$C(O)R^7$, —$NHOR^5$, —$OC(O)R^6$, cyano, A and —$YR^5$; $R^5$ is $C_1$-$C_4$ alkyl; $R^6$ is independently hydrogen or $R^5$; $R^7$ is $R^5$, —$OR^6$ or —$NR^6R^6$; A is selected from piperidino, morpholino, pyrrolidino, 4-$R^6$-piperazin-1-yl, imidazol-1-yl, 4-pyridon-1-yl, —($C_1$-$C_4$ alkylene)(CO2H), phenoxy, phenyl, phenylsulfanyl, $C_2$-$C_4$ alkenyl, and —($C_1$-$C_4$ alkylene)C(O)$NR^6R^6$; and Y is S, SO, or $SO_2$; wherein the alkyl moieties in $R^5$, —$OR^6$ and —$NR^6R^6$ are optionally substituted by one to three halo substituents and the alkyl moieties in $R^5$, —$OR^6$ and —$NR^6R^6$ are optionally substituted by 1 or 2 $R^9$ groups, and wherein the alkyl moieties of said optional substituents are optionally substituted by halo or $R^9$, with the proviso that two heteroatoms are not attached to the same carbon atom;

or each $R^1$ is independently selected from —$NHSO_2R^5$, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $R^{10}$—($C_2$-$C_4$)-alkanoylamino wherein $R^{10}$ is selected from halo, —$OR^6$, $C_2$-$C_4$ alkanoyloxy, —$C(O)R^7$, and —$NR^6R^6$; and wherein said —$NHSO_2R^5$, phthalimido-($C_1$-$C_4$-alkylsulfonylamino, benzamido, benzenesulfonylamino, 3-phenylureido, 2-oxopyrrolidin-1-yl, 2,5-dioxopyrrolidin-1-yl, and $R^{10}$—($C_2$-$C_4$)-alkanoylamino $R^1$ groups are optionally substituted by 1 or 2 substituents independently selected from halo, $C_1$-$C_4$ alkyl, cyano, methanesulfonyl and $C_1$-$C_4$ alkoxy;

or two $R^1$ groups are taken together with the carbons to which they are attached to form a 5-8 membered ring that includes 1 or 2 heteroatoms selected from O, S and N;

$R^2$ is hydrogen or $C_1$-$C_6$ alkyl optionally substituted by 1 to 3 substituents independently selected from halo, $C_1$-$C_4$ alkoxy, —$NR^6R^6$, and —$SO_2R^5$;

n is 1 or 2 and each $R^3$ is independently selected from hydrogen, halo, hydroxy, $C_1$-$C_6$ alkyl, —$NR^6R^6$, and $C_1$-$C_4$ alkoxy, wherein the alkyl moieties of said $R^3$ groups are optionally substituted by 1 to 3 substituents independently selected from halo, $C_1$-$C_4$ alkoxy, —$NR^6R^6$, and —$SO_2R$; and, $R^4$ is azido or -(ethynyl)-$R^{11}$ wherein $R^{11}$ is hydrogen or $C_1$-$C_6$ alkyl optionally substituted by hydroxy, —$OR^6$, or —$NR^6R^6$.

In another embodiment, the EGFR inhibitor is a compound of formula I selected from the group consisting of:
(6,7-dimethoxyquinazolin-4-yl)-(3-ethynylphenyl)-amine; (6,7-dimethoxyquinazolin-4-yl)-[3-(3'-hydroxypropyn-1-yl)phenyl]-amine; [3-(2'-(aminomethyl)-ethynyl)phenyl]-(6,7-dimethoxyquinazolin-4-yl)-amine; (3-ethynylphenyl)-(6-nitroquinazolin-4-yl)-amine; (6,7-dimethoxyquinazolin-4-yl)-(4-ethynylphenyl)-amine; (6,7-dimethoxyquinazolin-4-yl)-(3-ethynyl-2-methylphenyl)-amine; (6-aminoquinazolin-4-yl)-(3-ethynylphenyl)-amine; (3-ethynylphenyl)-(6-methanesulfonylaminoquinazolin-4-yl)-amine; (3-ethynylphenyl)-(6,7-methylenedioxyquinazolin-4-yl)-amine; (6,7-dimethoxyquinazolin-4-yl)-(3-ethynyl-6-methylphenyl)-amine; (3-ethynylphenyl)-(7-nitroquinazolin-4-yl)-amine; (3-ethynylphenyl)-[6-(4'-toluenesulfonylamino)quinazolin-4-yl]-amine; (3-ethynylphenyl)-{6-[2'-phthalimidoeth-1'-yl-sulfonylamino]quinazolin-4-yl}-amine; (3-ethynylphenyl)-(6-guanidinoquinazolin-4-yl)-amine; (7-aminoquinazolin-4-yl)-(3-ethynylphenyl)-amine; (3-ethynylphenyl)-(7-methoxyquinazolin-4-yl)-amine; (6-carbomethoxyquinazolin-4-yl)-(3-ethynylphenyl)- amine; (7-carbomethoxyquinazolin-4-yl)-(3-ethynylphenyl)-amine; [6,7-bis(2-methoxyethoxy)quinazolin-4-yl]-(3-ethynylphenyl)-amine; (3-azidophenyl)-(6,7-dimethoxyquinazolin-4-yl)-amine; (3-azido-5-chlorophenyl)-(6,7-dimethoxyquinazolin-4-yl)-amine; (4-azidophenyl)-(6,7-dimethoxyquinazolin-4-yl)-amine; (3-ethynylphenyl)-(6-methansulfonyl-quinazolin-4-yl)-amine; (6-ethansulfanyl-quinazolin-4-yl)-(3-ethynylphenyl)-amine; (6,7-dimethoxy-quinazolin-4-yl)-(3-ethynyl-4-fluoro-phenyl)-amine; (6,7-dimethoxy-quinazolin-4-yl)-[3-(propyn-1'-yl)-phenyl]-amine; [6,7-bis-(2-methoxy-ethoxy)-quinazolin-4-yl]-(5-ethynyl-2-methyl-phenyl)-amine; [6,7-bis-(2-methoxy-ethoxy)-quinazolin-4-yl]-(3-ethynyl-4-fluoro-phenyl)-amine; [6,7-bis-(2-chloro-ethoxy)-quinazolin-4-yl]-(3-ethynyl-phenyl)-amine; [6-(2-chloro-ethoxy)-7-(2-methoxy-ethoxy)-quinazolin-4-yl]-(3-ethynyl-phenyl)-amine; [6,7-bis-(2-acetoxy-ethoxy)-quinazolin-4-yl]-(3-ethynyl-phenyl)-amine; 2-[4-(3-ethynyl-phenylamino)-7-(2-hydroxy-ethoxy)-quinazolin-6-yloxy]-ethanol; [6-(2-acetoxy-ethoxy)-7-(2-methoxy-ethoxy)-quinazolin-4-yl]-(3-ethynyl-phenyl)-amine; [7-(2-chloro-ethoxy)-6-(2-methoxy-ethoxy)-quinazolin-4-yl]-(3-ethynyl-phenyl)-amine; [7-(2-acetoxy-ethoxy)-6-(2-methoxy-ethoxy)-quinazolin-4-yl]-(3-ethynyl-phenyl)-amine; 2-[4-(3-ethynyl-phenylamino)-6-(2-hydroxy-ethoxy)-quinazolin-7-yloxy]-ethanol; 2-[4-(3-ethynyl-phenylamino)-7-(2-methoxy-ethoxy)-quinazolin-6-yloxy]-ethanol; 2-[4-(3-ethynyl-phenylamino)-6-(2-methoxy-ethoxy)-quinazolin-7-yloxy]-ethanol; [6-(2-acetoxy-ethoxy)-7-(2-methoxy-ethoxy)-quinazolin-4-yl]-(3-ethynyl-phenyl)-amine; (3-ethynyl-phenyl)-{6-(2-methoxy-ethoxy)-7-[2-(4-methyl-piperazin-1-yl)-ethoxy]-quinazolin-4-yl}-amine; (3-ethynyl-phenyl)-[7-(2-methoxy-ethoxy)-6-(2-morpholin-4-yl)-ethoxy)-quinazolin-4-yl]-amine; (6,7-diethoxyquinazolin-1-yl)-(3-ethynylphenyl)-amine; (6,7-dibutoxyquinazolin-1-yl)-(3-ethynylphenyl)-amine; (6,7-diisopropoxyquinazolin-1-yl)-(3-ethynylphenyl)-amine; (6,7-diethoxyquinazolin-1-yl)-(3-ethynyl-2-methyl-phenyl)-amine; [6,7-bis-(2-methoxy-ethoxy)-quinazolin-1-yl]-(3-ethynyl-2-methyl-phenyl)-amine; (3-ethynylphenyl)-[6-(2-hydroxy-ethoxy)-7-(2-methoxy-ethoxy)-quinazolin-1-yl]-amine; [6,7-bis-(2-hydroxy-ethoxy)-quinazolin-1-yl]-(3-ethynylphenyl)-amine; 2-[4-(3-ethynyl-phenylamino)-6-(2-methoxy-ethoxy)-quinazolin-7-yloxy]-ethanol; (6,7-dipropoxy-quinazolin-4-yl)-(3-ethynyl-phenyl)-amine; (6,7-diethoxy-quinazolin-4-yl)-(3-ethynyl-5-fluoro-phenyl)-amine; (6,7-diethoxy-quinazolin-4-yl)-(3-ethynyl-4-fluoro-phenyl)-amine; (6,7-diethoxy-quinazolin-4-yl)-(5-ethynyl-2-methyl-phenyl)-amine; (6,7-diethoxy-quinazolin-4-yl)-(3-ethynyl-4-methyl-phenyl)-amine; (6-aminomethyl-7-methoxy-quinazolin-4-yl)-(3-ethynyl-phenyl)-amine; (6-aminomethyl-7-methoxy-quinazolin-4-yl)-(3-ethynylphenyl)-amine; (6-aminocarbonylmethyl-7-methoxy-quinazolin-4-yl)-(3-ethynylphenyl)-amine; (6-aminocarbonylethyl-7-methoxy-quinazolin-4-yl)-(3-ethynylphenyl)-amine; (6-aminocarbonylmethyl-7-ethoxy-quinazolin-4-yl)-(3-ethynylphenyl)-amine; (6-aminocarbonylethyl-7-ethoxy-quinazolin-4-yl)-(3-ethynylphenyl)-amine; (6-aminocarbonylmethyl-7-isopropoxy-quinazolin-4-yl)-(3-ethynylphenyl)-amine; (6-aminocarbonylmethyl-7-propoxy-quinazolin-4-yl)-(3-ethynylphenyl)-amine; (6-aminocarbonylmethyl-7-methoxy-quinazolin-4-yl)-(3-ethynylphenyl)-amine; (6-aminocarbonylethyl-7-isopropoxy-quinazolin-4-yl)-(3-ethynylphenyl)-amine; and (6-aminocarbonylethyl-7-propoxy-quinazolin-4-yl)-(3-ethynylphenyl)-amine; (6,7-diethoxyquinazolin-1-yl)-(3-ethynylphenyl)-amine; (3-ethynylphenyl)-[6-(2-hydroxy-ethoxy)-7-(2-methoxy-ethoxy)-quinazolin-1-yl]-amine; [6,7-bis-(2-hydroxy-ethoxy)-quinazolin-1-yl]-(3-ethynylphenyl)-amine; [6,7-bis-(2-methoxy-ethoxy)-quinazolin-1-yl]-(3-ethynylphenyl)-amine; (6,7-dimethoxyquinazolin-1-yl)-(3-ethynylphenyl)-amine; (3-ethynylphenyl)-(6-methanesulfonylamino-quinazolin-1-yl)-amine; and (6-amino-quinazolin-1-yl)-(3-ethynylphenyl)-amine.

In a particular embodiment, the EGFR inhibitor of formula I is N-(3-ethynylphenyl)-6,7-bis(2-methoxyethoxy)-4-quinazolinamine. In a further embodiment, the EGFR inhibitor N-(3-ethynylphenyl)-6,7-bis(2-methoxyethoxy)-4-quinazolinamine is an HCl salt form. In another particular embodiment, the EGFR inhibitor N-(3-ethynylphenyl)-6,7-bis(2-methoxyethoxy)-4-quinazolinamine is in a substantially homogeneous crystalline polymorph form (described as polymorph B in WO 01/34,574) that exhibits an X-ray powder diffraction pattern having characteristic peaks expressed in degrees 2-theta at approximately 6.26, 12.48, 13.39, 16.96, 20.20, 21.10, 22.98, 24.46, 25.14 and 26.91. Such polymorph form of N-(3-ethynylphenyl)-6,7-bis(2-methoxyethoxy)-4-quinazolinamine is referred to as erlotinib (TARCEVA™, as well as OSI-774 and CP-358774), OSI Pharmaceuticals/Genentech. Erlotinib is known to bock the formation f EGFR-EGFR homodimers. Further examples of small molecule EGFR inhibitors include ZD1839 or Gefitinib (IRESSA™; Astra Zeneca); AG1478; AG1571 (SU 5271; Sugen); and EMD-7200.

The compounds of formula I, pharmaceutically acceptable salts and prodrugs thereof (hereafter the active compounds) may be prepared by any process known to be applicable to the preparation of chemically-related compounds. In general the active compounds may be made from the appropriately substituted quinazoline using the appropriately substituted amine as shown in the general scheme I disclosed in U.S. Pat. No. 5,747,498:

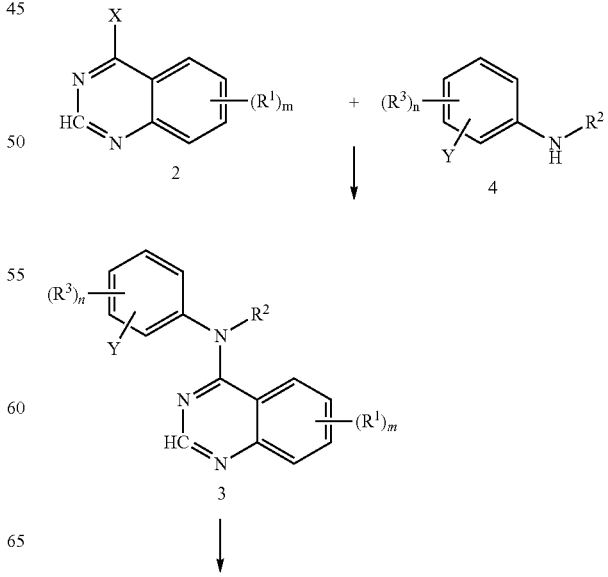

-continued

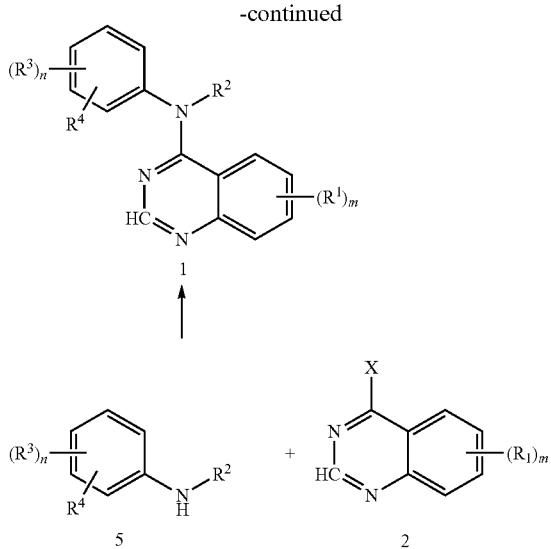

As shown in Scheme I the appropriate 4-substituted quinazoline 2 wherein X is a suitable displaceable leaving group such as halo, aryloxy, alkylsulfinyl, alkylsulfonyl such as trifluoromethanesulfonyloxy, arylsulfinyl, arylsulfonyl, siloxy, cyano, pyrazolo, triazolo or tetrazolo, preferably a 4-chloroquinazoline, is reacted with the appropriate amine or amine hydrochloride 4 or 5, wherein $R^4$ is as described above and Y is Br, I, or trifluoromethane-sulfonyloxy in a solvent such as a ($C_1$-$C_6$)alcohol, dimethylformamide (DMF), N-methylpyrrolidin-2-one, chloroform, acetonitrile, tetrahydrofuran (THF), 1-4 dioxane, pyridine or other aprotic solvent. The reaction may be effected in the presence of a base, preferably an alkali or alkaline earth metal carbonate or hydroxide or a tertiary amine base, such as pyridine, 2,6-lutidine, collidine, N-methyl-morpholine, triethylamine, 4-dimethylamino-pyridine or N,N-dimethylaniline. These bases are hereinafter refered to as suitable bases. The reaction mixture is maintained at a temperature from about ambient to about the reflux temperature of the solvent, preferably from about 35° C. to about reflux, until substantially no remaining 4-haloquinazoline can be detected, typically about 2 to about 24 hours. Preferably, the reaction is performed under an inert atmosphere such as dry nitrogen.

Generally the reactants are combined stoichiometrically. When an amine base is used for those compounds where a salt (typically the HCl salt) of an amine 4 or 5 is used, it is preferable to use excess amine base, generally an extra equivalent of amine base. (Alternatively, if an amine base is not used an excess of the amine 4 or 5 may be used).

For those compounds where a sterically hindered amine 4 (such as a 2-alkyl-3-ethynylaniline) or very reactive 4-haloquinazoline is used it is preferable to use t-butyl alcohol or a polar aprotic solvent such as DMF or N-methylpyrrolidin-2-one as the solvent.

Alternatively, a 4-substituted quinazoline 2 wherein X is hydroxyl or oxo (and the 2-nitrogen is hydrogenated) is reacted with carbon tetrachloride and an optionally substituted triarylphosphine which is optionally supported on an inert polymer (e.g. triphenylphosphine, polymer supported, Aldrich Cat. No. 36,645-5, which is a 2% divinylbenzene cross-linked polystyrene containing 3 mmol phosphorous per gram resin) in a solvent such as carbon tetrachloride, chloroform, dichloroethane, tetrahydrofuran, acetonitrile or other aprotic solvent or mixtures thereof. The reaction mixture is maintained at a temperature from about ambient to reflux, preferably from about 35° C. to reflux, for 2 to 24 hours. This mixture is reacted with the appropriate amine or amine hydrochloride 4 or 5 either directly or after removal of solvent, for example by vacuum evaporation, and addition of a suitable alternative solvent such as a ($C_1$-$C_6$) alcohol, DMF, N-methylpyrrolidin-2-one, pyridine or 1-4 dioxane. Then, the reaction mixture is maintained at a temperature from about ambient to the reflux temperature of the solvent preferably from about 35° C. to about reflux, until substantially complete formation of product is achieved, typically from about 2 to about 24 hours. Preferably the reaction is performed under an inert atmosphere such as dry nitrogen.

When compound 4, wherein Y is Br, I, or trifluoromethanesulfonyloxy, is used as starting material in the reaction with quinazoline 2, a compound of formula 3 is formed wherein $R^1$, $R^2$, $R^3$, and Y are as described above. Compound 3 is converted to compounds of formula 1 wherein $R^4$ is $R^{11}$ ethynyl, and $R^{11}$ is as defined above, by reaction with a suitable palladium reagent such as tetrakis(triphenylphosphine)palladium or bis(triphenylphosphine)palladium dichloride in the presence of a suitable Lewis acid such as cuprous chloride and a suitable alkyne such as trimethylsilylacetylene, propargyl alcohol or 3-(N,N-dimethylamino)-propyne in a solvent such as diethylamine or triethylamine. Compounds 3, wherein Y is $NH_2$, may be converted to compounds 1 wherein $R^4$ is azide by treatment of compound 3 with a diazotizing agent, such as an acid and a nitrite (e.g., acetic acid and $NaNO_2$) followed by treatment of the resulting product with an azide, such as $NaN_3$.

For the production of those compounds of Formula I wherein an $R^1$ is an amino or hydroxyamino group the reduction of the corresponding Formula I compound wherein $R^1$ is nitro is employed.

The reduction may conveniently be carried out by any of the many procedures known for such transformations. The reduction may be carried out, for example, by hydrogenation of the nitro compound in a reaction-inert solvent in the presence of a suitable metal catalyst such as palladium, platinum or nickel. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal with concentrated hydrochloric acid in a solvent such as a mixture of water and an alcohol, for example, methanol or ethanol, to a temperature in the range, for example, 50° to 150° C., conveniently at or near 70° C. Another suitable class of reducing agents are the alkali metal dithionites, such as sodium dithionite, which may be used in ($C_1$-$C_4$)alkanoic acids, ($C_1$-$C_6$)alkanols, water or mixtures thereof.

For the production of those compounds of Formula I wherein $R^2$ or $R^3$ incorporates a primary or secondary amino moiety (other than the amino group intended to react with the quinazoline), such free amino group is preferably protected prior to the above described reaction followed by deprotection, subsequent to the above described reaction with 4-(substituted)quinazoline 2.

Several well known nitrogen protecting groups can be used. Such groups include ($C_1$-$C_6$)alkoxycarbonyl, optionally substituted benzyloxycarbonyl, aryloxycarbonyl, trityl, vinyloxycarbonyl, O-nitrophenylsulfonyl, diphenylphosphinyl, p-toluenesulfonyl, and benzyl. The addition of the nitrogen protecting group may be carried out in a chlorinated hydrocarbon solvent such as methylene chloride or 1,2-dichloroethane, or an ethereal solvent such as glyme, diglyme or THF, in the presence or absence of a tertiary amine base such as triethylamine, diisopropylethylamine or pyridine, preferably triethylamine, at a temperature from about 0° C. to about 50° C., preferably about ambient temperature. Alternatively, the protecting groups are conveniently attached using Schotten-Baumann conditions.

Subsequent to the above described coupling reaction, of compounds 2 and 5, the protecting group may be removed by deprotecting methods known to those skilled in the art such as treatment with trifluoroacetic acid in methylene chloride for the tert-butoxycarbonyl protected products.

For a description of protecting groups and their use, see T. W. Greene and P. G. M. Wuts, "Protective Groups in Organic Synthesis" Second Ed., John Wiley & Sons, New York, 1991.

For the production of compounds of Formula I wherein $R^1$ or $R^2$ is hydroxy, cleavage of a Formula I compound wherein $R^1$ or $R^2$ is $(C_1-C_4)$alkoxy is preferred.

The cleavage reaction may conveniently be carried out by any of the many procedures known for such a transformation. Treatment of the protected formula I derivative with molten pyridine hydrochloride (20-30 eq.) at 150° to 175° C. may be employed for O-dealkylations. Alternatively, the cleavage reaction may be carried out, for example, by treatment of the protected quinazoline derivative with an alkali metal $(C_1-C_4)$ alkylsulphide, such as sodium ethanethiolate or by treatment with an alkali metal diarylphosphide such as lithium diphenylphosphide. The cleavage reaction may also, conveniently, be carried out by treatment of the protected quinazoline derivative with a boron or aluminum trihalide such as boron tribromide. Such reactions are preferably carried out in the presence of a reaction-inert solvent at a suitable temperature.

Compounds of formula I, wherein $R^1$ or $R^2$ is a $(C_1-C_4)$ alkylsulphinyl or $(C_1-C_4)$alkylsulphonyl group are preferably prepared by oxidation of a formula I compound wherein $R^1$ or $R^2$ is a $(C_1-C_4)$alkylsulfanyl group. Suitable oxidizing agents are known in the art for the oxidation of sulfanyl to sulphinyl and/or sulphonyl, e.g., hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible using the stoichiometric amount of oxidizing agent in order to reduce the risk of over oxidation and damage to other functional groups. In general, the reaction is carried out in a suitable solvent such as methylene chloride, chloroform, acetone, tetrahydrofuran or tert-butyl methyl ether and at a temperature from about −25° to 50° C., preferably at or near ambient temperature, i.e., in the range of 15° to 35° C. When a compound carrying a sulphinyl group is desired a milder oxidizing agents should be used such as sodium or potassium metaperiodate, conveniently in a polar solvent such as acetic acid or ethanol. The compounds of formula I containing a $(C_1-C_4)$alkylsulphonyl group may be obtained by oxidation of the corresponding $(C_1-C_4)$alkylsulphinyl compound as well as of the corresponding $(C_1-C_4)$ alkylsulfanyl compound.

Compounds of formula I wherein $R^1$ is optionally substituted $(C_2-C_4)$alkanoylamino, ureido, 3-phenylureido, benzamido or sulfonamido can be prepared by acylation or sulfonylation of a corresponding compound wherein $R^1$ is amino. Suitable acylating agents are any agents known in the art for the acylation of amino to acylamino, for example, acyl halides, e.g., a $(C_2-C_4)$alkanoyl chloride or bromide or a benzoyl chloride or bromide, alkanoic acid anhydrides or mixed anhydrides (e.g., acetic anhydride or the mixed anhydride formed by the reaction of an alkanoic acid and a $(C_1-C_4)$alkoxycarbonyl halide, for example $(C_1-C_4)$alkoxycarbonyl chloride, in the presence of a suitable base. For the production of those compounds of Formula I wherein $R^1$ is ureido or 3-phenylureido, a suitable acylating agent is, for example, a cyanate, e.g., an alkali metal cyanate such as sodium cyanate, or an isocyanate such as phenyl isocyanate. N-sulfonylations may be carried out with suitable sulfonyl halides or sulfonylanhydrides in the presence of a tertiary amine base. In general the acylation or sulfonylation is carried out in a reaction-inert solvent and at a temperature in the range of about −30° to 120° C., conveniently at or near ambient temperature.

Compounds of Formula I wherein $R^1$ is $(C_1-C_4)$alkoxy or substituted $(C_1-C_4)$alkoxy or $R^1$ is $(C_1-C_4)$alkylamino or substituted mono-N- or di-N,N-$(C_1-C_4)$alkylamino, are prepared by the alkylation, preferably in the presence of a suitable base, of a corresponding compound wherein $R^1$ is hydroxy or amino, respectively. Suitable alkylating agents include alkyl or substituted alkyl halides, for example, an optionally substituted $(C_1-C_4)$alkyl chloride, bromide or iodide, in the presence of a suitable base in a reaction-inert solvent and at a temperature in the range of about 10° to 140° C., conveniently at or near ambient temperature.

For the production of those compounds of Formula I wherein $R^1$ is an amino-, oxy- or cyano-substituted $(C_1-C_4)$ alkyl substituent, a corresponding compound wherein $R^1$ is a $(C_1-C_4)$alkyl substituent bearing a group which is displacable by an amino-, alkoxy-, or cyano group is reacted with an appropriate amine, alcohol or cyanide, preferably in the presence of a suitable base. The reaction is preferably carried out in a reaction-inert solvent or diluent and at a temperature in the range of about 10° to 100° C., preferably at or near ambient temperature.

Compounds of Formula I, wherein $R^1$ is a carboxy substituent or a substituent which includes a carboxy group are prepared by hydrolysis of a corresponding compound wherein $R^1$ is a $(C_1-C_4)$alkoxycarbonyl substituent or a substituent which includes a $(C_1-C_4)$alkoxycarbonyl group. The hydrolysis may conveniently be performed, for example, under basic conditions, e.g., in the presence of alkali metal hydroxide.

Compounds of Formula I wherein $R^1$ is amino, $(C_1-C_4)$ alkylamino, di-[$(C_1-C_4)$alkyl]amino, pyrrolidin-1-yl, piperidino, morpholino, piperazin-1-yl, 4-$(C_1-C_4)$alkylpiperazin-1-yl or $(C_1-C_4)$alkysulfanyl, may be prepared by the reaction, in the presence of a suitable base, of a corresponding compound wherein $R^1$ is an amine or thiol displaceable group with an appropriate amine or thiol. The reaction is preferably carried out in a reaction-inert solvent or diluent and at a temperature in the range of about 10° to 180° C., conveniently in the range 100° to 150° C.

Compounds of Formula I wherein $R^1$ is 2-oxopyrrolidin-1-yl or 2-oxopiperidin-1-yl are prepared by the cyclisation, in the presence of a suitable base, of a corresponding compound wherein $R^1$ is a halo-$(C_2-C_4)$alkanoylamino group. The reaction is preferably carried out in a reaction-inert solvent or diluent and at a temperature in the range of about 10° to 100° C., conveniently at or near ambient temperature.

For the production of compounds of Formula I in which $R^1$ is carbamoyl, substituted carbamoyl, alkanoyloxy or substituted alkanoyloxy, the carbamoylation or acylation of a corresponding compound wherein $R^1$ is hydroxy is convenient.

Suitable acylating agents known in the art for acylation of hydroxyaryl moieties to alkanoyloxyaryl groups include, for example, $(C_2-C_4)$alkanoyl halides, $(C_2-C_4)$alkanoyl anhydrides and mixed anhydrides as described above, and suitable substituted derivatives thereof may be employed, typically in the presence of a suitable base. Alternatively, $(C_2-C_4)$alkanoic acids or suitably substituted derivatives thereof may be coupled with a Formula I compound wherein R¹ is hydroxy with the aid of a condensing agent such as a carbodiimide. For the production of those compounds of Formula I in which R¹ is carbamoyl or substituted carbamoyl, suitable carbamoylating agents are, for example, cyanates or alkyl or arylisocyanates, typically in the presence of a suitable base. Alternatively, suitable intermediates such as the chloroformate or carbonylimidazolyl derivative of a compound of Formula I in which R¹ is hydroxy may be generated, for example, by treatment of said derivative with phosgene (or a phosgene equivalent) or carbonyldiimidazole. The resulting intermediate may then be reacted with an appropriate amine or substituted amine to produce the desired carbamoyl derivatives.

Compounds of formula I wherein R¹ is aminocarbonyl or a substituted aminocarbonyl can be prepared by the aminolysis of a suitable intermediate in which R¹ is carboxy.

The activation and coupling of formula I compounds wherein R¹ is carboxy may be performed by a variety of methods known to those skilled in the art. Suitable methods include activation of the carboxyl as an acid halide, azide, symmetric or mixed anhydride, or active ester of appropriate reactivity for coupling with the desired amine. Examples of such types of intermediates and their production and use in couplings with amines may be found extensively in the literature; for example M. Bodansky and A. Bodansky, "The Practice of Peptide Synthesis", Springer-Verlag, New York, 1984. The resulting formula I compounds may be isolated and purified by standard methods, such as solvent removal and recrystallization or chromatography.

The starting materials for the described reaction scheme I (e.g., amines, quinazolines and amine protecting groups) are readily available or can be easily synthesized by those skilled in the art using conventional methods of organic synthesis. For example, the preparation of 2,3-dihydro-1,4-benzoxazine derivatives are described in R. C. Elderfield, W. H. Todd, S. Gerber, Ch. 12 in "Heterocyclic Compounds", Vol. 6, R. C. Elderfield ed., John Wiley and Sons, Inc., N.Y., 1957. Substituted 2,3-dihydrobenzothiazinyl compounds are described by R. C. Elderfield and E. E. Harris in Ch. 13 of Volume 6 of the Elderfield "Heterocyclic Compounds" book.

In another particular embodiment, the EGFR inhibitor has a general formula II as described in U.S. Pat. No. 5,457,105: Iressa broad

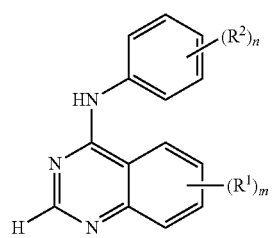

II wherein:
m is 1, 2 or 3 and
each R¹ is independently 6-hydroxy, 7-hydroxy, amino, carboxy, carbamoyl, ureido, (1-4C)alkoxycarbonyl, N-(1-4C)alkylcarbamoyl, N,N-di-[(1-4C)alkyl]carbamoyl, hydroxyamino, (1-4C)alkoxyamino, (2-4C)alkanoyloxyamino, trifluoromethoxy, (1-4C)alkyl, 6-(1-4C)alkoxy, 7-(1-4C)alkoxy, (1-3C)alkylenedioxy, (1-4C)alkylamino, di-1[(1-4C)alkyl]amino, pyrrolidin-1-yl, piperidino, morpholino, piperazin-1-yl, 4-(1-4C)alkylpiperazin-1-yl, (1-4C) alkylthio, (1-4C)alkylsulphinyl, (1-4C)alkylsulphonyl, bromomethyl, dibromomethyl, hydroxy-(1-4C)alkyl, (2-4C) alkanoyloxy-(1-4C)alkyl, (1-4C)alkoxy-(1-4C)alkyl, carboxy-(1-4C)alkyl, (1-4C)alkoxycarbonyl-(1-4C)alkyl, carbamoyl-(1-4C)alkyl, N-(1-4C)alkylcarbamoyl-(1-4C) alkyl, N,N-di-[(1-4C)alkyl]carbamoyl-(1-4C)alkyl, amino-(1-4C)alkyl, (1-4C)alkylamino-(1-4C)alkyl, di-[(1-4C) alkyl]amino-(1-4C)alkyl, piperidino-(1-4C)alkyl, morpholino-(1-4C)alkyl, piperazin-1-yl-(1-4C) alkyl, 4-(1-4C)alkylpiperazin-1-yl-(1-4C) alkyl, hydroxy-(2-4C) alkoxy-(1-4C) alkyl, (1-4C)alkoxy-(2-4C)alkoxy-(1-4C) alkyl, hydroxy-(2-4C)alkylamino-(1-4C)alkyl, (1-4C) alkoxy-(2-4C)alkylamino-(1-4C)alkyl, (1-4C)alkylthio-(1-4C)alkyl, hydroxy-(2-4C)alkylthio-(1-4C)alkyl, (1-4C) alkoxy-(2-4C)alkylthio-(1-4C)alkyl, phenoxy-(1-4C)alkyl, anilino-(1-4C)alkyl, phenylthio-(1-4C)alkyl, cyano-(1-4C) alkyl, halogeno-(2-4C)alkoxy, hydroxy-(2-4C)alkoxy, (2-4C)alkanoyloxy-(2-4C)alkoxy, (1-4C)alkoxy-(2-4C) alkoxy, carboxy-(1-4C)alkoxy, (1-4C)alkoxycarbonyl-(1-4C)alkoxy, carbamoyl-(1-4C)alkoxy, N-(1-4C) alkylcarbamoyl-(1-4C)alkoxy, N,N-di-[(1-4C)alkyl]carbamoyl-(1-4C) alkoxy, amino-(2-4C)alkoxy, (1-4C)alkylamino-(2-4C) alkoxy, di-[(1-4C)alkyl]amino-(2-4C)alkoxy, (2-4C) alkanoyloxy, hydroxy-(2-4C)alkanoyloxy, (1-4C)alkoxy-(2-4C)alkanoyloxy, phenyl-(1-4C)alkoxy, phenoxy-(2-4C) alkoxy, anilino-(2-4C)alkoxy, phenylthio-(2-4C)alkoxy, piperidino-(2-4C)alkoxy, morpholino-(2-4C)alkoxy, piperazin-1-yl-(2-4C)alkoxy, 4-(1-4C)alkylpiperazin-1-yl-(2-4C) alkoxy, halogeno-(2-4C)alkylamino, hydroxy-(2-4C)alkylamino, (2-4C)alkanoyloxy-(2-4C)alkylamino, (1-4C) alkoxy-(2-4C)alkylamino, carboxy-(1-4C)alkylamino, (1-4C)alkoxycarbonyl-(1-4C)alkylamino, carbamoyl-(1-4C) alkylamino, N-(1-4C)alkylcarbamoyl-(1-4C)alkylamino, N,N-di-[(1-4C)alkyl]carbamoyl-(1-4C)alkylamino, amino-(2-4C)alkylamino, (1-4C)alkylamino-(2-4C)alkylamino, di-[(1-4C)alkyl]amino-(2-4C)alkylamino, phenyl-(1-4C)alkylamino, phenoxy-(2-4C)alkylamino, anilino-(2-4C) alkylamino, phenylthio-(2-4C)alkylamino, (2-4C) alkanoylamino, (1-4C)alkoxycarbonylamino, (1-4C) alkylsulphonylamino, benzamido, benzenesulphonamido, 3-phenylureido, 2-oxopyrrolidin-1-yl, 2,5-dioxopyrrolidin-1-yl, halogeno-(2-4C)alkanoylamino, hydroxy-(2-4C)alkanoylamino, (1-4C)alkoxy-(2-4C)alkanoylamino, carboxy-(2-4C)alkanoylamino, (1-4C)alkoxycarbonyl-(2-4C) alkanoylamino, carbamoyl-(2-4C)alkanoylamino, N-(1-4C) alkylcarbamoyl-(2-4C)alkanoylamino, N,N-di-[(1-4C)alkyl] carbamoyl-(2-4C)alkanoylamino, amino-(2-4C) alkanoylamino, (1-4C)alkylamino-(2-4C)alkanoylamino or di-[(1-4C)alkyl]amino-(2-4C)alkanoylamino, and wherein said benzamido or benzenesulphonamido substituent or any anilino, phenoxy or phenyl group in a R¹ substituent may optionally bear one or two halogeno, (1-4C)alkyl or (1-4C) alkoxy substituents;

n is 1 or 2 and each R² is independently hydrogen, hydroxy, halogeno, trifluoromethyl, amino, nitro, cyano, (1-4C)alkyl, (1-4C) alkoxy, (1-4C)alkylamino, di-[(1-4C)alkyl]amino, (1-4C) alkylthio, (1-4C)alkylsulphinyl or (1-4C)alkylsulphonyl; or a pharmaceutically-acceptable salt thereof; except that 4-(4'-hydroxyanilino)-6-methoxyquinazoline, 4-(4,-hydroxyanilino)-6,7-methylenedioxyquinazoline, 6-amino-4-(4'-aminoanilino)quinazoline, 4-anilino-6-methylquinazoline or the hydrochloride salt thereof and 4-anilino-6,7-dimethoxyquinazoline or the hydrochloride salt thereof are excluded.

In a particular embodiment, the EGFR inhibitor is a compound according to formula II selected from the group consisting of:

4-(3'-chloro-4'-fluoroanilino)-6,7-dimethoxyquinazoline; 4-(3',4'-dichloroanilino)-6,7-dimethoxyquinazoline; 6,7-dimethoxy-4-(3'-nitroanilino)-quinazoline; 6,7-diethoxy-4-(3'-methylanilino)-quinazoline; 6-methoxy-4-(3'-methylanilino)-quinazoline; 4-(3'-chloroanilino)-6-methoxyquinazoline; 6,7-ethylenedioxy-4-(3'-methylanilino)-quinazoline; 6-amino-7-methoxy-4-(3'-methylanilino)-quinazoline; 4-(3'-methylanilino)-6-ureidoquinazoline; 6-(2-methoxyethoxymethyl)-4-(3'-methylanilino)-quinazoline; 6,7-di-(2-methoxyethoxy)-4-(3'-methylanilino)-quinazoline; 6-dimethylamino-4-(3'-methylanilino)quinazoline; 6-benzamido-4-(3'-methylanilino)quinazoline; 6,7-dimethoxy-4-(3'-trifluoromethylanilino)-quinazoline; 6-hydroxy-7-methoxy-4-(3'-methylanilino)-quinazoline; 7-hydroxy-6-methoxy-4-(3'-methylanilino)-quinazoline; 7-amino-4-(3'-methylanilino)-quinazoline; 6-amino-4-(3'-methylanilino)quinazoline; 6-amino-4-(3'-chloroanilino)-quinazoline; 6-acetamido-4-(3'-methylanilino)-quinazoline; 6-(2-methoxyethylamino)-4-(3'-methylanilino)-quinazoline; 7-(2-methoxyacetamido)-4-(3'-methylanilino)-quinazoline; 7-(2-hydroxyethoxy)-6-methoxy-4-(3'-methylanilino)-quinazoline; 7-(2-methoxyethoxy)-6-methoxy-4-(3'-methylanilino)-quinazoline; 6-amino-4-(3'-methylanilino)-quinazoline.

A quinazoline derivative of the formula II, or a pharmaceutically-acceptable salt thereof, may be prepared by any process known to be applicable to the preparation of chemically-related compounds. A suitable process is, for example, illustrated by that used in U.S. Pat. No. 4,322,420. Necessary starting materials may be commercially available or obtained by standard procedures of organic chemistry.

(a) The reaction, conveniently in the presence of a suitable base, of a quinazoline (i), wherein Z is a displaceable group, with an aniline (ii).

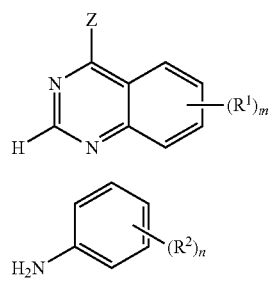

A suitable displaceable group Z is, for example, a halogeno, alkoxy, aryloxy or sulphonyloxy group, for example a chloro, bromo, methoxy, phenoxy, methanesulphonyloxy or toluene-p-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali or alkaline earth metal carbonate or hydroxide, for example sodium carbonate, potassium carbonate, calcium carbonate, sodium hydroxide or potassium hydroxide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The quinazoline derivative of the formula II may be obtained from this process in the form of the free base or alternatively it may be obtained in the form of a salt with the acid of the formula H-Z wherein Z has the meaning defined hereinbefore. When it is desired to obtain the free base from the salt, the salt may be treated with a suitable base as defined hereinbefore using a conventional procedure.

(b) For the production of those compounds of the formula II wherein $R^1$ or $R^2$ is hydroxy, the cleavage of a quinazoline derivative of the formula II wherein $R^1$ or $R^2$ is (1-4C)alkoxy.

The cleavage reaction may conveniently be carried out by any of the many procedures known for such a transformation. The reaction may be carried out, for example, by treatment of the quinazoline derivative with an alkali metal (1-4C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide. Such reactions are preferably carried out in the presence of a suitable inert solvent or diluent as defined hereinbefore and at a suitable temperature.

(c) For the production of those compounds of the formula II wherein $R^1$ or $R^2$ is a (1-4C)alkylsulphinyl or (1-4C)alkylsulphonyl group, the oxidation of a quinazoline derivative of the formula II wherein $R^1$ or $R^2$ is a (1-4C)alkylthio group.

A suitable oxidizing agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carrried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, −25° to 50° C., conveniently at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula II containing a (1-4C)alkylsulphonyl group is required, it may be obtained by oxidation of the corresponding (1-4C)alkylsulphinyl compound as well as of the corresponding (1-4C)alkylthio compound.

(d) For the production of those compounds of the formula II wherein $R^1$ is amino, the reduction of a quinazoline derivative of the formula I wherein $R^1$ is nitro.

The reduction may conveniently be carried out by any of the many procedures known for such a transformation. The reduction may be carrried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

(e) For the production of those compounds of the formula II wherein $R^1$ is (2-4C)alkanoylamino or substituted (2-4C) alkanoylamino, ureido, 3-phenylureido or benzamido, or $R^2$ is acetamido or benzamido, the acylation of a quinazoline derivative of the formula II wherein $R^1$ or $R^2$ is amino.

A suitable acylating agent is, for example, any agent known in the art for the acylation of amino to acylamino, for example an acyl halide, for example a (2-4C)alkanoyl chloride or bromide or a benzoyl chloride or bromide, conveniently in the presence of a suitable base, as defined hereinbefore, an alkanoic acid anhydride or mixed anhydride, for example a (2-4C)alkanoic acid anhydride such as acetic anhydride or the mixed anhydride formed by the reaction of an alkanoic acid and a (1-4C)alkoxycarbonyl halide, for example a (1-4C) alkoxycarbonyl chloride, in the presence of a suitable base as defined hereinbefore. For the production of those compounds of the formula II wherein $R^1$ is ureido or 3-phenylureido, a suitable acylating agent is, for example, a cyanate, for example an alkali metal cyanate such as sodium cyanate or, for example, an isocyanate such as phenyl isocyanate. In general the acylation is carried out in a suitable inert solvent or diluent as defined hereinbefore and at a temperature, in the range, for example, −30° to 120° C., conveniently at or near ambient temperature.

(f) For the production of those compounds of the formula II wherein $R^1$ is (1-4C)alkoxy or substituted (1-4C)alkoxy or $R^1$ is (1-4C)alkylamino or substituted (1-4C)alkylamino, the alkylation, preferably in the presence of a suitable base as defined hereinbefore, of a quinazoline derivative of the formula II wherein $R^1$ is hydroxy or amino as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-4C)alkyl chloride, bromide or iodide or a substituted (1-4C)alkyl chloride, bromide or iodide, in the presence of a suitable base as defined hereinbefore, in a suitable inert solvent or diluent as defined hereinbefore and at a temperature in the range, for example, 10° to 140° C., conveniently at or near ambient temperature.

(g) For the production of those compounds of the formula II wherein $R^1$ is a carboxy substituent or a substituent which includes a carboxy group, the hydrolysis of a quinazoline derivative of the formula II wherein $R^1$ is a (1-4C)alkoxycarbonyl substituent or a substituent which includes a (1-4C) alkoxycarbonyl group.

The hydrolysis may conveniently be performed, for example, under basic conditions.

(h) For the production of those compounds of the formula II wherein $R^1$ is an amino-, oxy-, thio- or cyano-substituted (1-4C)alkyl substituent, the reaction, preferably in the presence of a suitable base as defined hereinbefore, of a quinazoline derivative of the formula II wherein $R^1$ is a (1-4C)alkyl substituent bearing a displaceable group as defined hereinbefore with an appropriate amine, alcohol, thiol or cyanide.

The reaction is preferably carried out in a suitable inert solvent or diluent as defined hereinbefore and at a temperature in the range, for example, 10° to 100° C., conveniently at or near ambient temperature.

When a pharmaceutically-acceptable salt of a quinazoline derivative of the formula II is required, it may be obtained, for example, by reaction of said compound with, for example, a suitable acid using a conventional procedure.

In a particular embodiment, the EGFR inhibitor is a compound according to formula II' as disclosed in U.S. Pat. No. 5,770,599: Iressa subgenus

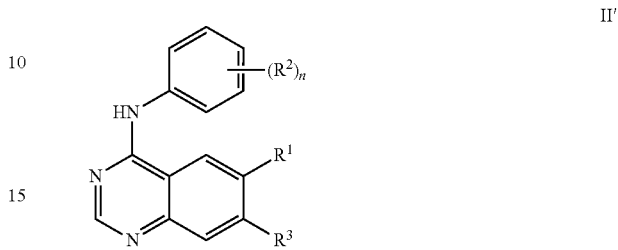

wherein n is 1, 2 or 3;
each $R^2$ is independently halogeno or trifluoromethyl
$R^3$ is (1-4C)alkoxy; and
$R^1$ is di-[(1-4C)alkyl]amino-(2-4C)alkoxy, pyrrolidin-1-yl-(2-4C)alkoxy, piperidino-(2-4C)alkoxy, morpholino-(2-4C) alkoxy, piperazin-1-yl-(2-4C)alkoxy, 4-(1-4C)alkylpiperazin-1-yl-(2-4C)alkoxy, imidazol-1-yl-(2-4C)alkoxy, di-[(1-4C)alkoxy-(2-4C)alkyl]amino-(2-4C)alkoxy, thiamorpholino-(2-4C)alkoxy, 1-oxothiamorpholino-(2-4C) alkoxy or 1,1-dioxothiamorpholino-(2-4C)alkoxy, and wherein any of the above mentioned $R^1$ substituents comprising a $CH_2$ (methylene) group which is not attached to a N or O atom optionally bears on said $CH_2$ group a hydroxy substituent;
or a pharmaceutically-acceptable salt thereof.

In a particular embodiment, the EGFR inhibitor is a compound according to formula II' selected from the group consisting of:
4-(3'-chloro-4'-fluoroanilino)-7-methoxy-6-(2-pyrrolidin-1-ylethoxy)-quinazoline; 4-(3'-chloro-4'-fluoroanilino)-7-methoxy-6-(2-morpholinoethoxy)-quinazoline; 4-(3'-chloro-4'-fluoroanilino)-6-(3-diethylaminopropoxy)-7-methoxyquinazoline; 4-(3'-chloro-4'-fluoroanilino)-7-methoxy-6-(3-pyrrolidin-1-ylpropoxy)-quinazoline; 4-(3'-chloro-4'-fluoroanilino)-6-(3-dimethylaminopropoxy)-7-methoxyquinazoline; 4-(3',4'-difluoroanilino)-7-methoxy-6-(3-morpholinopropoxy)-quinazoline; 4-(3'-chloro-4'-fluoroanilino)-7-methoxy-6-(3-piperidinopropoxy)-quinazoline; 4-(3'-chloro-4'-fluoroanilino)-7-methoxy-6-(3-morpholinopropoxy)-quinazoline; 4-(3'-chloro-4'-fluoroanilino)-6-(2-dimethylaminoethoxy)-7-methoxyquinazoline; 4-(2',4'-difluoroanilino)-6-(3-dimethylaminopropoxy)-7-methoxyquinazoline; 4-(2',4'-difluoroanilino)-7-methoxy-6-(3-morpholinopropoxy)-quinazoline; 4-(3'-chloro-4'-fluoroanilino)-6-(2-imidazol-1-ylethoxy)-7-methoxyquinazoline; 4-(3'-chloro-4'-fluoroanilino)-6-(3-imidazol-1-ylpropoxy)-7-methoxyquinazoline; 4-(3'-chloro-4'-fluoroanilino)-6-(2-dimethylaminoethoxy)-7-methoxyquinazoline; 4-(2',4'-difluoroanilino)-6-(3-dimethylaminopropoxy)-7-methoxyquinazoline; 4-(2',4'-difluoroanilino)-7-methoxy-6-(3-morpholinopropoxy)-quinazoline; 4-(3'-chloro-4'-fluoroanilino)-6-(2-imidazol-1-ylethoxy)-7-methoxyquinazoline; and 4-(3'-chloro-4'-fluoroanilino)-6-(3-imidazol-1-ylpropoxy)-7-methoxyquinazoline.

In a particular embodiment, the EGFR inhibitor is a compound according to formula II' that is 4-(3'-chloro-4'-fluoroanilino)-7-methoxy-6-(3-morpholinopropoxy)-quinazoline, alternatively referred to as ZD 1839, gefitinib and Iressa™.

A quinazoline derivative of the formula II', or a pharmaceutically-acceptable salt thereof, may be prepared by any process known to be applicable to the preparation of chemically-related compounds. Suitable processes include, for example, those illustrated in U.S. Pat. No. 5,616,582, U.S. Pat. No. 5,580,870, U.S. Pat. No. 5,475,001 and U.S. Pat. No. 5,569,658. Unless otherwise stated, n, R 2, $R^3$ and $R^1$ have any of the meanings defined hereinbefore for a quinazoline derivative of the formula II'. Necessary starting materials may be commercially available or obtained by standard procedures of organic chemistry.

(a) The reaction, conveniently in the presence of a suitable base, of a quinazoline (iii) wherein Z is a displaceable group, with an aniline (iv)

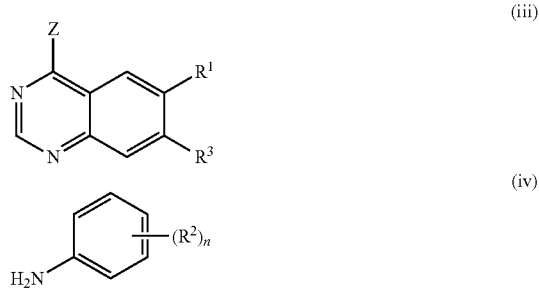

A suitable displaceable group Z is, for example, a halogeno, alkoxy, aryloxy or sulphonyloxy group, for example a chloro, bromo, methoxy, phenoxy, methanesulphonyloxy or toluene-4-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The quinazoline derivative of the formula II' may be obtained from this process in the form of the free base or alternatively it may be obtained in the form of a salt with the acid of the formula H-Z wherein Z has the meaning defined hereinbefore. When it is desired to obtain the free base from the salt, the salt may be treated with a suitable base as defined hereinbefore using a conventional procedure.

(b) For the production of those compounds of the formula II' wherein $R^1$ is an amino-substituted (2-4C)alkoxy group, the alkylation, conveniently in the presence of a suitable base as defined hereinbefore, of a quinazoline derivative of the formula II' wherein $R^1$ is a hydroxy group.

A suitable alkylating agent is, for example, any agent known in the art for the alkylation of hydroxy to amino-substituted alkoxy, for example an amino-substituted alkyl halide, for example an amino-substituted (2-4C)alkyl chloride, bromide or iodide, in the presence of a suitable base as defined hereinbefore, in a suitable inert solvent or diluent as defined hereinbefore and at a temperature in the range, for example, 10° to 140° C., conveniently at or near 80° C.

(c) For the production of those compounds of the formula II' wherein $R^1$ is an amino-substituted (2-4C)alkoxy group, the reaction, conveniently in the presence of a suitable base as defined hereinbefore, of a compound of the formula II' wherein $R^1$ is a hydroxy-(2-4C)alkoxy group, or a reactive derivative thereof, with an appropriate amine.

A suitable reactive derivative of a compound of the formula II' wherein $R^1$ is a hydroxy-(2-4C)alkoxy group is, for example, a halogeno- or sulphonyloxy-(2-4C)alkoxy group such as a bromo- or methanesulphonyloxy-(2-4C)alkoxy group.

The reaction is preferably carried out in the presence of a suitable inert solvent or diluent as defined hereinbefore and at a temperature in the range, for example, 10° to 150° C., conveniently at or near 50° C.

(d) For the production of those compounds of the formula II' wherein $R^1$ is a hydroxy-amino-(2-4C)alkoxy group, the reaction of a compound of the formula II' wherein $R^1$ is a 2,3-epoxypropoxy or 3,4-epoxybutoxy group with an appropriate amine.

The reaction is preferably carried out in the presence of a suitable inert solvent or diluent as defined hereinbefore and at a temperature in the range, for example, 10° to 150° C., conveniently at or near 70° C.

When a pharmaceutically-acceptable salt of a quinazoline derivative of the formula II' is required, for example a mono- or di-acid-addition salt of a quinazoline derivative of the formula II', it may be obtained, for example, by reaction of said compound with, for example, a suitable acid using a conventional procedure.

In another particular embodiment, the EGFR inhibitor is a small molecule which has a general formula III (see, US20020147205):

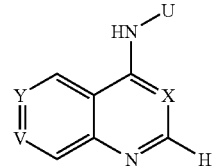

or a salt or solvate thereof;
wherein X is N or CH;
Y is $CR^1$ and V is N;
or Y is N and V is $CR^1$;
or Y is $CR^1$ and V is $CR^2$
or Y is $CR^2$ and V is $CR^1$;
$R^1$ represents a group $CH_3SO_2$ $CH_2CH_2NHCH_2$—Ar—, wherein Ar is selected from phenyl, furan, thiophene, pyrrole and thiazole, each of which may optionally be substituted by one or two halo, $C_{1-4}$ alkyl or $C_{1-4}$ alkoxy groups;
$R^2$ is selected from the group comprising hydrogen, halo, hydroxy, $C_{1-4}$ alkyl, $C_{1-4}$ alkoxy, $C_{1-4}$ alkylamino and di[$C_{1-4}$ alkyl]amino;

U represents a phenyl, pyridyl, 3H-imidazolyl, indolyl, isoindolyl, indolinyl, isoindolinyl, 1H-indazolyl, 2,3-dihydro-1H-indazolyl, 1H-benzimidazolyl, 2,3-dihydro-1H-benzimidazolyl or 1H-benzotriazolyl group, substituted by an $R^3$ group and optionally substituted by at least one independently selected $R^4$ group;

$R^3$ is selected from a group comprising benzyl, halo-, dihalo- and trihalobenzyl, benzoyl, pyridylmethyl, pyridylmethoxy, phenoxy, benzyloxy, halo-, dihalo- and trihalobenzyloxy and benzenesulphonyl;

or $R^3$ represents trihalomethylbenzyl or trihalomethylbenzyloxy;

or $R^3$ represents a group of formula

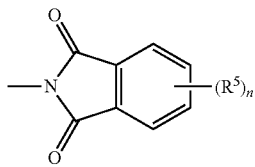

wherein each $R^5$ is independently selected from halogen, $C_{1-4}$ alkyl and $C_{1-4}$ alkoxy; and n is 0 to 3;

each $R^4$ is independently hydroxy, halogen, $C_{1-4}$ alkyl, $C_{2-4}$ alkenyl, $C_{2-4}$ alkynyl, $C_{1-4}$ alkoxy, amino, $C_{1-4}$ alkylamino, di[$C_{1-4}$ alkyl]amino, $C_{1-4}$ alkylthio, $C_{1-4}$ alkylsulphinyl, $C_{1-4}$ alkylsulphonyl, $C_{1-4}$ alkylcarbonyl, carboxy, carbamoyl, $C_{1-4}$ alkoxycarbonyl, $C_{1-4}$ alkanoylamino, N-($C_{1-4}$ alkyl)carbamoyl, N,N-di($C_{1-4}$ alkyl)carbamoyl, cyano, nitro and trifluoromethyl.

In a particular embodiment, EGFR inhibitors are compound of formula III selected from the group consisting of:

4-(4-Fluorobenzyloxy)-phenyl)-(6-(5-((2-methanesulphonyl-ethylamino)methyl)-furan-2-yl)-pyrido[3,4-d]pyrimidin-4-yl)-amine;

(4-(3-Fluorobenzyloxy)-phenyl)-(6-(5-((2-methanesulphonyl-ethylamino)methyl)-furan-2-yl)-pyrido[3,4-d]pyrimidin-4-yl)-amine;

(4-Benzenesulphonyl-phenyl)-(6-(5-((2-methanesulphonyl-ethylamino)-methyl)-furan-2-yl)-pyrido[3,4-d]pyrimidin-4-yl)-amine;

(4-Benzyloxy-phenyl)-(6-(3-((2-methanesulphonyl-ethylamino)-methyl)-phenyl)-pyrido[3,4-d]pyrimidin-4-yl)-amine;

(4-Benzyloxy-phenyl)-(6-(5-((2-methanesulphonyl-ethylamino)-methyl)-furan-2-yl)-quinazolin-4-yl)-amine;

(4-(3-Fluorobenzyloxy-phenyl)-(6-(4-((2-methanesulphonyl-ethylamino)-methyl)-furan-2-yl)-pyrido[3,4-d]pyrimidin-4-yl)-amine;

(4-Benzyloxy-phenyl)-(6-(2-((2-methanesulphonyl-ethylamino)-methyl)-thiazol-4-yl)-quinazolin-4-yl)-amine;

N-{4-[(3-Fluorobenzyl)oxy]phenyl}-6-[5-({[2-(methanesulphonyl)ethyl]amino}methyl)-2-furyl]-4-quinazolinamine;

N-{4-[(3-Fluorobenzyl)oxy]-3-methoxyphenyl}-6-[5-({[2-(methanesulphonyl)ethyl]amino}methyl)-2-furyl]-4-quinazolinamine;

N-[4-(Benzyloxy)phenyl]-7-methoxy-6-[5-({[2-(methanesulphonyl)ethyl]amino}methyl)-2-furyl]-4-quinazolinamine;

N-[4-(Benzyloxy)phenyl]-6-[4-({[2-(methanesulphonyl)ethyl]amino}methyl)-2-furyl]-4-quinazolinamine;

N-{4-[(3-Fluorobenzyl)oxy]-3-methoxyphenyl}-6-[2-({[2-(methanesulphonyl)ethyl]amino}methyl)-1,3-thiazol-4-yl]-4-quinazolinamine;

N-{4-[(3-Bromobenzyl)oxy]phenyl}-6-[2-({[2-(methanesulphonyl)ethyl]amino}methyl)-1,3-thiazol-4-yl]-4-quinazolinamine;

N-{4-[(3-Fluorobenzyl)oxy]phenyl}-6-[2-({[2-(methanesulphonyl)ethyl]amino}methyl)-1,3-thiazol-4-yl]-4-quinazolinamine;

N-[4-(Benzyloxy)-3-fluorophenyl]-6-[2-({[2-(methanesulphonyl)ethyl]amino}methyl)-1,3-thiazol-4-yl]-4-quinazolinamine;

N-(1-Benzyl-1H-indazol-5-yl)-7-methoxy-6-[5-({[2-(methanesulphonyl)ethyl]amino}methyl)-2-furyl]-4-quinazolinamine;

6-[5-({[2-(Methanesulphonyl)ethyl]amino}methyl)-2-furyl]-N-(4-{[3-(trifluoromethyl)benzyl]oxy}phenyl)-4-quinazolinamine;

N-{3-Fluoro-4-[(3-fluorobenzyl)oxy]phenyl}-6-[5-({[2-(methanesulphonyl)ethyl]amino}methyl)-2-furyl]-4-quinazolinamine;

N-{4-[(3-Bromobenzyl)oxy]phenyl}-6-[5-({[2-(methanesulphonyl)ethyl]amino}methyl)-2-furyl]-4-quinazolinamine;

N-[4-(Benzyloxy)phenyl]-6-[3-({[2-(methanesulphonyl)ethyl]amino}methyl)-2-furyl]-4-quinazolinamine;

N-[1-(3-Fluorobenzyl)-1H-indazol-5-yl]-6-[2-({[2-(methanesulphonyl)ethyl]amino}methyl)-1,3-thiazol-4-yl]-4-quinazolinamine;

6-[5-({[2-(Methanesulphonyl)ethyl]amino}methyl)-2-furyl]-N-[4-(benzenesulphonyl)phenyl]-4-quinazolinamine;

6-[2-({[2-(Methanesulphonyl)ethyl]amino}methyl)-1,3-thiazol-4-yl]-N-[4-(benzenesulphonyl)phenyl]-4-quinazolinamine;

6-[2-({[2-(Methanesulphonyl)ethyl]amino}methyl)-1,3-thiazol-4-yl]-N-(4-{[3-(trifluoromethyl)benzyl]oxy}phenyl)-4-quinazolinamine N-{3-Fluoro-4-[(3-fluorobenzyl)oxy]phenyl}-6-[2-({[2-(methanesulphonyl)ethyl]amino}methyl)-1,3-thiazol-4-yl]-4-quinazolinamine;

N-(1-Benzyl-1H-indazol-5-yl)-6-[2-({[2-(methanesulphonyl)ethyl]amino}methyl)-1,3-thiazol-4-yl]-4-quinazolinamine;

N-(3-Fluoro-4-benzyloxyphenyl)-6-[2-({[2-(methanesulphonyl)ethyl]amino}methyl)-1,3-thiazol-4-yl]-4-quinazolinamine;

N-(3-Chloro-4-benzyloxyphenyl)-6-[2-({[2-(methanesulphonyl)ethyl]amino}methyl)-1,3-thiazol-4-yl]-4-quinazolinamine;

N-{3-Chloro-4-[(3-fluorobenzyl)oxy]phenyl}-6-[5-({[2-(methanesulphonyl)ethyl]amino}methyl)-2-furyl]-4-quinazolinamine;

6-[5-({[2-(Methanesulphonyl)ethyl]amino}methyl)-2-furyl]-7-methoxy-N-(4-benzenesulphonyl)phenyl-4-quinazolinamine;

N-[4-(Benzyloxy)phenyl]-7-fluoro-6-[5-({[2-(methanesulphonyl)ethyl]amino}methyl)-2-furyl]-4-quinazolinamine;

N-(1-Benzyl-1H-indazol-5-yl)-7-fluoro-6-[5-({[2-(methanesulphonyl)ethyl]amino}methyl)-2-furyl]-4-quinazolinamine;

N-[4-(Benzenesulphonyl)phenyl]-7-fluoro-6-[5-({[2-(methanesulphonyl)ethyl]amino)methyl)-2-furyl]-4-quinazolinamine;

N-(3-Trifluoromethyl-4-benzyloxyphenyl)-6-[5-({[2-(methanesulphonyl)ethyl]amino}methyl)-4-furyl]-4-quinazolinamine;

and salts or solvates thereof, particularly pharmaceutically acceptable salts thereof.

Other preferred compounds of the present invention include:
(4-Phenoxyphenyl)-(7-(2-(2-methanesulphonyl)ethylaminomethyl)thiazol-4-yl)-quinolin-4-yl)amine;
(4-Phenoxyphenyl)-(7-(4-(2-methanesulphonyl)ethylaminomethyl)thiazol-5-yl)-quinolin-4-yl)amine;
(4-Phenoxyphenyl)-(7-(5-(2-(methanesulphonyl)ethylaminomethyl)furan-2-yl)-quinolin-4-yl)amine;
and salts or solvates thereof, particularly pharmaceutically acceptable salts thereof.

In a particular embodiment, EGFR inhibitors are compound of formula III selected from the group consisting of:
(4-Phenoxy-phenyl)-(6-(5-((2-methanesulphonyl-ethylamino)methyl)-furan-2-yl)-pyrido[3,4-d]pyrimidin-4-yl)-amine;
(1-Benzyl-1H-indazol-5-yl)-(6-(4-((2-methanesulphonyl-ethylamino)methyl)-furan-2-yl)-pyrido[3,4-d]pyrimidin-4-yl)-amine;
(4-(4-Fluorobenzyloxy)-phenyl)-(6-(4-((2-methanesulphonyl-ethylamino)methyl)-furan-2-yl)-pyrido[3,4-d]pyrimidin-4-yl)-amine;
(4-Benzenesulphonyl-phenyl)-(6-(4-((2-methanesulphonyl-ethylamino)-methyl)-furan-2-yl)-pyrido[3,4-d]pyrimidin-4-yl)-amine;
(4-Benzyloxy-phenyl)-(6-(4-((2-methanesulphonyl-ethylamino)methyl)-furan-2-yl)-pyrido[3,4-d]pyrimidin-4-yl)-amine;
(4-Phenoxy-phenyl)-(6-(4-((2-methanesulphonyl-ethylamino)methyl)-furan-2-yl)-pyrido[3,4-d]pyrimidin-4-yl)-amine;

In a particular embodiment, EGFR inhibitors are compound of formula III selected from the group consisting of:
(1-Benzyl-1H-indazol-5-yl)-(6-(2-((2-methanesulphonyl-ethylamino)methyl)-thiazol-4-yl)-pyrido[3,4-d]pyrimidin-4-yl)-amine;
(4-(4-Fluorobenzyloxy)-phenyl)-(6-(2-((2-methanesulphonyl-ethylamino)methyl)-thiazol-4-yl)-pyrido[3,4-d]pyrimidin-4-yl)-amine;
(4-(3-Fluorobenzyloxy)-phenyl)-(6-(2-((2-methanesulphonyl-ethylamino)methyl)-thiazol-4-yl)-pyrido[3,4-d]pyrimidin-4-yl)-amine;
(4-Benzenesulphonyl-phenyl)-(6-(2-((2-methanesulphonyl-ethylamino)-methyl)-thiazol-4-yl)-pyrido[3,4-d]pyrimidin-4-yl)-amine;
(4-Benzyloxy-phenyl)-(6-(2-((2-methanesulphonyl-ethylamino)methyl)-thiazol-4-yl)-pyrido[3,4-d]pyrimidin-4-yl)-amine;
(4-Phenoxy-phenyl)-(6-(2-((2-methanesulphonyl-ethylamino)methyl)-thiazol-4-yl)-pyrido[3,4-d]pyrimidin-4-yl)-amine;

In a particular embodiment, EGFR inhibitors are compound of formula III selected from the group consisting of:
(1-Benzyl-1H-indazol-5-yl)-(6-(2-((2-methanesulphonyl-ethylamino)methyl)-thiazol-5-yl)-pyrido[3,4-d]pyrimidin-4-yl)-amine;
(4-(4-Fluorobenzyloxy)-phenyl)-(6-(2-((2-methanesulphonyl-ethylamino)methyl)-thiazol-5-yl)-pyrido[3,4-d]pyrimidin-4-yl)-amine;
(4-(3-Fluorobenzyloxy)-phenyl)-(6-(2-((2-methanesulphonyl-ethylamino)methyl)-thiazol-5-yl)-pyrido[3,4-d]pyrimidin-4-yl)-amine;
(4-Benzenesulphonyl-phenyl)-(6-(2-((2-methanesulphonyl-ethylamino)-methyl)-thiazol-5-yl)-pyrido[3,4-d]pyrimidin-4-yl)-amine;
(4-Benzyloxy-phenyl)-(6-(2-((2-methanesulphonyl-ethylamino)methyl)-thiazol-5-yl)-pyrido[3,4-d]pyrimidin-4-yl)-amine;
(4-Phenoxy-phenyl)-(6-(2-((2-methanesulphonyl-ethylamino)methyl)-thiazol-5-yl)-pyrido[3,4-d]pyrimidin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-thiazol-2-yl)-pyrido[3,4-d]pyrimidin-4-yl)-amine;
(4-(4-Fluorobenzyloxy)-phenyl)-(6-(4-((2-methanesulphonyl-ethylamino)methyl)-thiazol-2-yl)-pyrido[3,4-d]pyrimidin-4-yl)-amine;
(4-(3-Fluorobenzyloxy)-phenyl)-(6-(4-((2-methanesulphonyl-ethylamino)methyl)-thiazol-2-yl)-pyrido[3,4-d]pyrimidin-4-yl)-amine;
(4-Benzenesulphonyl-phenyl)-(6-(4-((2-methanesulphonyl-ethylamino)-methyl)-thiazol-2-yl)-pyrido[3,4-d]pyrimidin-4-yl)-amine;
(4-Benzyloxy-phenyl)-(6-(4-((2-methanesulphonyl-ethylamino)methyl)-thiazol-2-yl)-pyrido[3,4-d]pyrimidin-4-yl)-amine;
(4-Phenoxy-phenyl)-(6-(4-((2-methanesulphonyl-ethylamino)methyl)-thiazol-2-yl)-pyrido[3,4-d]pyrimidin-4-yl)-amine;

In a particular embodiment, EGFR inhibitors are compound of formula III selected from the group consisting of:
(1-Benzyl-1H-indazol-5-yl)-(6-(5-((2-methanesulphonyl-ethylamino)methyl)-thiazol-2-yl)-pyrido[3,4-d]pyrimidin-4-yl)-amine;
(4-(4-Fluorobenzyloxy)-phenyl)-(6-(5-((2-methanesulphonyl-ethylamino)methyl)-thiazol-2-yl)-pyrido[3,4-d]pyrimidin-4-yl)-amine;
(4-(3-Fluorobenzyloxy)-phenyl)-(6-(5-((2-methanesulphonyl-ethylamino)methyl)-thiazol-2-yl)-pyrido[3,4-d]pyrimidin-4-yl)-amine;
(4-Benzenesulphonyl-phenyl)-(6-(5-((2-methanesulphonyl-ethylamino)-methyl)-thiazol-2-yl)-pyrido[3,4-d]pyrimidin-4-yl)-amine;
(4-Benzyloxy-phenyl)-(6-(5-((2-methanesulphony-ethylamino)methyl)-thiazol-2-yl)-pyrido[3,4-d]pyrimidin-4-yl)-amine;
(4-Phenoxy-phenyl)-(6-(5-((2-methanesulphonyl-ethylamino)methyl)-thiazol-2-yl)-pyrido[3,4-d]pyrimidin-4-yl)-amine;

In a particular embodiment, EGFR inhibitors are compound of formula III selected from the group consisting of:
(1-Benzyl-1H-indazol-5-yl)-(6-(3-((2-methanesulphonyl-ethylamino)methyl)-phenyl)-pyrido[3,4-d]pyrimidin-4-yl)-amine;
(4-(4-Fluorobenzyloxy)-phenyl)-(6-(3-((2-methanesulphonyl-ethylamino)methyl)-phenyl)-pyrido[3,4-d]pyrimidin-4-yl)-amine;
(4-(3-Fluorobenzyloxy)-phenyl)-(6-(3-((2-methanesulphonyl-ethylamino)methyl)-phenyl)-pyrido[3,4-d]pyrimidin-4-yl)-amine;
(4-Benzenesulphonyl-phenyl)-(6-(3-((2-methanesulphonyl-ethylamino)-methyl)-phenyl)-pyrido[3,4-d]pyrimidin-4-yl)-amine;
(4-Phenoxy-phenyl)-(6-(3-((2-methanesulphonyl-ethylamino)-methyl)-phenyl)-pyrido[3,4-d]pyrimidin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-phenyl)-pyrido[3,4-d]pyrimidin-4-yl)-amine;

(4-(4-Fluorobenzyloxy)-phenyl)-(6-(4-((2-methanesulphonyl-ethylamino)methyl)-phenyl)-pyrido[3,4-d]pyrimidin-4-yl)-amine;
(4-(3-Fluorobenzyloxy)-phenyl)-(6-(4-((2-methanesulphonyl-ethylamino)methyl)-phenyl)-pyrido[3,4-d]pyrimidin-4-yl)-amine;
(4-Benzenesulphonyl-phenyl)-(6-(4-((2-methanesulphonyl-ethylamino)-methyl)-phenyl)-pyrido[3,4-d]pyrimidin-4-yl)-amine;
(4-Benzyloxy-phenyl)-(6-(4-((2-methanesulphonyl-ethylamino)-methyl)-phenyl)-pyrido[3,4-d]pyrimidin-4-yl)-amine;
(4-Phenoxy-phenyl)-(6-(4-((2-methanesulphonyl-ethylamino)-methyl)-phenyl)-pyrido[3,4-d]pyrimidin-4-yl)-amine;

In a particular embodiment, EGFR inhibitors are compound of formula III selected from the group consisting of:
(4-(4-Fluorobenzyloxy)-phenyl)-(6-(5-((2-methanesulphonyl-ethylamino)methyl)-furan-2-yl)-quinazolin-4-yl)-amine;
(4-Phenoxy-phenyl)-(6-(5-((2-methanesulphonyl-ethylamino)methyl)-furan-2-yl)-quinazolin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-furan-2-yl)-quinazolin-4-yl)-amine;
(4-(4-Fluorobenzyloxy)-phenyl)-(6-(4-((2-methanesulphonyl-ethylamino)methyl)-furan-2-yl)-quinazolin-4-yl)-amine;
(4-(3-Fluorobenzyloxy)-phenyl)-(6-(4-((2-methanesulphonyl-ethylamino)methyl)-furan-2-yl)-quinazolin-4-yl)-amine;
(4-Benzenesulphonyl-phenyl)-(6-(4-((2-methanesulphonyl-ethylamino)-methyl)-furan-2-yl)-quinazolin-4-yl)-amine;
(4-Phenoxy-phenyl)-(6-(4-((2-methanesulphonyl-ethylamino)methyl)-furan-2-yl)-quinazolin-4-yl)-amine;

In a particular embodiment, EGFR inhibitors are compound of formula III selected from the group consisting of:
(1-Benzyl-1H-indazol-5-yl)-(6-(2-((2-methanesulphonyl-ethylamino)methyl)-thiazol-4-yl)-quinazolin-4-yl)-amine;
(4-(4-Fluorobenzyloxy)-phenyl)-(6-(2-((2-methanesulphonyl-ethylamino)methyl)-thiazol-4-yl)-quinazolin-4-yl)-amine;
(4-(3-Fluorobenzyloxy)-phenyl)-(6-(2-((2-methanesulphonyl-ethylamino)methyl)-thiazol-4-yl)-quinazolin-4-yl)-amine;
(4-Phenoxy-phenyl)-(6-(2-((2-methanesulphonyl-ethylamino)methyl)-thiazol-4-yl)-quinazolin-4-yl)-amine;

In a particular embodiment, EGFR inhibitors are compound of formula III selected from the group consisting of:
(1-Benzyl-1H-indazol-5-yl)-(6-(2-((2-methanesulphonyl-ethylamino)methyl)-thiazol-5-yl)-quinazolin-4-yl)-amine;
(4-(4-Fluorobenzyloxy)-phenyl)-(6-(2-((2-methanesulphonyl-ethylamino)methyl)-thiazol-5-yl)-quinazolin-4-yl)-amine;
(4-(3-Fluorobenzyloxy)-phenyl)-(6-(2-((2-methanesulphonyl-ethylamino)methyl)-thiazol-5-yl)-quinazolin-4-yl)-amine;
(4-Benzenesulphonyl-phenyl)-(-2-(-methanesulphonyl-ethylamino)-methyl)-thiazol-5-yl)-quinazolin-4-yl)-amine;
(4-Benzyloxy-phenyl)-(6-(2-((2-methanesulphonyl-ethylamino)methyl)-thiazol-5-yl)-quinazolin-4-yl)-amine;
(4-Phenoxy-phenyl)-(6-(2-((2-methanesulphonyl-ethylamino)methyl)-thiazol-5-yl)-quinazolin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-thiazol-2-yl)-quinazolin-4-yl)-amine;
(4-(4-Fluorobenzyloxy)-phenyl)-(6-(4-((2-methane-sulphony-ethylamino)methyl)-thiazol-2-yl)-quinazolin-4-yl)-amine;
(4-(3-Fluorobenzyloxy)-phenyl)-(6-(4-((2-methanesulphonyl-ethylamino)methyl)-thiazol-2-yl)-quinazolin-4-yl)-amine;
(4-Benzenesulphonyl-phenyl)-(6-(4-((2-methanesulphonyl-ethylamino)-methyl)-thiazol-2-yl)-quinazolin-4-yl)-amine;
(4-Benzyloxy-phenyl)-(6-(4-((2-methanesulphonyl-ethylamino)methyl)-thiazol-2-yl)-quinazolin-4-yl)-amine;
(4-Phenoxy-phenyl)-(6-(4-((2-methanesulphonyl-ethylamino)methyl)-thiazol-2-yl)-quinazolin-4-yl)-amine;

In a particular embodiment, EGFR inhibitors are compound of formula III selected from the group consisting of:
(1-Benzyl-1H-indazol-5-yl)-(6-(5-((2-methanesulphonyl-ethylamino)methyl)-thiazol-2-yl)-quinazolin-4-yl)-amine;
(4-(4-Fluorobenzyloxy)-phenyl)-(6-(5-((2-methanesulphonyl-ethylamino)methyl)-thiazol-2-yl)-quinazolin-4-yl)-amine;
(4-(3-Fluorobenzyloxy)-phenyl)-(6-(5-((2-methanesulphonyl-ethylamino)methyl)-thiazol-2-yl)-quinazolin-4-yl)-amine;
(4-Benzenesulphonyl-phenyl)-(6-(5-((2-methanesulphonyl-ethylamino)-methyl)-thiazol-2-yl)-quinazolin-4-yl)-amine;
(4-Benzyloxy-phenyl)-(6-(5-((2-methanesulphonyl-ethylamino)methyl)-thiazol-2-yl)-quinazolin-4-yl)-amine;
(4-Phenoxy-phenyl)-(6-(5-((2-methanesulphonyl-ethylamino)methyl)-thiazol-2-yl)-quinazolin-4-yl)-amine;

In a particular embodiment, EGFR inhibitors are compound of formula III selected from the group consisting of:
(1-Benzyl-1H-indazol-5-yl)-(6-(3-((2-methanesulphonyl-ethylamino)methyl)-phenyl)-quinazolin-4-yl)-amine;
(4-(4-Fluorobenzyloxy)-phenyl)-(6-(3-((2-methanesulphonyl-ethylamino)methyl)-phenyl)-quinazolin-4-yl)-amine;
(4-(3-Fluorobenzyloxy)-phenyl)-(6-(3-((2-methanesulphonyl-ethylamino)methyl)-phenyl)-quinazolin-4-yl)-amine;
(4-Benzenesulphonyl-phenyl)-(6-(3-((2-methanesulphonyl-ethylamino)-methyl)-phenyl)-quinazolin-4-yl)-amine;
(4-Benzyloxy-phenyl)-(6-(3-((2-methanesulphonyl-ethylamino)-methyl)-phenyl)-quinazolin-4-yl)-amine;
(4-Phenoxy-phenyl)-(6-(3-((2-methanesulphonyl-ethylamino)-methyl)-phenyl)-quinazolin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-phenyl)-quinazolin-4-yl)-amine;
(4-(4-Fluorobenzyloxy)-phenyl)-(6-(4-((2-methanesulphonyl-ethylamino)methyl)-phenyl)-quinazolin-4-yl)-amine;
(4-(3-Fluorobenzyloxy)-phenyl)-(6-(4-((2-methanesulphonyl-ethylamino)methyl)-phenyl)-quinazolin-4-yl)-amine;
(4-Benzenesulphonyl-phenyl)-(6-(4-((2-methanesulphonyl-ethylamino)-methyl)-phenyl)-quinazolin-4-yl)-amine;
(4-Benzyloxy-phenyl)-(6-(4-((2-methanesulphonyl-ethylamino)-methyl)-phenyl)-quinazolin-4-yl)-amine;
(4-Phenoxy-phenyl)-(6-(4-((2-methanesulphonyl-ethylamino)-methyl)-phenyl)-quinazolin-4-yl)-amine;

In a particular embodiment, EGFR inhibitors are compound of formula III selected from the group consisting of:

(4-(4-Fluorobenzyloxy)-phenyl)-(7-(5-((2-methane-sulphony-ethylamino)methyl)-furan-2-yl)-quinazolin-4-yl)-amine;
(4-(3-Fluorobenzyloxy)-phenyl)-(7-(5-((2-methanesulphonyl-ethylamino)methyl)-furan-2-yl)-quinazolin-4-yl)-amine;
(4-Benzenesulphonyl-phenyl)-(7-(5-((2-methanesulphonyl-ethylamino)-methyl)-furan-2-yl)-quinazolin-4-yl)-amine;
(4-Benzyloxy-phenyl)-(7-(5-((2-methanesulphonyl-ethylamino)methyl)-furan-2-yl)-quinazolin-4-yl)-amine;
(4-Phenoxy-phenyl)-(7-(5-((2-methanesulphonyl-ethylamino)methyl)-furan-2-yl)-quinazolin-4-yl)-amine;

In a particular embodiment, EGFR inhibitors are compound of formula III selected from the group consisting of:
(1-Benzyl-1H-indazol-5-yl)-(7-(4-((2-methanesulphonyl-ethylamino)methyl)-furan-2-yl)-quinazolin-4-yl)-amine;
(4-(4-Fluorobenzyloxy)-phenyl)-(7-(4-((2-methane-sulphony-ethylamino)methyl)-furan-2-yl)-quinazolin-4-yl)-amine;
(4-(3-Fluorobenzyloxy)-phenyl)-(7-(4-((2-methane-sulphony-ethylamino)methyl)-furan-2-yl)-quinazolin-4-yl)-amine;
(4-Benzenesulphonyl-phenyl)-(7-(4-((2-methanesulphonyl-ethylamino)-methyl)-furan-2-yl)-quinazolin-4-yl)-amine;
(4-Benzyloxy-phenyl)-(7-(4-((2-methanesulphonyl-ethylamino)methyl)-furan-2-yl)-quinazolin-4-yl)-amine;
(4-Phenoxy-phenyl)-(7-(4-((2-methanesulphony-ethylamino)methyl)-furan-2-yl)-quinazolin-4-yl)-amine;

In a particular embodiment, EGFR inhibitors are compound of formula III selected from the group consisting of:
(1-Benzyl-1H-indazol-5-yl)-(7-(2-((2-methanesulphonyl-ethylamino)methyl)-thiazol-4-yl)-quinazolin-4-yl)-amine;
(4-(4-Fluorobenzyloxy)-phenyl)-(7-(2-((2-methanesulphonyl-ethylamino)methyl)-thiazol-4-yl)-quinazolin-4-yl)-amine;
(4-(3-Fluorobenzyloxy)-phenyl)-(7-(2-((2-methanesulphonyl-ethylamino)methyl)-thiazol-4-yl)-quinazolin-4-yl)-amine;
(4-Benzenesulphonyl-phenyl)-(7-(2-((2-methanesulphonyl-ethylamino)-methyl)-thiazol-4-yl)-quinazolin-4-yl)-amine;
(4-Benzyloxy-phenyl)-(7-(2-((2-methanesulphonyl-ethylamino)methyl)-thiazol-4-yl)-quinazolin-4-yl)-amine;
(4-Phenoxy-phenyl)-(7-(2-((2-methanesulphonyl-ethylamino)methyl)-thiazol-4-yl)-quinazolin-4-yl)-amine;

In a particular embodiment, EGFR inhibitors are compound of formula III selected from the group consisting of:
(1-Benzyl-1H-indazol-5-yl)-(7-(2-((2-methanesulphonyl-ethylamino)methyl)-thiazol-5-yl)-quinazolin-4-yl)-amine;
(4-(4-Fluorobenzyloxy)-phenyl)-(7-(2-((2-methanesulphonyl-ethylamino)methyl)-thiazol-5-yl)-quinazolin-4-yl)-amine;
(4-(3-Fluorobenzyloxy)-phenyl)-(7-(2-((2-methanesulphonyl-ethylamino)methyl)-thiazol-5-yl)-quinazolin-4-yl)-amine;
(4-Benzenesulphonyl-phenyl)-(7-(2-((2-methanesulphonyl-ethylamino)-methyl)-thiazol-5-yl)-quinazolin-4-yl)-amine;
(4-Benzyloxy-phenyl)-(7-(2-((2-methanesulphonyl-ethylamino)methyl)-thiazol-5-yl)-quinazolin-4-yl)-amine;
(4-Phenoxy-phenyl)-(7-(2-((2-methanesulphonyl-ethylamino)methyl)-thiazol-5-yl)-quinazolin-4-yl)-amine;

In a particular embodiment, EGFR inhibitors are compound of formula III selected from the group consisting of:
(1-Benzyl-1H-indazol-5-yl)-(7-(4-((2-methanesulphonyl-ethylamino)methyl)-thiazol-2-yl)-quinazolin-4-yl)-amine;
(4-(4-Fluorobenzyloxy)-phenyl)-(7-(4-((2-methanesulphonyl-ethylamino)methyl)-thiazol-2-yl)-quinazolin-4-yl)-amine;
(4-(3-Fluorobenzyloxy)-phenyl)-(7-(4-((2-methanesulphonyl-ethylamino)methyl)-thiazol-2-yl)-quinazolin-4-yl)-amine;
(4-Benzenesulphonyl-phenyl)-(7-(4-((2-methanesulphonyl-ethylamino)-methyl)-thiazol-2-yl)-quinazolin-4-yl)-amine;
(4-Benzyloxy-phenyl)-(7-(4-((2-methanesulphonyl-ethylamino)methyl)-thiazol-2-yl)-quinazolin-4-yl)-amine;
(4-Phenoxy-phenyl)-(7-(4-((2-methanesulphonyl-ethylamino)methyl)-thiazol-2-yl)-quinazolin-4-yl)-amine;

In a particular embodiment, EGFR inhibitors are compound of formula III selected from the group consisting of:
(1-Benzyl-1H-indazol-5-yl)-(7-(5-((2-methanesulphonyl-ethylamino)methyl)-thiazol-2-yl)-quinazolin-4-yl)-amine;
(4-(4-Fluorobenzyloxy)-phenyl)-(7-(5-((2-methanesulphonyl-ethylamino)methyl)-thiazol-2-yl)-quinazolin-4-yl)-amine;
(4-(3-Fluorobenzyloxy)-phenyl)-(7-(5-((2-methanesulphonyl-ethylamino)methyl)-thiazol-2-yl)-quinazolin-4-yl)-amine;
(4-Benzenesulphonyl-phenyl)-(7-(5-((2-methanesulphonyl-ethylamino)-methyl)-thiazol-2-yl)-quinazolin-4-yl)-amine;
(4-Benzyloxy-phenyl)-(7-(5-((2-methanesulphonyl-ethylamino)methyl)-thiazol-2-yl)-quinazolin-4-yl)-amine;
(4-Phenoxy-phenyl)-(7-(5-((2-methanesulphonyl-ethylamino)methyl)-thiazol-1-2-yl)-quinazolin-4-yl)-amine;

In a particular embodiment, EGFR inhibitors are compound of formula III selected from the group consisting of:
(1-Benzyl-1H-indazol-5-yl)-(7-(3-((2-methanesulphonyl-ethylamino)methyl)-phenyl)-quinazolin-4-yl)-amine;
(4-(4-Fluorobenzyloxy)-phenyl)-(7-(3-((2-methanesulphonyl-ethylamino)methyl)-phenyl)-quinazolin-4-yl)-amine;
(4-(3-Fluorobenzyloxy)-phenyl)-(7-(3-((2-methanesulphonyl-ethylamino)methyl)-phenyl)-quinazolin-4-yl)-amine;
(4-Benzenesulphonyl-phenyl)-(7-(3-((2-methanesulphonyl-ethylamino)-methyl)-phenyl)-quinazolin-4-yl)-amine;
(4-Benzyloxy-phenyl)-(7-(3-((2-methanesulphonyl-ethy-lamino)-methyl)-phenyl)-quinazolin-4-yl)-amine;
(4-Phenoxy-phenyl)-(7-(3-((2-methanesulphonyl-ethy-lamino)-methyl)-phenyl)-quinazolin-4-yl)-amine;

In a particular embodiment, EGFR inhibitors are compound of formula III selected from the group consisting of:
(1-Benzyl-1H-indazol-5-yl)-(7-(4-((2-methanesulphonyl-ethylamino)methyl)-phenyl)-quinazolin-4-yl)-amine;
(4-(4-Fluorobenzyloxy)-phenyl)-(7-(4-((2-methanesulphonyl-ethylamino)methyl)-phenyl)-quinazolin-4-yl)-amine;
(4-(3-Fluorobenzyloxy)-phenyl)-(7-(4-((2-methanesulphonyl-ethylamino)methyl)-phenyl)-quinazolin-4-yl)-amine;
(4-Benzenesulphonyl-phenyl)-(7-(4-((2-methanesulphonyl-ethylamino)-methyl)-phenyl)-quinazolin-4-yl)-amine;
(4-Benzyloxy-phenyl)-(7-(4-((2-methanesulphonyl-ethy-lamino)-methyl)-phenyl)-quinazolin-4-yl)-amine;
(4-Phenoxy-phenyl)-(7-(4-((2-methanesulphonyl-ethy-lamino)-methyl)-phenyl)-quinazolin-4-yl)-amine;

In a particular embodiment, EGFR inhibitors are compound of formula III selected from the group consisting of:
(1-Benzyl-1H-indazol-5-yl)-(6-(5-((2-methanesulphonyl-ethylamino)methyl)-furan-2-yl)-pyrido[3,4-d]pyridin-4-yl)-amine;

(4-(4-Fluorobenzyloxy)-phenyl)-(6-(5-((2-methanesulphonyl-ethylamino)methyl)-furan-2-yl)-pyrido[3,4-d]pyridin-4-yl)-amine;
(4-(3-Fluorobenzyloxy)-phenyl)-(6-(5-((2-methanesulphonyl-ethylamino)methyl)-furan-2-yl)-pyrido[3,4-d]pyridin-4-yl)-amine;
(4-Benzenesulphonyl-phenyl)-(6-(5-((2-methanesulphonyl-ethylamino)-methyl)-furan-2-yl)-pyrido[3,4-d]pyridin-4-yl)-amine;
(4-Benzyloxy-phenyl)-(6-(5-((2-methanesulphonyl-ethyl amino)methyl)-furan-2-yl)-pyrido[3,4-d]pyridin-4-yl)-amine;
(4-Phenoxy-phenyl)-(6-(5-((2-methanesulphonyl-ethylamino)methyl)-furan-2-yl)-pyrido[3,4-d]pyridin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-furan-2-yl)-pyrido[3,4-d]pyridin-4-yl)-amine;
(4-(4-Fluorobenzyloxy)-phenyl)-(6-(4-((2-methanesulphonyl-ethylamino)methyl)-furan-2-yl)-pyrido[3,4-d]pyridin-4-yl)-amine;
(4-(3-Fluorobenzyloxy)-phenyl)-(6-(4-((2-methanesulphonyl-ethylamino)methyl)-furan-2-yl)-pyrido[3,4-d]pyridin-4-yl)-amine;
(4-Benzenesulphonyl-phenyl)-(6-(4-((2-methanesulphonyl-ethylamino)-methyl)-furan-2-yl)-pyrido[3,4-d]pyridin-4-yl)-amine;
(4-Benzyloxy-phenyl)-(6-(4-((2-methanesulphonyl-ethylamino)methyl)-furan-2-yl)-pyrido[3,4-d]pyridin-4-yl)-amine;
(4-Phenoxy-phenyl)-(6-(4-((2-methanesulphonyl-ethylamino)methyl)-furan-2-yl)-pyrido[3,4-d]pyridin-4-yl)-amine;

In a particular embodiment, EGFR inhibitors are compound of formula III selected from the group consisting of:
(1-Benzyl-1H-indazol-5-yl)-(6-(2-((2-methanesulphonyl-ethylamino)methyl)-thiazol-4-yl)-pyrido[3,4-d]pyridin-4-yl)-amine;
(4-(4-Fluorobenzyloxy)-phenyl)-(6-(2-((2-methanesulphonyl-ethylamino)methyl)-thiazol-4-yl)-pyrido[3,4-d]pyridin-4-yl)-amine;
(4-(3-Fluorobenzyloxy)-phenyl)-(6-(2-((2-methanesulphonyl-ethylamino)methyl)-thiazol-4-yl)-pyrido[3,4-d]pyridin-4-yl)-amine;
(4-Benzenesulphonyl-phenyl)-(6-(2-((2-methanesulphonyl-ethylamino)-methyl)-thiazol-4-yl)-pyrido[3,4-d]pyridin-4-yl)-amine;
(4-Benzyloxy-phenyl)-(6-(2-((2-methanesulphonyl-ethylamino)methyl)-thiazol-4-yl)-pyrido[3,4-d]pyridin-4-yl)-amine;
(4-Phenoxy-phenyl)-(6-(2-((2-methanesulphonyl-ethylamino)methyl)-thiazol-4-yl)-pyrido[3,4-d]pyridin-4-yl)-amine;

In a particular embodiment, EGFR inhibitors are compound of formula III selected from the group consisting of:
(1-Benzyl-1H-indazol-5-yl)-(6-(2-((2-methanesulphonyl-ethylamino)methyl)-thiazol-5-yl)-pyrido[3,4-d]pyridin-4-yl)-amine;
(4-(4-Fluorobenzyloxy)-phenyl)-(6-(2-((2-methanesulphonyl-ethylamino)methyl)-thiazol-5-yl)-pyrido[3,4-d]pyridin-4-yl)-amine;
(4-(3-Fluorobenzyloxy)-phenyl)-(6-(2-((2-methanesulphonyl-ethylamino)methyl)-thiazol-5-yl)-pyrido[3,4-d]pyridin-4-yl)-amine;
(4-Benzenesulphonyl-phenyl)-(6-(2-((2-methanesulphonyl-ethylamino)-methyl)-thiazol-5-yl)-pyrido[3,4-d]pyridin-4-yl)-amine;
(4-Benzyloxy-phenyl)-(6-(2-((2-methanesulphonyl-ethylamino)methyl)-thiazol-5-yl)-pyrido[3,4-d]pyridin-4-yl)-amine;
(4-Phenoxy-phenyl)-(6-(2-((2-methanesulphonyl-ethylamino)methyl)-thiazol-5-yl)-pyrido[3,4-d]pyridin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-thiazol-2-yl)-pyrido[3,4-d]pyridin-4-yl)-amine;
(4-(4-Fluorobenzyloxy)-phenyl)-(6-(4-((2-methanesulphonyl-ethylamino)methyl)-thiazol-2-yl)-pyrido[3,4-d]pyridin-4-yl)-amine;
(4-(3-Fluorobenzyloxy)-phenyl)-(6-(4-((2-methanesulphonyl-ethylamino)methyl)-thiazol-2-yl)-pyrido[3,4-d]pyridin-4-yl)-amine;
(4-Benzenesulphonyl-phenyl)-(6-(4-((2-methanesulphonyl-ethylamino)-methyl)-thiazol-2-yl)-pyrido[3,4-d]pyridin-4-yl)-amine;
(4-Benzyloxy-phenyl)-(6-(4-((2-methanesulphonyl-ethylamino)methyl)-thiazol-2-yl)-pyrido[3,4-d]pyridin-4-yl)-amine;
(4-Phenoxy-phenyl)-(6-(4-((2-methanesulphony i-ethylamino)methyl)-thiazol-2-yl)-pyrido[3,4-d]pyridin-4-yl)-amine;

In a particular embodiment, EGFR inhibitors are compound of formula III selected from the group consisting of:
(1-Benzyl-1H-indazol-5-yl)-(6-(5-((2-methanesulphonyl-ethylamino)methyl)-thiazol-2-yl)-pyrido[3,4-d]pyridin-4-yl)-amine;
(4-(4-Fluorobenzyloxy)-phenyl)-(6-(5-((2-methanesulphonyl-ethylamino)methyl)-thiazol-2-y)-pyrido[3,4-d]pyridin-4-yl)-amine;
(4-(3-Fluorobenzyloxy)-phenyl)-(6-(5-((2-methanesulphonyl-ethylamino)methyl)-thiazol-2-yl)-pyrido[3,4-d]pyridin-4-yl)-amine;
(4-Benzenesulphonyl-phenyl)-(6-(5-((2-methanesulphonyl-ethylamino)-methyl)-thiazol-2-yl)-pyrido[3,4-d]pyridin-4-yl)-amine;
(4-Benzyloxy-phenyl)-(6-(5-((2-methanesulphonyl-ethylamino)methyl)-thiazol-2-yl)-pyrido[3,4-d]pyridin-4-yl)-amine;
(4-Phonoxy-phenyl)-(6-(5-((2-methanesulphonyl-ethylamino)methyl)-thiazol-2-yl)-pyrido[3,4-d]pyridin-4-yl)-amine;

In a particular embodiment, EGFR inhibitors are compound of formula III selected from the group consisting of:
(1-Benzyl-1H-indazol-5-yl)-(6-(3-((2-methanesulphonyl-ethylamino)methyl)-phenyl)-pyrido[3,4-d]pyridin-4-yl)-amine;
(4-(4-Fluorobenzyloxy)-phenyl)-(6-(3-((2-methanesulphonyl-ethylamino)methyl)-phenyl)-pyrido[3,4-d]pyridin-4-yl)-amine;
(4-(3-Fluorobenzyloxy)-phenyl)-(6-(3-((2-methanesulphonyl-ethylamino)methyl)-phenyl)-pyrido[3,4-d]pyridin-4-yl)-amine;
(4-Benzenesulphonyl-phenyl)-(6-(3-((2-methanesulphonyl-ethylamino)-methyl)-phenyl)-pyrido[3,4-d]pyridin-4-yl)-amine;
(4-Benzyloxy-phenyl)-(6-(3-((2-methanesulphonyl-ethylamino)-methyl)-phenyl)-pyrido[3,4-d]pyridin-4-yl)-amine;

(4-Phenoxy-phenyl)-(6-(3-((2-methanesulphonyl-ethylamino)-methyl)-phenyl)-pyrido[3,4-d]pyridin-4-yl)-amine;

In a particular embodiment, EGFR inhibitors are compound of formula III selected from the group consisting of:
(1-Benzyl-1H-indazol-5-yl)-(6-(4-((2-methanesulphonyl-ethylamino)methyl)-phenyl)-pyrido[3,4-d]pyridin-4-yl)-amine;
(4-(4-Fluorobenzyloxy)-phenyl)-(6-(4-((2-methanesulphonyl-ethylamino)methyl)-phenyl)-pyrido[3,4-d]pyridin-4-yl)-amine;
(4-(3-Fluorobenzyloxy)-phenyl)-(6-(4-((2-methanesulphonyl-ethylamino)methyl)-phenyl)-pyrido[3,4-d]pyridin-4-yl)-amine;
(4-Benzenesulphonyl-phenyl)-(6-(4-((2-methanesulphonyl-ethylamino)-methyl)-phenyl)-pyrido[3,4-d]pyridin-4-yl)-amine;
(4-Benzyloxy-phenyl)-(6-(4-((2-methanesulphonyl-ethylamino)-methyl)-phenyl)-pyrido[3,4-d]pyridin-4-yl)-amine;
(4-Phenoxy-phenyl)-(6-(4-((2-methanesulphonyl-ethylamino)-methyl)-phenyl)-pyrido[3,4-d]pyridin-4-yl)-amine;

In a particular embodiment, EGFR inhibitors are compound of formula III selected from the group consisting of:
(4-Phenoxy-phenyl)-(6-(5-((2-methanesulphonyl-ethylamino)methyl)-furan-2-yl)-quinolin-4-yl)-amine;
(4-Phenoxy-phenyl)-(6-(4-((2-methanesulphonyl-ethylamino)methyl)-furan-2-yl)-quinolin-4-yl)-amine;
(4-Phenoxy-phenyl)-(6-(2-((2-methanesulphonyl-ethylamino)methyl)-thiazol-4-yl)-quinolin-4-yl)-amine;
(4-Phenoxy-phenyl)-(6-(2-((2-methanesulphonyl-ethylamino)methyl)-thiazol-5-yl)-quinolin-4-yl)-amine;
(4-Phenoxy-phenyl)-(6-(4-((2-methanesulphonyl-ethylamino)methyl)-thiazol-2-yl)-quinolin-4-yl)-amine;
(4-Phenoxy-phenyl)-(6-(5-((2-methanesulphonyl-ethylamino)methyl)-thiazol-2-yl)-quinolin-4-yl)-amine;
(4-Phenoxy-phenyl)-(6-(3-((2-methanesulphonyl-ethylamino)-methyl)-phenyl)-quinolin-4-yl)-amine;
(4-Phenoxy-phenyl)-(6-(4-((2-methanesulphonyl-ethylamino)-methyl)-phenyl)-quinolin-4-yl)-amine;

In a particular embodiment, EGFR inhibitors are compound of formula III selected from the group consisting of:
(1-Benzyl-1H-indazol-5-yl)-(7-(5-((2-methanesulphonyl-ethylamino)methyl)-furan-2-yl)-quinolin-4-yl)-amine;
(4-(4-Fluorobenzyloxy)-phenyl)-(7-(5-((2-methanesulphony-ethylamino)methyl)-furan-2-yl)-quinolin-4-yl)-amine;
(4-(3-Fluorobenzyloxy)-phenyl)-(7-(5-((2-methanesulphonyl-ethylamino)methyl)-furan-2-yl)-quinolin-4-yl)-amine;
(4-Benzenesulphonyl-phenyl)-(7-(5((2-methanesulphonyl-ethylamino)-methyl)-furan-2-yl)-quinolin-4-yl)-amine;
(4-Benzyloxy-phenyl)-(7-(5-((2-methanesulphonyl-ethylamino)methyl)-furan-2-yl)-quinolin-4-yl)-amine;
(4-Phenoxy-phenyl)-(7-(5-((2-methanesulphonyl-ethylamino)methyl)-furan-2-yl)-quinolin-4-yl)-amine;

In a particular embodiment, EGFR inhibitors are compound of formula III selected from the group consisting of:
(1-Benzyl-1H-indazol-5-yl)-(7-(4-((2-methanesulphonyl-ethylamino)methyl)-furan-2-yl)-quinolin-4-yl)-amine;
(4-(4-Fluorobenzyloxy)-phenyl)-(7-(4-((2-methanesuphony-ethylamino)methyl)-furan-2-yl)-quinolin-4-yl)-amine;
(4-(3-Fluorobenzyloxy)-phenyl)-(7-(4-((2-methanesulphonyl-ethylamino)methyl)-furan-2-yl)-quinolin-4-yl)-amine;
(4-Benzenesulphonyl-phenyl)-(7-(4-((2-methanesulphonyl-ethylamino)-methyl)-furan-2-yl)-quinolin-4-yl)-amine;
(4-Benzyloxy-phenyl)-(7-(4-((2-methanesulphony-ethylamino)methyl)-furan-2-yl)-quinolin-4-yl)-amine;
(4-Phenoxy-phenyl)-(7-(4-((2-methanesulphonyl-ethylamino)methyl)-furan-2-yl)-quinolin-4-yl)-amine;

In a particular embodiment, EGFR inhibitors are compound of formula III selected from the group consisting of:
(1-Benzyl-1H-indazol-5-yl)-(7-(2-((2-methanesulphonyl-ethylamino)methyl)-thiazol-4-yl)-quinolin-4-yl)-amine;
(4-(4-Fluorobenzyloxy)-phenyl)-(7-(2-((2-methanesulphonyl-ethylamino)methyl)-thiazol-4-yl)-quinolin-4-yl)-amine;
(4-(3-Fluorobenzyloxy)-phenyl)-(7-(2-((2-methanesulphonyl-ethylamino)methyl)-thiazol-4-yl)-quinolin-4-yl)-amine;
(4-Benzenesulphonyl-phenyl)-(7-(2-((2-methanesulphonyl-ethylamino)-methyl)-thiazol-4-yl)-quinolin-4-yl)-amine;
(4-Benzyloxy-phenyl)-(7-(2-((2-methanesulphonyl-ethylamino)methyl)-thiazol-4-yl)-quinolin-4-yl)-amine;
(4-Phenoxy-phenyl)-(7-(2-((2-methanesulphonyl-ethylamino)methyl)-thiazol-4-yl)-quinolin-4-yl)-amine;

In a particular embodiment, EGFR inhibitors are compound of formula III selected from the group consisting of:
(1-Benzyl-1H-indazol-5-yl)-(7-(2-((2-methanesulphonyl-ethylamino)methyl)-thiazol-5-yl)-quinolin-4-yl)-amine;
(4-(4-Fluorobenzyloxy)-phenyl)-(7-(2-((2-methanesulphonyl-ethylamino)methyl)-thiazol-5-yl)-quinolin-4-yl)-amine;
(4-(3-Fluorobenzyloxy)-phenyl)-(7-(2-((2-methanesulphonyl-ethylamino)methyl)-thiazol-5-yl)-quinolin-4-yl)-amine;
(4-Benzenesulphonyl-phenyl)-(7-(2-((2-methanesulphonyl-ethylamino)-methyl)-thiazol-5-yl)-quinolin-4-yl)-amine;
(4-Benzyloxy-phenyl)-(7-(2-((2-methanesulphonyl-ethylamino)methyl)-thiazol-5-yl)-quinolin-4-yl)-amine;
(4-Phenoxy-phenyl)-(7-(2-((2-methanesulphonyl-ethylamino)methyl)-thiazol-5-yl)-quinolin-4-yl)-amine;

In a particular embodiment, EGFR inhibitors are compound of formula III selected from the group consisting of:
(1-Benzyl-1H-indazol-5-yl)-(7-(4-((2-methanesulphonyl-ethylamino)methyl)-thiazol-2-yl)-quinolin-4-yl)-amine;
(4-(4-Fluorobenzyloxy)-phenyl)-(7-(4-((2-methanesulphonyl-ethylamino)methyl)-thiazol-2-yl)-quinolin-4-yl)-amine;
(4-(3-Fluorobenzyloxy)-phenyl)-(7-(4-((2-methanesulphonyl-ethylamino)methyl)-thiazol-2-yl)-quinolin-4-yl)-amine;
(4-Benzenesulphonyl-phenyl)-(7-(4-((2-methanesulphonyl-ethylamino)-methyl)-thiazol-2-yl)-quinolin-4-yl)-amine;
(4-Benzyloxy-phenyl)-(7-(4-((2-methanesulphonyl-ethylamino)methyl)-thiazol-2-yl)-quinolin-4-yl)-amine;
(4-Phenoxy-phenyl)-(7-(4-((2-methanesulphonyl-ethylamino)methyl)-thiazol-2-yl)-quinolin-4-yl)-amine;

In a particular embodiment, EGFR inhibitors are compound of formula III selected from the group consisting of:
(1-Benzyl-1H-indazol-5-yl)-(7-(5-((2-methanesulphonyl-ethylamino)methyl)-thiazol-2-yl)-quinolin-4-yl)-amine;
(4-(4-Fluorobenzyloxy)-phenyl)-(7-(5-((2-methanesulphonyl-ethylamino)methyl)-thiazol-2-yl)-quinolin-4-yl)-amine;
(4-(3-Fluorobenzyloxy)-phenyl)-(7-(5-((2-methanesulphonyl-ethylamino)methyl)-thiazol-2-yl)-quinolin-4-yl)-amine;
(4-Benzenesulphonyl-phenyl)-(7-(5-((2-methanesulphonyl-ethylamino)-methyl)-thiazol-2-yl)-quinolin-4-yl)-amine;

(4-Benzyloxy-phenyl)-(7-(5-((2-methanesulphonyl-ethylamino)methyl)-thiazol-2-yl)-quinolin-4-yl)-amine;
(4-Phenoxy-phenyl)-(7-(5-((2-methanesulphonyl-ethylamino)methyl)-thiazol-2-yl)-quinolin-4-yl)-amine;

In a particular embodiment, EGFR inhibitors are compound of formula III selected from the group consisting of:
(1-Benzyl-1H-indazol-5-yl)-(7-(3-((2-methanesulphonyl-ethylamino)methyl)-phenyl)-quinolin-4-yl)-amine;
(4-(4-Fluorobenzyloxy)-phenyl)-(7-(3-((2-methanesulphonyl-ethylamino)methyl)-phenyl)-quinolin-4-yl)-amine;
(4-(3-Fluorobenzyloxy)-phenyl)-(7-(3-((2-methanesulphonyl-ethylamino)methyl)-phenyl)-quinolin-4-yl)-amine;
(4-Benzenesulphonyl-phenyl)-(7-(3-((2-methanesulphonyl-ethylamino)-methyl)-phenyl)-quinolin-4-yl)-amine;
(4-Benzyloxy-phenyl)-(7-(3-((2-methanesulphonyl-ethylamino)-methyl)-phenyl)-quinolin-4-yl)-amine;
(4-Phenoxy-phenyl)-(7-(3-((2-methanesulphonyl-ethylamino)-methyl)-phenyl)-quinolin-4-yl)-amine;

In a particular embodiment, EGFR inhibitors are compound of formula III selected from the group consisting of:
(1-Benzyl-1H-indazol-5-yl)-(7-(4-((2-methanesulphonyl-ethylamino)methyl)-phenyl)-quinolin-4-yl)-amine;
(4-(4-Fluorobenzyloxy)-phenyl)-(7-(4-((2-methanesulphonyl-ethylamino)methyl)-phenyl)-quinolin-4-yl)-amine;
(4-(3-Fluorobenzyloxy)-phenyl)-(7-(4-((2-methanesulphonyl-ethylamino)methyl)-phenyl)-quinolin-4-yl)-amine;
(4-Benzenesulphonyl-phenyl)-(7-(4-((2-methanesulphonyl-ethylamino)-methyl)-phenyl)-quinolin-4-yl)-amine;
(4-Benzyloxy-phenyl)-(7-(4-((2-methanesulphonyl-ethylamino)-methyl)-phenyl)-quinolin-4-yl)-amine;
(4-Phenoxy-phenyl)-(7-(4-((2-methanesulphonyl-ethylamino)-methyl)-phenyl)-quinolin-4-yl)-amine;

In a particular embodiment, EGFR inhibitors are compound of formula III selected from the group consisting of:
(4-Benzyloxy-3-chlorophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy)-3-chlorophenyl)-(6-(5-((2-methanesulphonyl-ethylamino)methyl)-furan-2-yl)-pyrido[3,4-d]pyrimidin-4-yl)-amine;
(4-Benzyloxy-3-trifluoromethylphenyl)-(6-(5-((2-methanesulphonyl-ethylamino)methyl)-furan-2-yl)-pyrido[3,4-d]pyrimidin-4-yl)-amine;
(4-(3-Fluoro-benzyloxy)-3-trifluoromethylphenyl)-(6-(5-((2-methanesulphonyl-ethylamino)-methyl)-furan-2-yl)-pyrido[3,4-d]pyrimidin-4-yl)-amine;
(4-Benzyloxy-3-bromophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy-3-bromophenyl)-(6-(5-((2-methanesulphonyl-ethylamino)methyl)-furan-2-yl)-pyrido[3,4-d]pyrimidin-4-yl)-amine;
(4-Benzyloxy-3-iodophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy-3-iodophenyl)-(6-(5-((2-methanesulphonyl-ethylamino)methyl)-furan-2-yl)-pyrido[3,4-d]pyrimidin-4-yl)-amine;
(4-Benzyloxy-3-fluorophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy-3-fluorophenyl)-(6-(5-((2-methanesulphonyl-ethylamino)methyl)-furan-2-yl)-pyrido[3,4-d]pyrimidin-4-yl)-amine;

In a particular embodiment, EGFR inhibitors are compound of formula III selected from the group consisting of:
(4-Benzyloxy-3-chlorophenyl)-(6-(2-((2-methanesulphonyl-ethylamino)methyl)-thiazol-4-yl)-pyrido[3,4-d]pyrimidin-4-yl)-amine;
(4-(3-Fluoro-benzyloxy)-3-chlorophenyl)-(6-(2-((2-methanesulphonyl-ethylamino)methyl)-thiazol-4-yl)-pyrido[3,4-d]pyrimidin-4-yl)-amine;
(4-Benzyloxy-3-trifluoromethylphenyl)-(6-(2-((2-methanesulphonyl-ethylamino)methyl)-thiazol-4-yl)-pyrido[3,4-d]pyrimidin-4-yl)-amine;
(4-(3-Fluoro-benzyloxy)-3-trifluoromethylphenyl)-(6-(2-((2-methanesulphonyl-ethylamino)methyl)-thiazol-4-yl)-pyrido[3,4-d]pyrimidin-4-yl)-amine;
(4-Benzyloxy-3-bromophenyl)-(6-(2-((2-methanesulphonyl-ethylamino)methyl)-thiazol-4-yl)-pyrido[3,4-d]pyrimidin-4-yl)-amine;
(4-(3-Fluoro-benzyloxy-3-bromophenyl)-(6-(2-((2-methanesulphonyl-ethylamino)methyl)-thiazol-4-yl)-pyrido[3,4-d]pyrimidin-4-yl)-amine;
(4-Benzyloxy-3-iodophenyl)-(6(2-methanesulphonyl-ethylamino)methyl)-thiazol-4-yl)-pyrido[3,4-d]pyrimidin-4-yl)-amine;
(4-(3-Fluoro-benzyloxy-3-iodophenyl)-(6-(2-((2-methanesulphonyl-ethylamino)methyl)-thiazol-4-yl)-pyrido[3,4-d]pyrimidin-4-yl)-amine;
(4-Benzyloxy-3-fluorophenyl)-(6-(2-((2-methanesulphonyl-ethylamino)methyl)-thiazol-4-yl)-pyrido[3,4-d]pyrimidin-4-yl)-amine;
(4-(3-Fluoro-benzyloxy-3-fluorophenyl)-(6-(2-((2-methanesulphonyl-ethylamino)methyl)-thiazol-4-yl)-pyrido[3,4-d]pyrimidin-4-yl)-amine;

In a particular embodiment, EGFR inhibitors are compound of formula III selected from the group consisting of:
(4-Benzyloxy-3-chlorophenyl)-(6-(2-((2-methanesulphony-ethylamino)methyl)-thiazol-4-yl)-quinazolin-4-yl)-amine
(4-(3-Fluoro-benzyloxy)-3-chlorophenyl)-(6-(2-((2-methanesulphonyl-ethylamino)methyl)-thiazol-4-yl)-quinazolin-4-yl)-amine;
(4-Benzyloxy-3-trifluoromethylphenyl)-(6-(2-((2-methanesulphonyl-ethylamino)methyl)-thiazol-4-yl)-quinazolin-4-yl)-amine;
(4-(3-Fluoro-benzyloxy)-3-trifluoromethylphenyl)-(6-(2-((2-methanesulphonyl-ethylamino)methyl)-thiazol-4-yl)-quinazolin-4-yl)-amine;
(4-Benzyloxy-3-bromophenyl)-(6-(2-((2-methanesulphonyl-ethylamino)methyl)-thiazol-4-yl)-quinazolin-4-yl)-amine;
(4-(3-Fluoro-benzyloxy-3-bromophenyl)-(6-(2-((2-methanesulphonyl-ethylamino)methyl)-thiazol-4-yl)-quinazolin-4-yl)-amine;
(4-Benzyloxy-3-iodophenyl)-(6-(2-((2-methanesulphonyl-ethylamino)methyl)-thiazol-4-yl)-quinazolin-4-yl)-amine;
(4-(3-Fluoro-benzyloxy-3-iodophenyl)-(6-(2-((2-methanesulphonyl-ethylamino)methyl)-thiazol-4-yl)-quinazolin-4-yl)-amine;

In a particular embodiment, EGFR inhibitors are compound of formula III selected from the group consisting of:
(4-(3-Fluoro-benzyloxy)-3-trifluoromethylphenyl)-(6-(5-((2-methanesulphonyl-ethylamino)-methyl)-furan-2-yl)-quinazolin-4-yl)-amine;
(4-Benzyloxy-3-bromophenyl)-(6-(5-((2-methanesulphonyl-ethylamino)-methyl)-furan-2-yl)-quinazolin-4-yl)-amine;
(4-(3-Fluoro-benzyloxy-3-bromophenyl)-(6-(5-((2-methanesulphonyl-ethylamino)-methyl)-furan-2-yl)-quinazolin-4-yl)-amine;

(4-Benzyloxy-3-iodophenyl)-(6-(5-((2-methanesulphonyl-ethylamino)-methyl)-furan-2-yl)-quinazolin-4-yl)-amine;
(4-(3-Fluoro-benzyloxy-3-iodophenyl)-(6-(5-((2-methanesulphonyl-ethylamino)-methyl)-furan-2-yl)-quinazolin-4-yl)-amine.

In a particular embodiment, EGFR inhibitors are compound of formula III selected from the group consisting of:
N-[4-(Benzyloxy)-3-chlorophenyl]-7-methoxy-6-[5-({[2-(methanesulphonyl)ethyl]amino}methyl)-2-furyl]-4-quinazolinamine;
N-[4-(3-Fluoro-benzyloxy)-3-chlorophenyl]-7-methoxy-6-[5-({[2-(methanesulphonyl)ethyl]amino}methyl)-2-furyl]-4-quinazolinamine;
N-[4-Benzyloxy-3-trifluoromethylphenyl]-7-methoxy-6-[5-({[2-(methanesulphonyl)ethyl]amino}methyl)-2-furyl]-4-quinazolinamine;
N-[4-(3-Fluoro-benzyloxy)-3-trifluoromethylphenyl]-7-methoxy-6-[5-({[2-(methanesulphonyl)ethyl]amino}methyl)-2-furyl]-4-quinazolinamine;
N-[4-Benzyloxy-3-bromophenyl]-7-methoxy-6-[5-({[2-(methanesulphonyl)ethyl]amino}methyl)-2-furyl]-4-quinazolinamine;
N-[4-(3-Fluoro-benzyloxy-3-bromophenyl]-7-methoxy-6-[5-({[2-(methanesulphonyl)ethyl]amino}methyl)-2-furyl]-4-quinazolinamine;
N-[4-Benzyloxy-3-iodophenyl]-7-methoxy-6-[5-({[2-(methanesulphonyl)ethyl]amino}methyl)-2-furyl]-4-quinazolinamine;
N-[4-(3-Fluoro-benzyloxy-3-iodophenyl]-7-methoxy-6-[5-({[2-(methanesulphonyl)ethyl]amino}methyl)-2-furyl]-4-quinazolinamine;
N-[4-Benzyloxy-3-fluorophenyl]-7-methoxy-6-[5-({[2-(methanesulphonyl)ethyl]amino}methyl)-2-furyl]-4-quinazolinamine;
N-[4-(3-Fluoro-benzyloxy-3-fluorophenyl]-7-methoxy-6-[5-({[2-(methanesulphonyl)ethyl]amino}methyl)-2-furyl]-4-quinazolinamine;
N-[1-(3-Fluorobenzyl-1H-indazol-5-yl]-7-methoxy-6-[5-({[2-(methanesulphonyl)ethyl]amino}methyl)-2-furyl]-4-quinazolinamine;

In a particular embodiment, EGFR inhibitors are compound of formula III selected from the group consisting of:
N-[4-(Benzyloxy)-3-chlorophenyl]-7-fluoro-6-[5-({[2-(methanesulphonyl)ethyl]amino}methyl)-2-furyl]-4-quinazolinamine;
N-[4-(3-Fluoro-benzyloxy)-3-chlorophenyl]-7-fluoro-6-[5-({[2-(methanesulphonyl)ethyl]amino}methyl)-2-furyl]-4-quinazolinamine
N-[4-Benzyloxy-3-trifluoromethylphenyl]-7-fluoro-6-[5-({[2-(methanesulphonyl)ethyl]amino}methyl)-2-furyl]-4-quinazolinamine
N-[4-(3-Fluoro-benzyloxy)-3-trifluoromethylphenyl]-7-fluoro-6-[5-({[2-(methanesulphonyl)ethyl]amino}methyl)-2-furyl]-4-quinazolinamine
N-[4-Benzyloxy-3-bromophenyl]-7-fluoro-6-[5-({[2-(methanesulphonyl)ethyl]amino}methyl)-2-furyl]-4-quinazolinamine
N-[4-(3-Fluoro-benzyloxy-3-bromophenyl]-7-fluoro-6-[5-({[2-(methanesulphonyl)ethyl]amino}methyl)-2-furyl]-4-quinazolinamine
N-[4-Benzyloxy-3-iodophenyl]-7-fluoro-6-[5-({[2-(methanesulphonyl)ethyl]amino}methyl)-2-furyl]-4-quinazolinamine
N-[4-(3-Fluoro-benzyloxy-3-iodophenyl]-7-fluoro-6-[5-({[2-(methanesulphonyl)ethyl]amino}methyl)-2-furyl]-4-quinazolinamine
N-[4-Benzyloxy-3-fluorophenyl]-7-fluoro-6-[5-({[2-(methanesulphonyl)ethyl]amino}methyl)-2-furyl]-4-quinazolinamine
N-[4-(3-Fluoro-benzyloxy-3-fluorophenyl]-7-fluoro-6-[5-({[2-(methanesulphonyl)ethyl]amino}methyl)-2-furyl]-4-quinazolinamine
N-[1-(3-fluorobenzyl-1H-indazol-5-yl]-7-fluoro-6-[5-({[2-(methanesulphonyl)ethyl]amino}methyl)-2-furyl]-4-quinazolinamine In a particular embodiment, EGFR inhibitors are compound of formula III selected from the group consisting of:
N-[4-(benzyloxy)-3-chlorophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy)-3-chlorophenyl]-7-methoxy-6-[2-({[2-(methanesulphonyl)ethyl]amino}methyl)-1,3-thiazol-4-yl]-4-quinazolinamine;
N-[4-Benzyloxy-3-trifluoromethylphenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy)-3-trifluoromethylphenyl]-7-methoxy-6-[2-({[2-(methanesulphonyl)ethyl]amino}methyl)-1,3-thiazol-4-yl]-4-quinazolinamine;
N-[4-Benzyloxy-3-bromophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy-3-bromophenyl]-7-methoxy-6-[2-({[2-(methanesulphonyl)ethyl]amino}methyl)-1,3-thiazol-4-yl]-4-quinazolinamine;
N-[4-Benzyloxy-3-iodophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy-3-iodophenyl]-7-methoxy-6-[2-({[2-(methanesulphonyl)ethyl]amino}methyl)-1,3-thiazol-4-yl]-4-quinazolinamine;
N-[4-Benzyloxy-3-fluorophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy-3-fluorophenyl]-7-methoxy-6-[2-({[2-(methanesulphonyl)ethyl]amino}methyl)-1,3-thiazol-4-yl]-4-quinazolinamine;
N-[1-(3-fluorobenzyl-1H-indazol-5-yl]-7-methoxy-6-[2-({[2-(methanesulphonyl)ethyl]amino}methyl)-1,3-thiazol-4-yl]-4-quinazolinamine.

In a particular embodiment, EGFR inhibitors are compound of formula III selected from the group consisting of:
N-[4-(benzyloxy)-3-chlorophenyl]-7-fluoro-6-[2-({[2-(methanesulphonyl)ethyl]amino}methyl)-1,3-thiazol-4-yl]-4-quinazolinamine;
N-[4-(3-Fluoro-benzyloxy)-3-chlorophenyl]-7-fluoro-6-[2-({[2-(methanesulphonyl)ethyl]amino}methyl)-1,3-thiazol-4-yl]-4-quinazolinamine;
N-[4-Benzyloxy-3-trifluoromethylphenyl]-7-fluoro-6-[2-({[2-(methanesulphonyl)ethyl]amino}methyl)-1,3-thiazol-4-yl]-4-quinazolinamine;
N-[4-(3-Fluoro-benzyloxy)-3-trifluoromethylphenyl]-7-fluoro-6-[2-({[2-(methanesulphonyl)ethyl]amino}methyl)-1,3-thiazol-4-yl]-4-quinazolinamine;
N-[4-Benzyloxy-3-bromophenyl]-7-fluoro-6-[2-({[2-(methanesulphonyl)ethyl]amino}methyl)-1,3-thiazol-4-yl]-4-quinazolinamine;
N-[4-(3-Fluoro-benzyloxy-3-bromophenyl]-7-fluoro-6-[2-({[2-(methanesulphonyl)ethyl]amino}methyl)-1,3-thiazol-4-yl]-4-quinazolinamine;
N-[4-Benzyloxy-3-iodophenyl]-7-fluoro-6-[2-({[2-(methanesulphonyl)ethyl]amino}methyl)-1,3-thiazol-4-yl]-4-quinazolinamine;

N-[4-(3-Fluoro-benzyloxy-3-iodophenyl]-7-fluoro-6-[2-({[2-(methanesulphonyl)ethyl]amino}methyl)-1,3-thiazol-4-yl]-4-quinazolinamine;

N-[4-Benzyloxy-3-fluorophenyl]-7-fluoro-6-[2-({[2-(methanesulphonyl)ethyl]amino}methyl)-1,3-thiazol-4-yl]-4-quinazolinamine; 2 N-[4-(3-Fluoro-benzyloxy-3-fluorophenyl]-7-fluoro-6-[2-({[2-(methanesulphonyl)ethyl]amino}methyl)-1,3-thiazol-4-yl]-4-quinazolinamine;

N-[1-(3-fluorobenzyl-1H-indazol-5-yl]-7-fluoro-6-[2-({[2-(methanesulphonyl)ethyl]amino}methyl)-1,3-thiazol-4-yl]-4-quinazolinamine;

and salts or solvates thereof, particularly pharmaceutically acceptable salts or solvates thereof.

In a particular embodiment, EGFR inhibitors are compound of formula III selected from the group consisting of:

(4-(3-Fluorobenzyloxy)-phenyl)-(6-(5-((2-methanesulphonyl-ethylamino)methyl)-furan-2-yl)-pyrido[3,4-d]pyrimidin-4-yl)-amine;

(4-Benzyloxyphenyl)-(6-(5-((2-methanesulphonyl-ethylamino)-methyl)-furan-2-yl)-quinazolin-4-yl)-amine;

N-{4-[(3-Fluorobenzyl)oxy]phenyl}-6-[5-({[2-(methanesulphonyl)ethyl]amino}methyl)-2-furyl]-4-quinazolinamine;

N-[4-(Benzyloxy)phenyl]-7-methoxy-6-[5-({[2-(methanesulphonyl)ethyl]amino}methyl)-2-furyl]-4-quinazolinamine;

N-(1-Benzyl-1H-indazol-5-yl)-7-methoxy-6-[5-({[2-(methanesulphonyl)ethyl]amino}methyl)-2-furyl]-4-quinazolinamine;

N-{3-Fluoro-4-[(3-fluorobenzyl)oxy]phenyl}-6-[5-({[2-(methanesulphonyl)ethyl]amino}methyl)-2-furyl]-4-quinazolinamine;

N-[1-(3-Fluorobenzyl)-1H-indazol-5-yl]-6-[2-({[2-(methanesulphonyl)ethyl]amino}methyl)-1,3-thiazol-4-yl]-4-quinazolinamine;

6-[5-({[2-(Methanesulphonyl)ethyl]amino}methyl)-2-furyl]-N-[4-(benzenesulphonyl)phenyl]-4-quinazolinamine;

N-{3-Fluoro-4-[(3-fluorobenzyl)oxy]phenyl}-6-[2-({[2-(methanesulphonyl)ethyl]amino}methyl)-1,3-thiazol-4-yl]-4-quinazolinamine;

N-(1-Benzyl-1H-indazol-5-yl)-6-[2-({[2-(methanesulphonyl)ethyl]amino}methyl)-1,3-thiazol-4-yl]-4-quinazolinamine;

N-(3-Fluoro-4-benzyloxyphenyl)-6-[5-({[2-(methanesulphonyl)ethyl]amino}methyl)-4-furyl]-4-quinazolinamine;

N-(3-Chloro-4-benzyloxyphenyl)-6-[2-({[2-(methanesulphonyl)ethyl]amino}methyl)-4-furyl]-4-quinazolinamine;

N-{3-Chloro-4-[(3-fluorobenzyl)oxy]phenyl}-6-[5-({[2-(methanesulphonyl)ethyl]amino}methyl)-2-furyl]-4-quinazolinamine;

N-(1-Benzyl-1H-indazol-5-yl)-7-fluoro-6-[5-({[2-(methanesulphonyl)ethyl]amino}methyl)-2-furyl]-4-quinazolinamine;

N-(3-Trifluoromethyl-4-benzyloxyphenyl)-6-[5-({[2-(methanesulphonyl)ethyl]amino}methyl)-4-furyl]-4-quinazolinamine;

and salts or solvates thereof, particularly pharmaceutically acceptable salts or solvates thereof.

In a particular embodiment, EGFR inhibitors are compound of formula III selected from the group consisting of:

(4-Phenoxyphenyl)-(7-(2-(2-methanesulphonyl)ethylaminomethyl)thiazol-4-yl)-quinolin-4-yl)amine;

(4-Phenoxyphenyl)-(7-(4-(2-methanesulphonyl)ethylaminomethyl)thiazol-5-yl)-quinolin-4-yl)amine;

(4-Phenoxyphenyl)-(7-(5-(2-(methanesulphonyl)ethylaminomethyl)furan-2-yl)-quinolin-4-yl)amine;

and salts or solvates thereof, particularly pharmaceutically acceptable salts or solvates thereof.

In a particular embodiment, EGFR inhibitors are compound of formula III selected from the group consisting of:

(4-Phenoxy-phenyl)-(7-(5-((2-methanesulphonyl-ethylamino)methyl)-furan-2-yl)-quinazolin-4-yl)-amine;

(4-Phenoxy-phenyl)-(7-(4-((2-methanesulphonyl-ethylamino)methyl)-furan-2-yl)-quinazolin-4-yl)-amine;

(4-Phenoxy-phenyl)-(7-(2-((2-methanesulphonyl-ethylamino)methyl)-thiazol-4-yl)-quinazolin-4-yl)-amine;

(4-Phenoxy-phenyl)-(7-(2-((2-methanesulphonyl-ethylamino)methyl)-thiazol-5-yl)-quinazolin-4-yl)-amine;

(4-Phenoxy-phenyl)-(7-(4-((2-methanesulphonyl-ethylamino)methyl)-thiazol-2-yl)-quinazolin-4-yl)-amine;

(4-Phenoxy-phenyl)-(7-(5-((2-methanesulphonyl-ethylamino)methyl)-thiazol-2-yl)-quinazolin-4-yl)-amine;

(4-Phenoxy-phenyl)-(7-(3-((2-methanesulphonyl-ethylamino)methyl)-phenyl)-quinazolin-4-yl)-amine;

(4-Phenoxy-phenyl)-(7-(4-((2-methanesulphonyl-ethylamino)methyl)-phenyl)-quinazolin-4-yl)-amine;

(4-Phenoxy-phenyl)-(7-(5-((2-methanesulphonyl-ethylamino)methyl)-furan-2-yl)-quinolin-4-yl)-amine;

(4-Phenoxy-phenyl)-(7-(4-((2-methanesulphonyl-ethylamino)methyl)-furan-2-yl)-quinolin-4-yl)-amine;

(4-Phenoxy-phenyl)-(7-(2-((2-methanesulphonyl-ethylamino)methyl)-thiazol-4-yl)-quinolin-4-yl)-amine;

(4-Phenoxy-phenyl)-(7-(2-((2-methanesulphonyl-ethylamino)methyl)-thiazol-5-yl)-quinolin-4-yl)-amine;

(4-Phenoxy-phenyl)-(7-(4-((2-methanesulphonyl-ethylamino)methyl)-thiazol-2-yl)-quinolin-4-yl)-amine;

(4-Phenoxy-phenyl)-(7-(5-((2-methanesulphonyl-ethylamino)methyl)-thiazol-2-yl)-quinolin-4-yl)-amine;

(4-Phenoxy-phenyl)-(7-(3-((2-methanesulphonyl-ethylamino)methyl)-phenyl)-quinolin-4-yl)-amine;

(4-Phenoxy-phenyl)-(7-(4-((2-methanesulphonyl-ethylamino)methyl)-phenyl)-quinolin-4-yl)-amine;

and salts or solvates thereof, particularly pharmaceutically acceptable salts or solvates thereof.

In a particular embodiment, EGFR inhibitors are compound of formula III selected from the group consisting of:

(4-Phenoxy-phenyl)-(7-(2-((2-methanesulphonyl-ethylamino)methyl)-thiazol-4-yl)-quinolin-4-yl)-amine;

(4-Phenoxy-phenyl)-(7-(2-((2-methanesulphonyl-ethylamino)methyl)-thiazol-5-yl)-quinolin-4-yl)-amine;

(4-Phenoxy-phenyl)-(7-(4-((2-methanesulphonyl-ethylamino)methyl)-thiazol-2-yl)-quinolin-4-yl)-amine;

(4-Phenoxy-phenyl)-(7-(5-((2-methanesulphonyl-ethylamino)methyl)-thiazol-2-yl)-quinolin-4-yl)-amine;

and salts or solvates thereof, particularly pharmaceutically acceptable salts or solvates thereof.

Examples of EGFR inhibitors also include antibodies that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); IMC-11F8, a fully human, EGFR-targeted antibody (ImClone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMI 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., *J. Biol. Chem.* 279(29): 30375-30384 (2004)). The EGFR antibody may be conjugated with a cytotoxic agent, thus generating an immunoconjugate (see, e.g., EP659,439A2, Merck Patent GmbH).

Cetuximab (ERBITUX, ImClone), a monoclonal antibody that has been approved by the Food and Drug Administration as a therapeutic for advanced-stage colorectal cancers that have spread to other parts of the body. Cetuximab targets one of the ligand binding domains of EGFR, keeping EGFR in a closed configuration, thus preventing structural rearrangement and ligand activation of the receptor. Accordingly, cetuximab blocks the formation of homo- and heterodimers containing EGFR. See also, Hubbard, *Cancer Cell.* 7(4): 287-8 (2005).

3. Preparation of Antibodies

Antibodies or other molecules with the desired properties, including HER2 dimerization inhibitors and EGFR inhibitors, can be made, tested and used by methods well known in the art.

What follows is a description of exemplary techniques for the production of antibodies that can be used in accordance with the present invention. While the description is generally directed to the production of HER2 antibodies, one of skill in the art can readily adapt the disclosure to produce antibodies against any of the ErbB receptors.

The HER2 antigen to be used for production of antibodies may be, e.g., a soluble form of the extracellular domain of HER2 or a portion thereof, containing the desired epitope. Alternatively, cells expressing HER2 at their cell surface (e.g. NIH-3T3 cells transformed to overexpress HER2; or a carcinoma cell line such as SK-BR-3 cells, see Stancovski et al. PNAS (USA) 88:8691-8695 (1991)) can be used to generate antibodies. Other forms of HER2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R1N=C=NR$, where R and R1 are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs., 130: 151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., Proc. Natl. Acad. Sci. USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The methods of the present invention employ HER2 dimerization inhibitors, including antibodies which block the formation of HER2 dimers, such as HER homo- and heterodimers. In addition, the present invention employs EGFR inhibitors.

Exemplary humanized HER2 antibodies which bind HER2 and block ligand activation of an ErbB receptor are described in WO 01/00245, which is incorporated herein by reference. The humanized antibodies of particular interest herein block EGF, TGF-α and/or HRG mediated HER2 heterodimer formation essentially as effectively as murine monoclonal antibody 2C4 (or a Fab fragment thereof) and/or bind HER2 essentially as effectively as murine monoclonal antibody 2C4 (or a Fab fragment thereof). The humanized antibodies herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., Sequences of Proteins of Immunological Interest, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX, where X is preferably D or S (SEQ ID NO: 17); DVNPNSGGSIYNQRFKG (SEQ ID NO: 18); and/or NLGPSFYFDY (SEQ ID NO: 19), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy domain amino acid sequence in SEQ ID NO: 8 (FIG. 2B).

The humanized antibody may comprise variable light domain complementarity determining residues KASQD-VSIGVA (SEQ ID NO:20); SASYX1X2X3 (SEQ ID NO: 21), where X1 is preferably R or L, X2 is preferably Y or E, and X3 is preferably T or S; and/or QQYYIYPYT (SEQ ID NO:22), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light domain amino acid sequence in SEQ ID NO: 11 (FIG. 2A).

The present application also contemplates affinity matured antibodies which bind HER2 and block ligand activation of an ErbB receptor. The parent antibody may be a human antibody or a humanized antibody, e.g., one comprising the variable light and/or heavy sequences of SEQ ID Nos. 13 and 14, respectively (i.e. variant 574; FIGS. 5A and B). The affinity matured antibody preferably binds to HER2 receptor with an affinity superior to that of murine 2C4 or variant 574 (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

With regard to all antibodies used in practicing the present invention, various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

Preferred humanized EGFR inhibitor antibodies herein include humanized antibodies derived from the murine antibody designated "225," which are described in U.S. Pat. No. 4,943,533, which is incorporated by reference in its entirety. Humanized 225 antibodies can, for example, be prepared by following the method described in PCT application publication No. WO 96/40,210.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589, 369 and 5,545,807.

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573, 905.

As discussed above, human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a linear antibody, e.g., as described in U.S. Pat. No. 5,641, 870 for example. Such linear antibody fragments may be monospecific or bispecific.

For example, single-chain antibodies, including single-chain EGFR (Fv225) antibodies, can be made following methods described in EP 502,812 and Wels et al., *Int. J. Cancer* 137-144 (1995).

(vi) Bispecific Antibodies

Bispecific antibodies are antibodies that have binding specificities for at least two different epitopes. Exemplary bispecific antibodies may bind to two different epitopes of the HER2 protein. Other such antibodies may combine an HER2 binding site with binding site(s) for EGFR, HER3 and/or HER4. Alternatively, an HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγII (CD32) and FcγRIII (CD16) so as to focus cellular defense mechanisms to the HER2-expressing cell. Bispecific antibodies may also be used to localize cytotoxic agents to cells which express HER2. These antibodies possess an HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')2 bispecific antibodies).

WO 96/16673 describes a bispecific HER2/anti-FcγRIII antibody and U.S. Pat. No. 5,837,234 discloses a bispecific HER2/anti-FcγRI antibody. A bispecific HER2/Fca antibody is shown in WO98/02463. U.S. Pat. No. 5,821,337 teaches a bispecific HER2/anti-CD3 antibody.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.,* 175: 217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

(vii) Other Amino Acid Sequence Modifications

Amino acid sequence modification(s) of the EGFR and HER2 antibodies are contemplated. For example, it may be desirable to improve the binding affinity and/or other biological properties of the antibodies. Amino acid sequence variants of the EGFR and HER2 antibodies are prepared by introducing appropriate nucleotide changes into the EGFR or HER2 antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibodies, such as changing the number or position of glycosylation sites.

A useful method for identification of certain residues or regions of the HER2 or EGFR antibodies that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with HER2 or EGFR antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed HER2 or EGFR antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants include the fusion to the N- or C-terminus of the antibodies to a reporter molecule, an enzyme (e.g. for ADEPT) or a polypeptide which increases the serum half-life of the antibody.

Another type of variant is an amino acid substitution variant. These variants have at least one amino acid residue in the starting antibody molecule replaced by a different residue. The sites of greatest interest for substitutional mutagenesis include the hypervariable regions, but FR alterations are also contemplated. Conservative substitutions are shown in Table 1 under the heading of "preferred substitutions." If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the starting antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variation alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibodies herein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the particular antibody.

It may be desirable to modify the antibodies of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues).

Engineered antibodies with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

(viii) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, an antibody is conjugated to one or more maytansine molecules (e.g.

about 1 to about 10 maytansine molecules per antibody molecule). Maytansine may, for example, be converted to May-SS-Me which may be reduced to May-SH3 and reacted with modified antibody (Chari et al. Cancer Research 52: 127-131 (1992)) to generate a maytansinoid-antibody immunoconjugate.

Another immunoconjugate of interest comprises an HER2 antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, γ1I, α2I, α3I, N-acetyl-γ1I, PSAG and θI1 (Hinman et al. Cancer Research 53: 3336-3342 (1993) and Lode et al. Cancer Research 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated antibodies, such as, for example, HER2 and EGFR antibodies. Examples include At211, I131, I125, Y90, Re186, Re188, Sm153, Bi212, P32 and radioactive isotopes of Lu.

Conjugates of an antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a cleavable linker facilitating release of the cytotoxic drug in the cell. For example, an acid-labile linker, peptidase-sensitive linker, dimethyl linker or disulfide-containing linker (Chari, et al. Cancer Research 52: 127-131 (1992)) may be used.

Alternatively, a fusion protein comprising an HER2 antibody and cytotoxic agent may be made, e.g. by recombinant techniques or peptide synthesis.

In yet another embodiment, an antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes," can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

The enzymes can be covalently bound to the target antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

(xii) Other Antibody Modifications

Other modifications of the antibodies are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody may also or alternatively be linked to one or more of a variety of different moieties, such as a fluorescent lable, a moiety with a known electrophoretic mobility, or a moiety that is able to cleave a specific linker molecule.

The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies used in the method of the present invention may also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19) 1484 (1989).

IV. IDENTIFICATION OF PATIENTS FOR TREATMENT

It is contemplated that, according to the present invention, patients diagnosed with an EGFR positive and HER2 positive tumor characterized by the presence of HER2 heterodimers may be treated with a combination of EGFR inhibitors and HER dimerization inhibitors.

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer to be treated herein may be one characterized by excessive activation of an ErbB receptor, in particular EGFR and/or HER2. Such excessive activation may be attributable to overexpression or increased production of the EGFR and/or HER2 receptor or a EGFR and/or HER2 ligand.

While the cancer may be characterized by overexpression of the EGFR and/or HER2 receptor, the present application further provides a method for treating cancer which is not considered to be a EGFR and/or HER2-overexpressing cancer.

Examples of cancers which may express/overexpress EGFR include squamous cell cancer (e.g. epithelial squamous cell cancer), lung cancer including small-cell lung cancer, non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Tumors in which HER2 heterodimer formation is implicated (with or without HER2 overexpression) include, without limitation, prostate cancers, ovarian cancers, including advanced, refractory or recurrent ovarian cancer, coloreactal cancers, prostate cancers, lung cancers, especially non-small cell lung cancer, breast cancers, including metastatic breast cancers, colon, pancreatic, peritoneal, and fallopian tube cancers.

Patients who are candidates for the treatment methods of the present invention can be selected using assays and techniques known in the art.

Generally, if a diagnostic test is performed, a sample may be obtained from a patient in need of therapy. Where the subject has cancer, the sample is generally a tumor sample. The sample may, for example, be a fresh biopsy sample, a fixed sample, e.g. a formalin fixed, paraffin-embedded (FFPE) sample, or a frozen sample.

According to one embodiment of the invention herein, the patient selected for therapy has a tumor displaying EGFR and HER2 activation, jointly referred to as "HER activation." In one embodiment, the extent of HER activation in cancer cells significantly exceeds the level of activation of that receptor in non-cancerous cells of the same tissue type. Such excessive activation may result from overexpression of the HER receptor and/or greater than normal levels of a HER ligand available for activating the HER receptor in the cancer cells. Such excessive activation may cause and/or be caused by the malignant state of a cancer cell. In some embodiments, the cancer will be subjected to a diagnostic or prognostic assay to determine whether amplification and/or overexpression of a HER receptor is occurring which results in such excessive activation of the HER receptor. Alternatively, or additionally, the cancer may be subjected to a diagnostic or prognostic assay to determine whether amplification and/or overexpression a HER ligand is occurring in the cancer which attributes to excessive activation of the receptor. In a subset of such cancers, excessive activation of the receptor may result from an autocrine stimulatory pathway. Various assays for determining HER activation will be described in more detail below.

The preferred methods for determining HER activation are: detecting the presence of HER dimers or heterodimers, evaluating HER phosphorylation, and gene expression profiling.

Any method known in the art may be used to detect HER dimers, including HER2 dimers, such as EGFR-HER2, HER2-HER3, in tumors. Several preferred methods are described below. These methods detect noncovalent protein-protein interactions or otherwise indicate proximity between proteins of interest.

Immunoaffinity-based methods, such as immunoprecipitation or ELISA, may be used to detect HER dimers. Thus, to detect HER2 heterodimers, HER2 antibodies are used to immunoprecipitate complexes comprising HER2 from tumor cells, and the resulting immunoprecipitant is then probed for the presence of EGFR or HER3 by immunoblotting. In another embodiment, EGFR or HER3 antibodies may be used for the immunoprecipitation step and the immunoprecipitant then probed with HER2 antibodies. In a further embodiment, HER ligands specific to EGFR, HER3, EGFR-HER2 complexes or HER2-HER3 complexes may be used to precipitate complexes, which are then probed for the presence of HER2. For example, ligands may be conjugated to avidin and complexes purified on a biotin column. Similar method can be used to detect EGFR homodimers or heterodimers.

In other embodiments, such as ELISA or antibody "sandwich"-type assays, antibodies to HER2 are immobilized on a solid support, contacted with tumor cells or tumor cell lysate, washed, and then exposed to antibody against EGFR or HER3. Binding of the latter antibody, which may be detected directly or by a secondary antibody conjugated to a detectable label, indicates the presence of heterodimers. In certain embodiments, EGFR or HER3 antibody is immobilized, and HER2 antibody is used for the detection step. In other embodiments HER ligands may be used in place of, or in combination with HER antibodies. If the goal is to detect EGFR dimers, the primary antibody can be an EGFR antibody.

Chemical or UV cross-linking may also be used to covalently join dimers on the surface of living cells. Examples of chemical cross-linkers include dithiobis(succinimidyl)propionate (DSP) and 3,3'-dithiobis(sulphosuccinimidyl)propionate (DTSSP). In one embodiment, cell extracts from chemically cross-linked tumor cells are analyzed by SDS-PAGE and immunoblotted with antibodies to EGFR and/or HER3. A supershifted band of the appropriate molecular weight most likely represents EGFR-HER2 or HER2-HER3 dimers, as HER2 is the preferred dimerization partner for EGFR and HER3. This result may be confirmed by subsequent immunoblotting with HER2 antibodies.

Fluorescence resonance energy transfer (FRET) may also be used to detect EGFR-HER2 or HER2-HER3 heterodimers, or EGFR homodimers. FRET detects protein conformational changes and protein-protein interactions in vivo and in vitro based on the transfer of energy from a donor fluorophore to an acceptor fluorophore. Selvin, *Nat. Struct. Biol.,* 7:730-34 (2000). Energy transfer takes place only if the donor fluorophore is in sufficient proximity to the acceptor fluorophore. In a typical FRET experiment, two proteins or two sites on a single protein are labeled with different fluorescent probes. One of the probes, the donor probe, is excited to a higher energy state by incident light of a specified wavelength. The donor probe then transmits its energy to the second probe, the acceptor probe, resulting in a reduction in the donor's fluorescence intensity and an increase in the acceptor's fluorescence emission. To measure the extent of energy transfer, the donor's intensity in a sample labeled with donor and acceptor probes is compared with its intensity in a sample labeled with donor probe only. Optionally, acceptor intensity is compared in donor/acceptor and acceptor only samples. Suitable probes are known in the art and include, for example, membrane permeant dyes, such as fluorescein and rhodamine, organic dyes, such as the cyanine dyes, and lanthanide atoms. Methods and instrumentation for detecting and measuring energy transfer are also known in the art.

FRET-based techniques suitable for detecting and measuring protein-protein interactions in individual cells are also known in the art. For example, donor photobleaching fluorescence resonance energy transfer (pbFRET) microscopy and fluorescence lifetime imaging microscopy (FLIM) may be used to detect the dimerization of cell surface receptors. Gadella & Jovin, *J. Cell Biol.,* 129:1543-58 (1995). In one embodiment, pbFRET is used on cells either "in suspension" or "in situ" to detect and measure the formation of EGFR-HER2 or HER2-HER3 dimers, as described in Nagy et al., *Cytometry,* 32:120-131 (1998). These techniques measure the reduction in a donor's fluorescence lifetime due to energy transfer. In a particular embodiment, a flow cytometric Foerster-type FRET technique (FCET) may be used to investigate EGFR-HER2 and HER2-HER3 dimerization, as described in Nagy et al., supra, and Brockhoff et al., *Cytometry,* 44:338-48 (2001).

FRET is preferably used in conjunction with standard immunohistochemical labeling techniques. Kenworthy, *Methods,* 24:289-96 (2001). For example, antibodies conjugated to suitable fluorescent dyes can be used as probes for labeling two different proteins. If the proteins are within proximity of one another, the fluorescent dyes act as donors and acceptors for FRET. Energy transfer is detected by standard means. Energy transfer may be detected by flow cytometric means or by digital microscopy systems, such as confocal microscopy or wide-field fluorescence microscopy coupled to a charge-coupled device (CCD) camera.

In one suitable assay, HER2 antibodies and either EGFR or HER3 antibodies are directly labeled with two different fluorophores, for example as described in Nagy et al, supra. Tumor cells or tumor cell lysates are contacted with the differentially labeled antibodies, which act as donors and acceptors for FRET in the presence of EGFR-HER2 or HER2-HER3 dimers. Alternatively, unlabeled antibodies against HER2 and either EGFR or HER3 are used along with differentially labeled secondary antibodies that serve as donors and acceptors. See, for example, Brockhoff et al., supra. Energy transfer is detected and the presence of dimers is determined if the labels are found to be in close proximity.

In other assays, HER receptor ligands that are specific for HER2 and either EGFR or HER3 are fluorescently labeled and used for FRET studies.

In still other assays, the presence of dimers on the surface of tumor cells is demonstrated by co-localization of HER2 with either EGFR or HER3 using standard direct or indirect immunofluorescence techniques and confocal laser scanning microscopy. Alternatively, laser scanning imaging (LSI) is used to detect antibody binding and co-localization of HER2 with either EGFR or HER3 in a high-throughput format, such as a microwell plate, as described in Zuck et al, *Proc. Natl. Acad. Sci. USA,* 96:11122-27 (1999).

In further assays, the presence of EGFR-HER2 and/or HER2-HER3 dimers is determined by identifying enzymatic activity that is dependent upon the proximity of the dimer components. A HER2 antibody is conjugated with one enzyme and an EGFR or HER3 antibody is conjugated with a second enzyme. A first substrate for the first enzyme is added and the reaction produces a second substrate for the second enzyme. This leads to a reaction with another molecule to produce a detectable compound, such as a dye. The presence of another chemical breaks down the second substrate, so that reaction with the second enzyme is prevented unless the first and second enzymes, and thus the two antibodies, are in close proximity. In a particular embodiment tumor cells or cell lysates are contacted with a HER2 antibody that is conjugated with glucose oxidase and a HER3 or EGFR antibody that is conjugated with horse radish peroxidase. Glucose is added to the reaction, along with a dye precursor, such as DAB, and catalase. The presence of dimers is determined by the development of color upon staining for DAB.

Dimers may also be detected using methods based on the eTag™ assay system (Aclara Bio Sciences, Mountain View, Calif.), as described, for example, in U.S. Patent Application 2001/0049105, published Dec. 6, 2001, both of which are expressly incorporated by reference in their entirety. An eTag™, or "electrophoretic tag," comprises a detectable reporter moiety, such as a fluorescent group. It may also comprise a "mobility modifier," which consists essentially of a moiety having a unique electrophoretic mobility. These moieties allow for separation and detection of the eTag™ from a complex mixture under defined electrophoretic conditions, such as capillary electrophoresis (CE). The portion of the eTag™ containing the reporter moiety and, optionally, the mobility modifier is linked to a first target binding moiety by a cleavable linking group to produce a first binding compound. The first target binding moiety specifically recognizes a particular first target, such as a nucleic acid or protein. The first target binding moiety is not limited in any way, and may be for example, a polynucleotide or a polypeptide. Preferably, the first target binding moiety is an antibody or antibody fragment. Alternatively, the first target binding moiety may be a HER receptor ligand or binding-competent fragment thereof.

The linking group preferably comprises a cleavable moiety, such as an enzyme substrate, or any chemical bond that may be cleaved under defined conditions. When the first target binding moiety binds to its target, the cleaving agent is introduced and/or activated, and the linking group is cleaved, thus releasing the portion of the eTag™ containing the reporter moiety and mobility modifier. Thus, the presence of a "free" eTag™ indicates the binding of the target binding moiety to its target.

Preferably, a second binding compound comprises the cleaving agent and a second target binding moiety that specifically recognizes a second target. The second target binding moiety is also not limited in any way and may be, for example, an antibody or antibody fragment or a HER receptor ligand or binding competent ligand fragment. The cleaving agent is such that it will only cleave the linking group in the first binding compound if the first binding compound and the second binding compound are in close proximity.

In a particular embodiment, a first binding compound comprises an eTag™ in which an antibody to HER2 serves as the first target binding moiety. A second binding compound comprises an antibody to EGFR or HER3 joined to a cleaving agent capable of cleaving the linking group of the eTag™. Preferably the cleaving agent must be activated in order to be able to cleave the linking group. Tumor cells or tumor cell lysates are contacted with the eTag™, which binds to HER2, and with the modified EGFR or HER3 antibody, which binds to EGFR or HER3 on the cell surface. Unbound binding compound is preferable removed, and the cleaving agent is activated, if necessary. If EGFR-HER2 or HER2-HER3 dimers are present, the cleaving agent will cleave the linking group and release the eTag™ due to the proximity of the cleaving agent to the linking group. Free eTag™ may then be detected by any method known in the art, such as capillary electrophoresis.

In one embodiment, the cleaving agent is an activatable chemical species that acts on the linking group. For example, the cleaving agent may be activated by exposing the sample to light.

In another embodiment, the eTag™ is constructed using an antibody to EGFR or HER3 as the first target binding moiety, and the second binding compound is constructed from an antibody to HER2.

In yet another embodiment, the HER dimer is detected using an antibody or other reagent which specifically or preferentially binds to the dimer as compared to binding thereof to either HER receptor in the dimer.

Phosphorylation of HER receptor may be assessed by immunoprecipitation of one or more HER receptors, such as HER2 receptor, and analysis of phosphorylated tyrosine residue(s) in the immunoprecipitated receptor(s). For example, positivity is determined by the presence of a phospho-HER2 band on the gel, using an anti-phosphotyrosine antibody to detect phosphorylated tyrosine residue(s) in the immunoprecipitated HER receptor(s). Anti-phosphotyrosine antibodies are commercially available from PanVera (Madison, Wis.), a subsidiary of Invitrogen, Chemicon International Inc. (Temecula, Calif.), or Upstate Biotechnology (Lake Placid, N.Y.). Negativity is determined by the absence of the band. Various assay formats for detecting phosphorylated proteins are contemplated including Western blot analysis, immunohistochemistry, ELISA, etc.

In one embodiment, phosphorylation of HER2 (HER2) receptor is assessed by immunohistochemistry using a phospho-specific HER2 antibody (clone PN2A; Thor et al., J. Clin. Oncol, 18(18):3230-3239 (2000)).

Other methods for detecting phosphorylation of HER receptor(s) include, but are not limited to, KIRA ELISA (U.S. Pat. Nos. 5,766,863; 5,891,650; 5,914,237; 6,025,145; and 6,287,784), mass spectrometry (comparing size of phosphorylated and non-phosphorylated HER2), and e-tag proximity assay with both a HER (e.g. HER2) antibody and phospho-specific or phospho-tyrosine specific antibody (e.g., using the eTag™ assay kit available from Aclara BioSciences (Mountain View, Calif.). Details of the eTag assay are described hereinabove.

One may also use phospho-specific antibodies in cellular array to detect phosphorylation status in a cellular sample of signal transduction protein (US2003/0190689).

Gene expression profiling can serve as a surrogate for measuring HER phosphorylation directly. This is particularly useful where the sample is a fixed sample (e.g. paraffin-embedded, formalin fixed tumor sample) where HER phosphorylation may be difficult to reliably quantify. For example, expression of two or more HER receptors and one or more HER ligand in a sample is evaluated, wherein expression of the two or more HER receptors and one or more HER ligand indicates positive HER activation in the sample. Alternatively or additionally, expression of betacellulin and/or amphiregulin in the sample can be measured, wherein betacellulin and/or amphiregulin expression indicates positive HER activation in the sample.

According to a preferred embodiment of gene expression profiling for evaluating HER2 activation, a sample from the patient is tested for expression of two or more HER receptors (preferably selected from EGFR, HER2, and HER3) and one or more HER ligands (preferably selected from betacellulin, amphiregulin, epiregulin, and TGF-α, most preferably betacellulin or amphiregulin). For example, the two or more HER receptors may be EGFR and HER2, or HER2 and HER3, and the one or more HER ligands may be betacellulin or amphiregulin. Preferably, expression of HER2 and EGFR or HER3, as well as betacellulin or amphiregulin is determined. The sample may be tested for expression of betacellulin or amphiregulin alone, or in combination with testing for expression of two or more HER receptors. Positive expression of the identified gene(s) indicates the patient is a candidate for therapy with a HER dimerization inhibitor, such as pertuzumab. Moreover, positive expression of the gene(s) indicates the patient is more likely to respond favorably to therapy with the HER dimerization inhibitor than a patient who does not have such positive expression.

Various methods for determining expression of mRNA or protein include, but are not limited to, gene expression profiling, polymerase chain reaction (PCR) including quantitative real time PCR (qRT-PCR), microarray analysis, serial analysis of gene expression (SAGE), MassARRAY, Gene Expression Analysis by Massively Parallel Signature Sequencing (MPSS), proteomics, immunohistochemistry (IHC), etc. Preferably mRNA is quantified. Such mRNA analysis is preferably performed using the technique of polymerase chain reaction (PCR), or by microarray analysis. Where PCR is employed, a preferred form of PCR is quantitative real time PCR (qRT-PCR). In one embodiment, expression of one or more of the above noted genes is deemed positive expression if it is at the median or above, e.g. compared to other samples of the same tumor-type. The median expression level can be determined essentially contemporaneously with measuring gene expression, or may have been determined previously.

The steps of a representative protocol for profiling gene expression using fixed, paraffin-embedded tissues as the RNA source, including mRNA isolation, purification, primer extension and amplification are given in various published journal articles (for example: Godfrey et al. *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR. Finally, the data are analyzed to identify the best treatment option(s) available to the patient on the basis of the characteristic gene expression pattern identified in the tumor sample examined.

Although the tumors to be treated in accordance with the present invention do not have to overexpress a HER receptor (e.g. HER2 or EGFR), to determine HER expression or amplification in the cancer, various diagnostic/prognostic assays are available. In one embodiment, HER2 overexpression may be analyzed by IHC, e.g. using the HERCEPTEST® (Dako). Paraffin embedded tissue sections from a tumor biopsy may be subjected to the IHC assay and accorded a HER2 protein staining intensity criteria as follows:

Score 0– no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2.

Tumors overexpressing HER2 may be rated by immunohistochemical scores corresponding to the number of copies of HER2 molecules expressed per cell, and can been determined biochemically:

0=0-10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA*, 84:7159-7163 (1987)), occurs in approximately 30% of breast cancers, and in these patients, relapse-free survival and overall survival are diminished (Slamon et al., *Science*, 244:707-712 (1989); Slamon et al., *Science*, 235:177-182 (1987)).

Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of HER2 amplification in the tumor.

EGFR expression may be evaluated as for the methods for evaluating HER2 expression as noted above.

Where the cancer to be treated is hormone independent cancer, expression of the hormone (e.g. androgen) and/or its cognate receptor in the tumor may be assessed using any of the various assays available, e.g. as described above. Alternatively, or additionally, the patient may be diagnosed as having hormone independent cancer in that they no longer respond to anti-androgen therapy.

V. PHARMACEUTICAL COMPOSITIONS AND TREATMENT METHODS

Therapeutic formulations of the HER2 dimerization inhibitors and EGFR inhibitors used in accordance with the present invention depends on the chemical nature of the inhibitor.

HER2 dimerization inhibitor and EGFR inhibitor antibodies are prepared for storage by mixing the inhibitor or inhibitors with optional pharmaceutically acceptable carriers, excipients or stabilizers (*Remington's Pharmaceutical Sciences* 16th edition, Osol, A. Ed. (1980)), generally in the form of lyophilized formulations or aqueous solutions. Antibody crystals are also contemplated (see US Pat Appln 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG). Lyophilized antibody formulations are described in WO 97/04801, expressly incorporated herein by reference.

The preferred pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

Cetuximab (ERBITUX®) is commercially available as a sterile liquid formulation intended for intravenous infusion. A typical formulation contains (per vial) 100 mg cetuximab, 424 mg sodium chloride, 20 mg sodium dihydrogen phosphate dihydrate, 66 mg disodium phosphate dihydrate and water for injection ad 50 ml.

The formulations herein may also contain more than one active compound as necessary for the particular indication being treated, preferably those with complementary activities that do not adversely affect each other. Various drugs which can be combined with the HER dimerization inhibitor are described below. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

Small molecule drugs can be prepared and commercialized in formulations for oral use. For example, erlotinib (TARCEVA™) contains erlotinib as the hydrochloride salt. TARCEVA™ tablets are available in three dosage strengths containing erlotinib hydrochloride (27.3 mg, 109.3 mg and 163.9 mg) equivalent to 25 mg, 100 mg and 150 mg erlotinib and the following inactive ingredients: lactose monohydrate, hypromellose, hydroxypropyl cellulose, magnesium stearate, microcrystalline cellulose, sodium starch glycolate, sodium lauryl sulfate and titanium dioxide. The tablets also contain trace amounts of color additives, including FD&C Yellow #6 (25 mg only) for product identification.

In certain embodiments, an immunoconjugate comprising the HER2 and/or EGFR antibody conjugated with a cytotoxic agent is administered to the patient. Preferably, the immunoconjugate and/or HER2 or EGFR protein to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

The HER2 dimerization inhibitor and EGFR inhibitor antibodies antibodies or immunoconjugates are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The combined administration includes coadministration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In one embodiment, the treatment of the present invention involves the combined administration of a HER2 dimerization inhibitor, an EGFR inhibitor, and one or more chemotherapeutic agents or growth inhibitory agents, including coadministration of cocktails of different chemotherapeutic agents. Preferred chemotherapeutic agents include taxanes (such as paclitaxel and docetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The HER2 dimerization and EGFR inhibitors may be combined with an anti-hormonal agent or endocrine therapeutic; e.g., an anti-estrogen compound such as tamoxifen; an anti-progesterone such as onapristone (see, EP 616 812); or an anti-androgen such as flutamide, in dosages known for such molecules. Where the cancer to be treated is hormone independent cancer, the patient may previously have been subjected to anti-hormonal therapy and, after the cancer becomes hormone independent, the HER2 antibody (and optionally other agents as described herein) may be administered to the patient.

Sometimes, it may be beneficial to also coadminister a cardioprotectant (to prevent or reduce myocardial dysfunction associated with the therapy) or one or more cytokines to the patient. One may also coadminister an anti-angiogenic agent. In addition to the above therapeutic regimes, the patient may be subjected to surgical removal of cancer cells and/or radiation therapy.

Examples of additional drugs which can be combined with the HER2 dimerization inhibitors and EGFR inhibitors herein include chemotherapeutic agents such as carboplatin, a taxane (e.g. paclitaxel or docetaxel), gemcitabine, navelbine, cisplatin, oxaliplatin, or combinations of any of these such as carboplatin/docetaxel; another EGFR inhibitor; another HER2 dimerization inhibitor; another HER2 antibody (e.g. a growth inhibitory HER2 antibody such as trastuzumab, or an HER2 antibody which induces apoptosis such as 7C2 or 7F3, including humanized or affinity matured variants thereof); a farnesyl transferase inhibitor; an anti-angiogenic agent (e.g. an anti-VEGF antibody, such as AVASTIN®); a cytokine (e.g. IL-2, IL-12, G-CSF or GM-CSF); or combinations of the above.

Suitable dosages for any of the above coadministered agents are those presently used and may be lowered due to the combined action (synergy) of the agent and HER2 antibody.

For the prevention or treatment of disease, the appropriate dosage of a molecule, such as antibody or small molecule, will depend on the type of disease to be treated, as defined above, the severity and course of the disease, whether the antibody is administered for preventive or therapeutic purposes, previous therapy, the patient's clinical history and response to the antibody, and the discretion of the attending physician.

The antibody is suitably administered to the patient at one time or over a series of treatments. Depending on the type and severity of the disease, about 1 μg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. The preferred dosage of the antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the HER2 antibody).

An initial higher loading dose, followed by one or more lower doses may be administered. An exemplary dosing regimen comprises administering an initial loading dose of about 4 mg/kg, followed by a weekly maintenance dose of about 2 mg/kg of the HER2 antibody. However, other dosage regimens may be useful. The progress of this therapy is easily monitored by conventional techniques and assays.

In a particular embodiment, rhuMAb 2C4 (pertuzumab) is administered in a fixed dose of 420 mg (equivalent to doses of 6 mg/kg for a 70-kg subject) every 3 weeks. Treatment may start with a higher loading dose (e.g. 840 mg, equivalent to 12 mg/kg of body weight) in order to achieve steady state serum concentrations more rapidly. When combined with pertuzumab, erlotinib can, for example, be administered in a daily dose of 150 mg taken at least one hour before or two hours after the ingestion of food. However, in synergistic combinations the effective dose of one or both of pertuzumab and erlotinib can be reduced. Thus, for example, erlotinib can be administered in a daily dose of 100 mg or 50 mg, when combined with pertuzumab.

The recommended starting dose (loading dose) for cetuximab as monotherapy or in combination with pertuzumab is about 400 milligrams/m$^2$ infused intravenously (IV) over 2 hours followed by a weekly dose of 250 mg/m$^2$ infused IV over 1 hour, however, synergism between cetuximab and pertuzumab pay permit reduction of the effective dose or one or both of these antibodies.

In a particular embodiment, the combination of a HER2 dimerization inhibitor and EGFR inhibitor is used for the treatment of tumors which are refractory to traditional chemotherapy and/or radiation therapy or respond poorly to treatment with an EGFR inhibitor alone.

For example, a combination of pertuzumab and erlotinib can be used to treat advanced, refractory non-small cell lung cancer (NSCLC), especially nonsquamous NSCLC. NSCLC responds well to certain platinum-based chemotherapeutics. Chemotherapeutic agents with activity against NSCLC include cisplatin, which has been used both in the palliative treatment of metastatic (stage IV) disease and combined-modality therapy of stage III disease. However, resistance to platinum compounds is common, and acquired resistance emerges rapidly during therapy. Combination therapy with pertuzumab and erlotinib is particularly suitable to treat patients with advanced platinum-refractory NSCLC. In a preferred embodiment, a synergistic combination of pertuzumab and erlotinib is administered. If desired, administration of pertuzumab and erlotinib can be combined with treatment with other chemotherapeutics agents, such as taxanes, e.g. paclitaxel, docetaxel, vinorelbine, gemcitabine, or irinotecan, and/or radiation treatment.

In addition, pertuzumab and erlotinib can be successfully combined to treat pancreatic cancer, especially advanced pancreatic cancer, either following traditional chemotherapy, or as a first line treatment. Alternatively, combination therapy with pertuzumab and erlotinib can follow treatment with gemcitabine (GEMZAR®, Eli Lilly), which is often used to treat advanced pancreatic cancer. Again, synergistic combinations of pertuzumab and erlotinib are preferred.

In a further embodiment, pertuzumab and cetuximab are combined to treat colon, ovarian, or breast cancer, especially advanced refractory cancer.

In all embodiments, the treatment can be accompanied by the administration of other HER2 inhibitors and/or EGFR inhibitors, including, for example trastuzumab or other HER2 antibodies, and/or standard of care treatments, such as chemotherapy and/or radiation therapy. It is believed, however, that in most patients combination treatment with a HER2 dimerization inhibitor and an EGFR inhibitor, as taught by the present invention, is sufficient, and further therapeutic approaches do not provide significant additional benefits. Accordingly, one advantage of the combination therapy of the present invention is the ability to avoid the often serious side-effects associated with chemotherapy and radiation therapy, especially when synergism between the HER2 dimerization inhibitor and EGFR inhibitor permits the reduction of the doses that would be administered individually.

VI. DEPOSIT OF MATERIALS

The following hybridoma cell lines have been deposited with the American Type Culture Collection, 10801 University Boulevard, Manassas, Va. 20110-2209, USA (ATCC):

| Antibody Designation | ATCC No. | Deposit Date |
| --- | --- | --- |
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims. Indeed, various modifications of the invention in addition to those shown and described herein will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein.

Further details of the invention are illustrated by the following non-limiting Examples. The disclosures of all citations in the specification are expressly incorporated herein by reference.

Example 1

Effect of Pertuzumab and Erlotinib Combination on the Viability of MDA-175 Cells Materials and Methods
  Reagents
  The human breast carcinoma cell line, MDA-MB-175-VII (HTB-25) was obtained from the American Type Culture Collection (Rockville, Md., USA). HERCEPTIN and rhuMAb2C4 was from Genentech, Inc. (South San Francisco, Calif.). Erlotinib was obtained from OSI Pharmaceuticals (Uniondale, N.Y.). Z-VED-FMK was purchased from Enzyme Systems Products (Livermore, Calif.). The Apo-ONE Homogeneous Caspase-3/7 Assay reagent was from Promega Corporation (Madison, Wis.). RPMI 1640 and fetal bovine serum (FBS) were purchased from Invitrogen (Carlsbad, Calif.). Alamar Blue was purchased from Trek Diagnostic System, Inc. (Cleveland, Ohio). Crystal violet was prepared at Genentech, Inc., (South San Francisco, Calif.).

Cell Culture

MDA-MB-175-VII cells were cultured in RPMI 1640 supplemented with 10% fetal bovine serum (FBS).

Cell Proliferation Assay with Crystal Violet and alamarBlue

MDA-MB-175-VII cells were plated in 96-well plates ($2 \times 10^4$ cells/well) in 10% FBS RPMI 1640 and incubated overnight at 37° C. Next day the medium was removed and all treatments were done in RPMI 1640 supplemented with 1% FBS, L-glutamine, Hepes and Gentamicin. The cells were treated with rhuMAb2C4 (pertuzumab) alone, erlotinib alone or with combination and the plates were incubated for 3 days. Monolayers were stained with 0.5% crystal violet. Plates were air-dried, the dye was eluted with 0.1 M sodium citrate (pH 4.2) in ethanol (50:50) and the absorbance was measured at 540 nm. In some experiments alamarBlue a fluorometric/colorimetric dye was used as a growth indicator. Fluorescence was read using 96-well fluorometer with excitation at 530 nm and emission of 590 nm.

Figure 7:
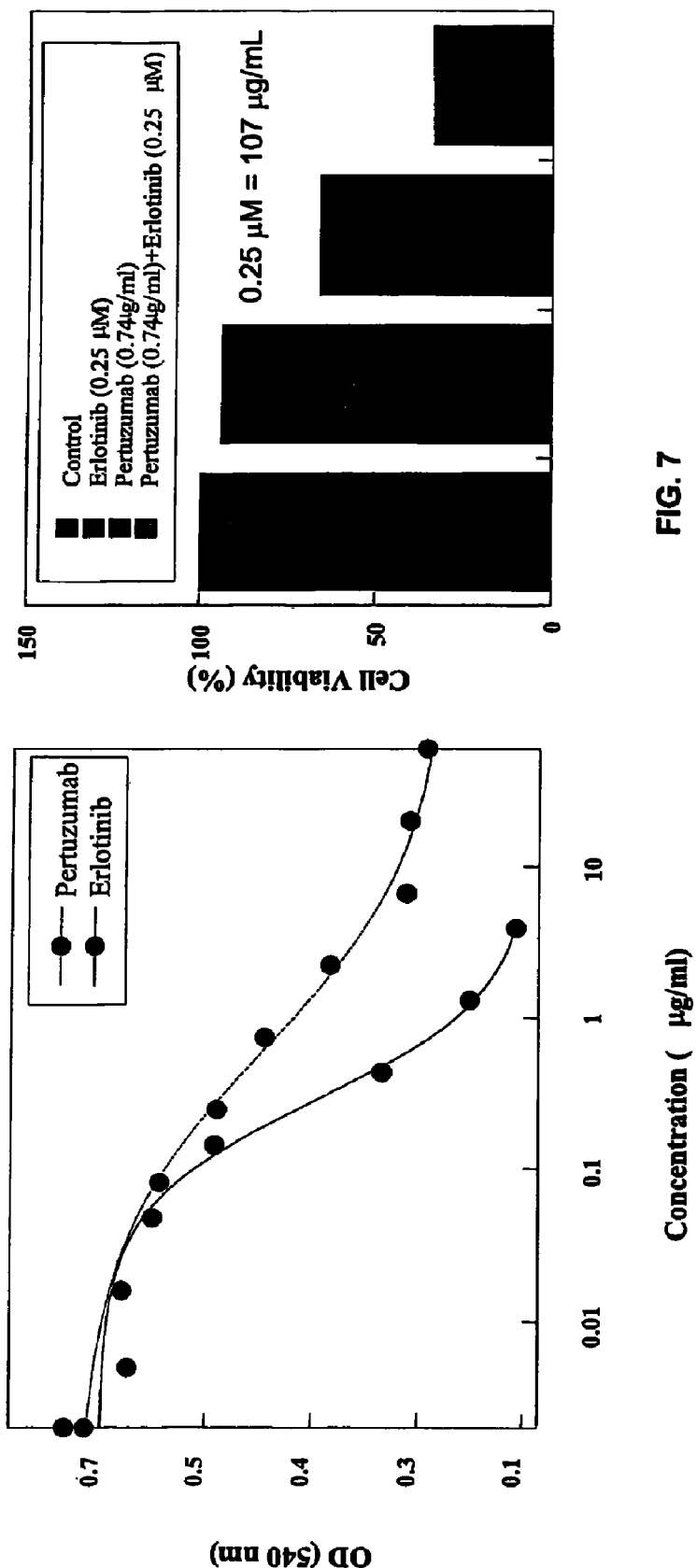
FIG. 7 shows the effect of the combination of pertuzumab and erlotinib on the viability of MDA-15 cells.

As shown in FIG. 7, the combination of pertuzumab and erlotinib was significantly more effective in reducing the viability of MDA-175 breast carcinoma cell line than either drug alone.

Example 2

Effect of Pertuzumab and Erlotinib Combination on Caspase 3/7 Activity in MDA-175 Cells Materials and Methods Caspase-3/7 Assay MDA-MB-175-VII cells were treated as described in the cell proliferation assay in Example 1. The Apo-ONE Homogeneous Caspase-3/7 reagent was used to measure of the activities of caspase-3/7 as recommended by the supplier.

Figure 8:
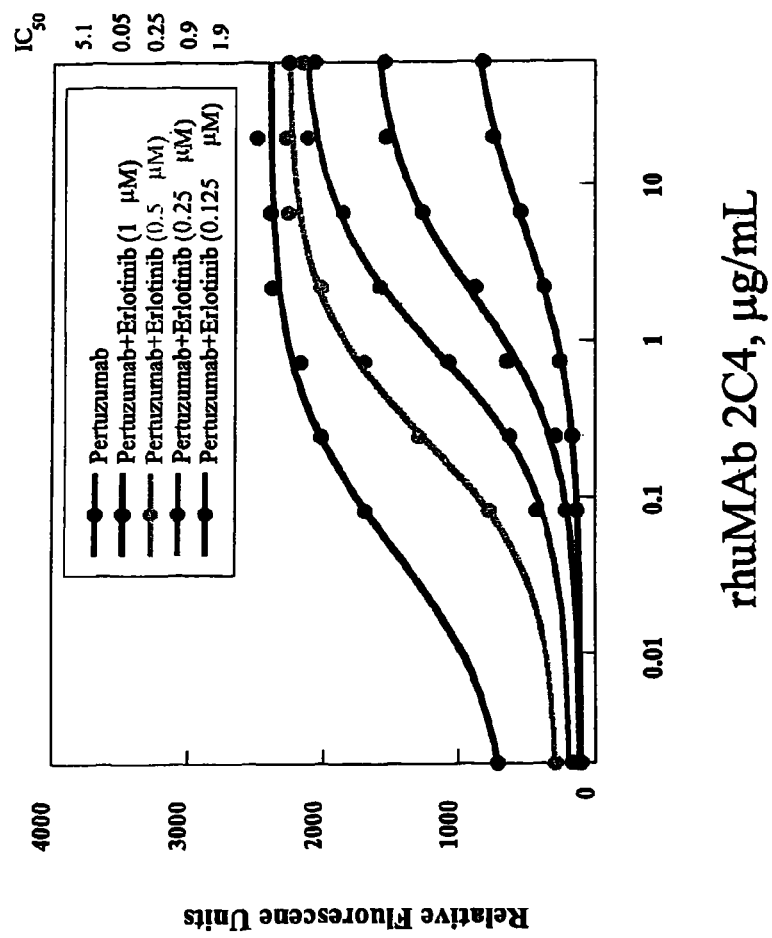
FIG. 8 shows the effect of the combination of pertuzumab and erlotinib on caspase 3/7 activity in MDA-175 cells.

Measuring caspase 3/7 enzymatic activity is a quantitative technique to measure apoptosis in tumor cells. The results depicted in FIG. 8 show that the combination of pertuzumab and erlotinib was significantly more effective in causing apoptosis than pertuzumab alone, and the result was dose dependent.

Figure 9:
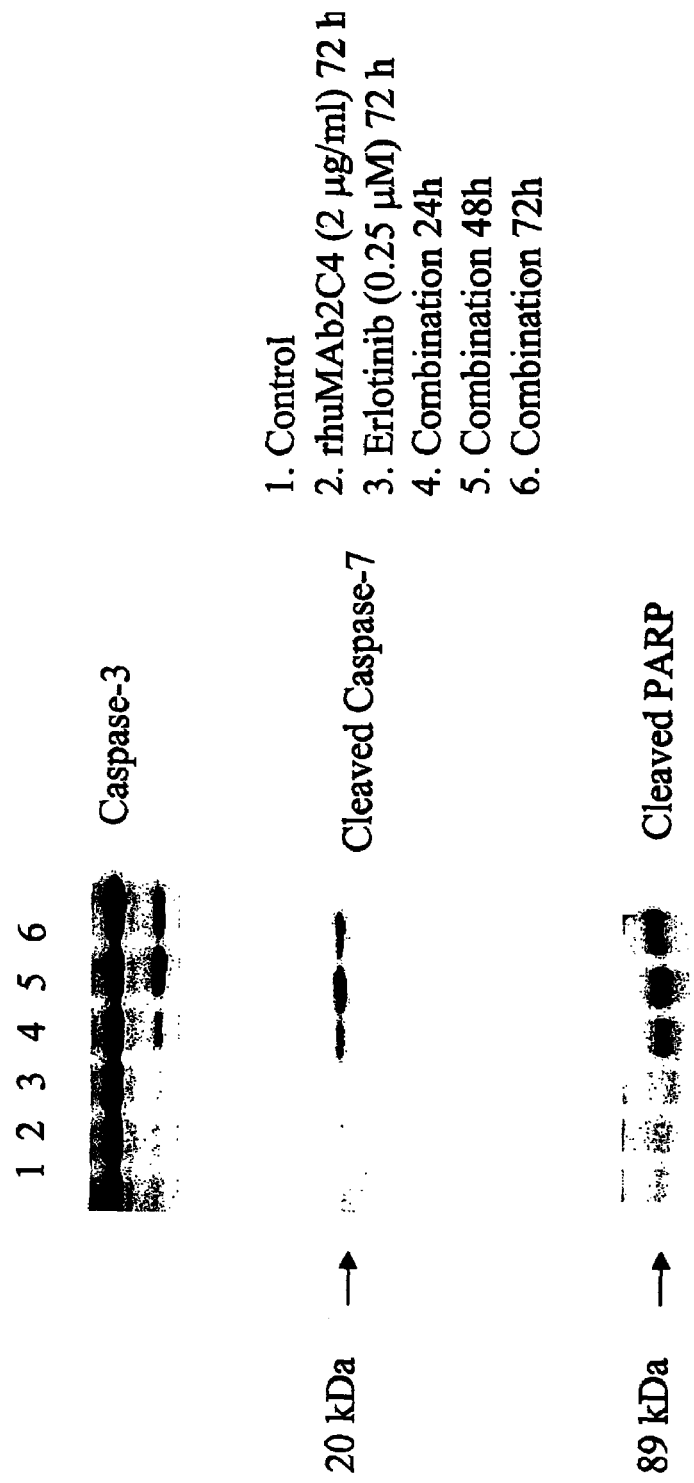
FIG. 9 shows the effect of the combination of pertuzumab and erlotinib on PARP and caspase 3, 7 cleavage.

In addition, FIG. 9 shows that the pertuzumab and erlotinib combination was significantly superior over either component alone in its ability to cleave caspase-3, caspase-7 and poly(ADP-ribose)polymerase (PARP).

Example 3

Effect of Pertuzumab and Erlotinib Combination on Apoptosis of MDA-175 Cells

Apoptosis Analysis

MDA-MB-175-VII cells were plated in RPMI 1640 medium containing 10% fetal bovine serum and allowed to attach. Next day the medium was removed and the cells were incubated with rhuMAb2C4 (10 or 2 µg/ml), Tarceva (3 or 0.25 µM) or with combination of both agents at lower concentrations in 1% FBS, L-glutamine, Hepes and Gentamicin supplemented medium. Treatment was continuous for 72, 48, and 24 hours. Supernatants and cells were collected and lysed in sample buffer (Invitrogen) containing BME. Lysates were run on 10% polyacrylamide gels and electro blotted onto nitrocellulose membrane. The following antibodies characterized caspase activity: caspase-3, -7, -9 and PARP (Cell Signaling Technologies, Beverly, Mass.).

Figure 10:
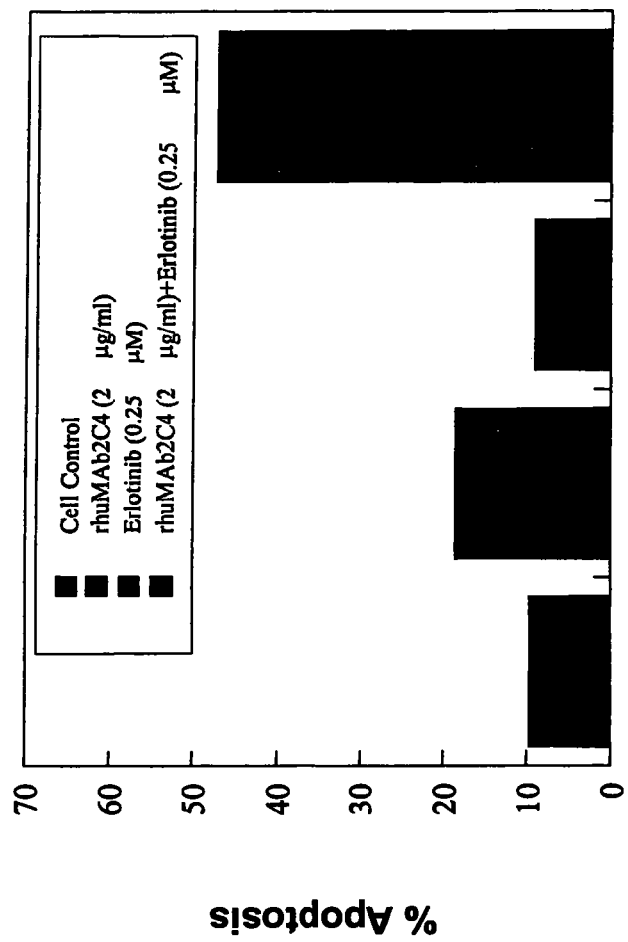
FIG. 10 shows the effect of the combination of pertuzumab and erlotinib on apoptosis of MD-175 cells.
Figure 11:
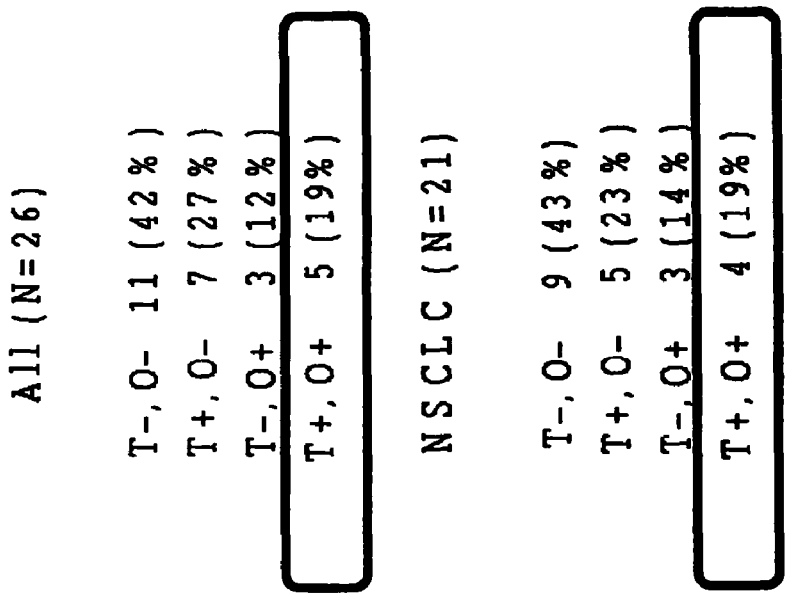
FIG. 11 lists various lung, breast and ovarian cell lines tested in xenograft models, testing their responsiveness to pertuzumab and erlotinib, used alone or in combination, and summarizes the results of the tests.

As shown in FIG. 10, the combination of pertuzumab and erlotinib was significantly more effective in causing apoptosis of MDA-175 cells than either component alone, and the effect was synergistic.

Example 4

In Vivo Evaluation of the Antitumor Activity of Pertuzumab and Erlotinib in Human Cancer Xenograft Models Pertuzumab and erlotinib were tested alone and in combination, in various in vivo human lung, breast and ovarian cancer xenograft models. The cell lines tested are listed in the table shown in FIG. 10.

The tumor models were established by implanting tumor tissues obtained from human patients into randomized NMRI nu/nu nude mice (Oncotest GmbH, Freiburg, Germany) and tumors were propagated until stable tumor growth behavior was observed. After removal of the tumor from the donor mice, the tumor was cut into fragments (2 mm diameter) and placed in RPMI 1640 culture medium until subcutaneous implantation in the mice. The tumor fragments (two per mouse) were transplanted by tweezers. The mice were monitored daily.

The pertuzumab solution (167 mg/ml) was stored at 4° C. in dark. The substance was diluted with a buffer containing 10 mM L-histidine, 240 mM sucrose, 0.02% polysorbate 20 pH 6 (HCl). The solutions were prepared fresh daily. Erlotinib was delivered as a ready-to-use formulation dissolved in 6% captisol.

Pertuzumab and the vehicle (10 mM L-histidine, 240 mM sucrose, 0.02% polysorbate 20 pH 6 (HCl)) were administered intraperitoneally (i.p., 100 mg/kg). Erlotinib was administered orally (25 mg/kg). The control mice received the vehicle by the same procedure and on the same schedule as the test compound.

As shown in FIG. 10, altogether 26 tumor xenografts were tested, of which 21 were established from non-small cell lung cancer (NSCLC). The antitumor effect was evaluated following maximum tumor inhibition versus the control group.

Tumor volumes were determined by two-dimensional measurement with a caliper at the day of randomization (day 0) and then 2-3 times weekly. The tumor volume was calculated using the following formula:

$$\text{Tumor Volume} = (a \times b^2) \times 0.5,$$

where a and b represent two perpendicular tumor diameters, a=length (longer diameter), b=width (shorter diameter). All mice of a treatment group were sacrificed when the tumors reached mean diameters of approximately 16 mm.

Relative tumor volumes (RTV) were calculated for each individual tumor, by dividing the tumor volume on day X ($V_x$) by the tumor volume on day 0 ($V_0$) multiplied by 100%. The tumor volume of a treatment group was expressed as the median RTV of all mice of the group. Median RTV volumes were used for drawing growth curves and treatment evaluation.

Optimal tumor growth inhibition at a particular day within the experimental period was calculated from the median RTV values of the test versus control groups multiplied by 100% (T/C 100%).

Relative tumor volume ($T_x/T_0$) was defined as the median relative tumor volume of the test group on day X divided by the medium relative tumor volume of the test group on day 0, multiplied by 100.

T/C % and $T_x/T_0$ were used for activity rating of the levels of efficacy, which were defined as follows:

| | | |
|---|---|---|
| − | inactive | T/C > 50% |
| + | moderate activity | T/C 26-50% |
| ++ | high activity | T/C 11-25% |
| +++ | very high activity | T/C < 10% |
| ++++ | complete remission | T/C 0% |

The results of monotherapy with pertuzumab (O) and erlotinib (T) are summarized in FIG. 10. 11 of the 26 tumors tested (42%) did not respond to treatment with either pertuzumab or erlotinib. 7 tumor (27%) was moderately responsive to treatment with erlotinib, but not pertuzumab. 3 tumor (12%) was responsive to both erlotinib and pertuzumab.

Limiting the assessment of data to NSCLC, 9 out of the 21 tumors tested (43%) showed no response to pertuzumab or erlotinib monotherapy. 5 NSCLC tumors (23%) responded to erlotinib but not to pertuzumab, 3 (14%) responded to pertuzumab but not erlotinib, and 3 (19%) responded to treatment with both erlotinib and pertuzumab.

The tumors which show moderate response to monotherapy both with pertuzumab and with erlotinib are expected to benefit from combination treatment. Thus, for example, the lung adenocarcinoma designated LXFA 629 showed moderate response to treatment with pertuzumab and erlotinib alone. This tumor, and other tumors with similar properties, are therefore good candidates for combination treatment with pertuzumab and erlotinib. In contrast, tumors which show high or very high responsiveness to either pertuzumab or erlotinib treatment are not expected to benefit from combination therapy to a great degree.

Example 5

HER Expression in Various Cancers

To determine the relationship of gene expression among members of the HER family, the pair wise scatter plots of their gene expression were analyzed in human cancer samples. The gene expression data were derived from a commercially available database called GeneExpress from GeneLogic, Inc. (Gaithersburg, Md.), in which several thousand human tissue samples have been assayed on Affymetrix GeneChip™ microarrys. In particular, the analysis was based on the assays performed on the Affymetrix HG-U133A and HG-U133B GneChips, and the gene expression signal values derived from Affymetrix MAS (Microarray Analysis Suite), version 5. For each probe set on the microarray, one can extract a gene expression profile, which consists of the relative expression levels over each of the human tissue samples. For the ErbB family, the following probe sets were used:

```
EGFR
  TCCTGTCTATCACAATCAGCCTCTG    (SEQ ID NO: 23)
  CAACCCCGAGTATCTCAACACTGTC    (SEQ ID NO: 24)
  GTGTCAACAGCACATTCGACAGCCC    (SEQ ID NO: 25)
  AAATTAGCCTGGACAACCCTGACTA    (SEQ ID NO: 26)
  CTGACTACCAGCAGGACTTCTTTCC    (SEQ ID NO: 27)
  ATGGCATCTTTAAGGGCTCCACAGC    (SEQ ID NO: 28)
  GCAGAATACCTAAGGGTCGCGCCAC    (SEQ ID NO: 29)
  AAAATCCAGACTCTTTCGATACCCA    (SEQ ID NO: 30)
  CATTAGCTCTTAGACCCACAGACTG    (SEQ ID NO: 31)
  GTTTTGCAACGTTTACACCGACTAG    (SEQ ID NO: 32)
  TCCACCTCGGGCACATTTTGGGAAG    (SEQ ID NO: 33)
HER2
  GCACCTTCAAAGGGACACCTACGGC    (SEQ ID NO: 34)
  AGTACCTGGGTCTGGACGTGCCAGT    (SEQ ID NO: 35)
  GCCATGCCAGGAACCTGTCCTAAGG    (SEQ ID NO: 36)
  CCTGCTTGAGTTCCCAGATGGCTGG    (SEQ ID NO: 37)
  GAGTCTTTGTGGATTCTGAGGCCCT    (SEQ ID NO: 38)
  GGCCCTGCCCAATGAGACTCTAGGG    (SEQ ID NO: 39)
  GACTCTAGGGTCCAGTGGATGCCAC    (SEQ ID NO: 40)
  CTTTCCTTCCAGATCCTGGGTACTG    (SEQ ID NO: 41)
  AAGCGACCCATTCAGAGACTGTCCC    (SEQ ID NO: 42)
  AGACTGTCCCTGAAACCTAGTACTG    (SEQ ID NO: 43)
  GGTGTCAGTATCCAGGCTTTGTACA    (SEQ ID NO: 44)
HER3
  CTTATGGTATGTAGCCAGCTGTGCA    (SEQ ID NO: 45)
  CTTCTTCACAGGCACTCCTGGAGAT    (SEQ ID NO: 46)
  GAAGGATTACTCTCCATATCCCTTC    (SEQ ID NO: 47)
  CTCTCAGGCTCTTGACTACTTGGAA    (SEQ ID NO: 48)
  GGAACTAGGCTCTTATGTGTGCCTT    (SEQ ID NO: 49)
  TTTGTTTCCCATCAGACTGTCAAGA    (SEQ ID NO: 50)
  TGGTTTATGACTCTTAACCCCCTAG    (SEQ ID NO: 51)
  TTAACCCCCTAGAAAGACAGAAGCT    (SEQ ID NO: 52)
  TCAGCACTTAACTATGAGCCAGGCA    (SEQ ID NO: 53)
  CATCATACTAAACTTCACCTACATT    (SEQ ID NO: 54)
  TAAACTTCACCTACATTATCTCACT    (SEQ ID NO: 55)
HER4
  GAGACAGTTCTCTGTGGTTCAGGAA    (SEQ ID NO: 56)
  GATACTTTCAGGGGTGGCCCAATGA    (SEQ ID NO: 57)
  GAAACACACTGGATTGGGTATGTCT    (SEQ ID NO: 58)
  GGGTATGTCTACCTGGCAGATACTC    (SEQ ID NO: 59)
  GGAACCTTGCAACGGTATCCAGGGA    (SEQ ID NO: 60)
  GGGACTATGATGAGAGGCCAGCACA    (SEQ ID NO: 61)
  GAGGCCAGCACATTATCTTCATATG    (SEQ ID NO: 62)
  TCTTCATATGTCACCTTTGCTACGC    (SEQ ID NO: 63)
  AATTTGTTCAGTTCGTATACTTCGT    (SEQ ID NO: 64)
  GTAGAAGGTAACTCTTTGCACATAA    (SEQ ID NO: 65)
  GCTTAGGGATAGGTCCTTGGGTCAA    (SEQ ID NO: 66)
```

A separate analysis was performed for each organ of interest, including breast, colon, lung, ovary, pancreas, and hematological malignancies. For each of these organs of interest, cancer samples deriving from that organ were identified in the GeneExpress database, and the gene expression data for those sample and the probe sets for the HER family were extracted.

The data for any pair of probe sets can be represented as a single scatterpoint, in which each data point represents a tissue sample. These scatterpoints reveal information about the co-expression of two genes, such as whether the expression is correlated. For the four HER family members, all pair wise scatterplots can be plotted on a single page as a matrix of scatterplots. This matrix reveals information about the relationship of gene expression across the entire family.

Because gene expression data can contain artifacts, outliers, and other types of noise, a preliminary matrix of the scatterplots was generated, and outlier samples that obscured the underlying biological relationship were eliminated. The matrix of scatterplots was then generated again using the remaining samples.

Figure 12A:
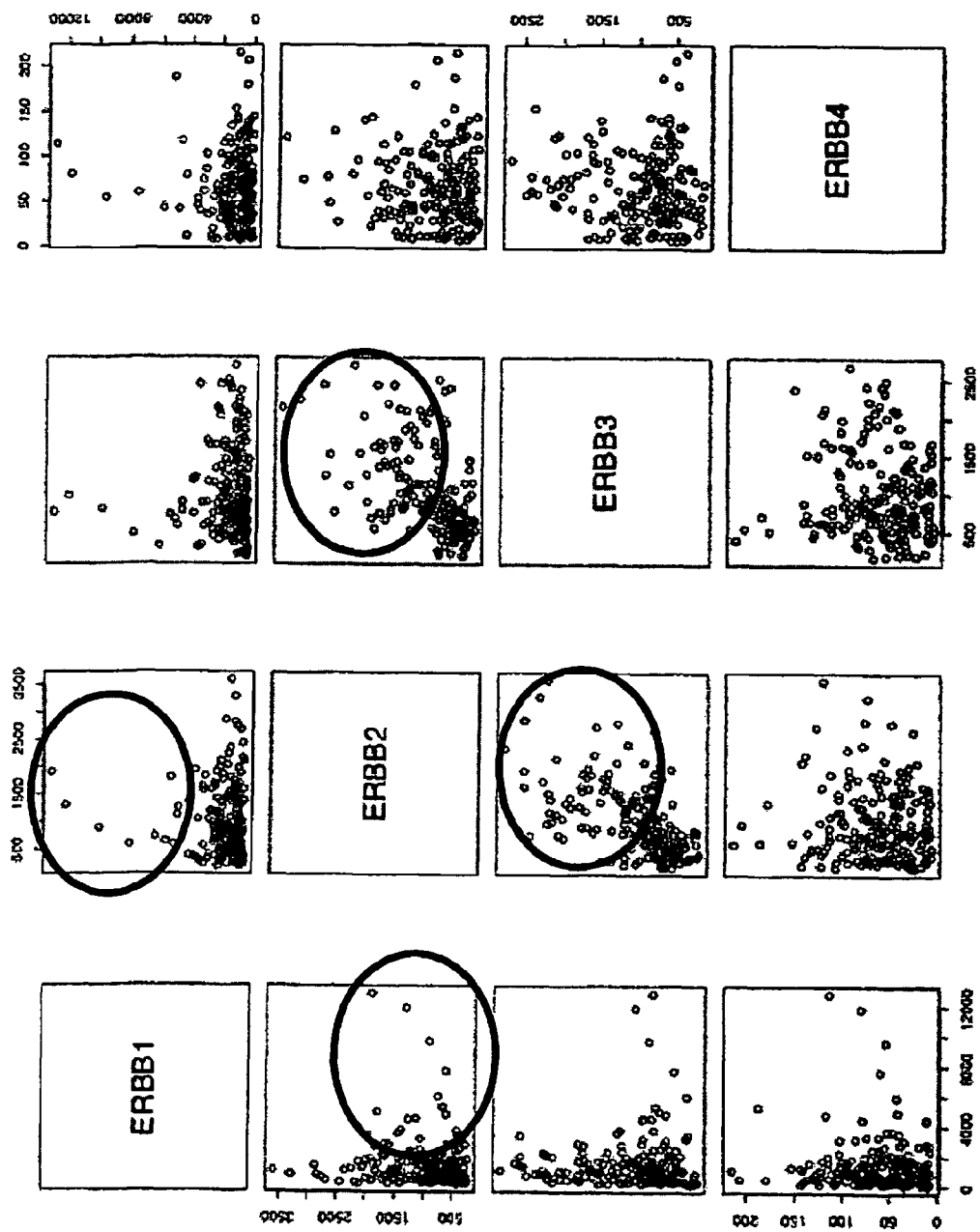
FIGS. 12A, B and C show the expression of ErbB1, ErbB2, ErbB3 and ErbB4 in lung, pancreatic, and colon cancer, respectively.
Figure 12B:
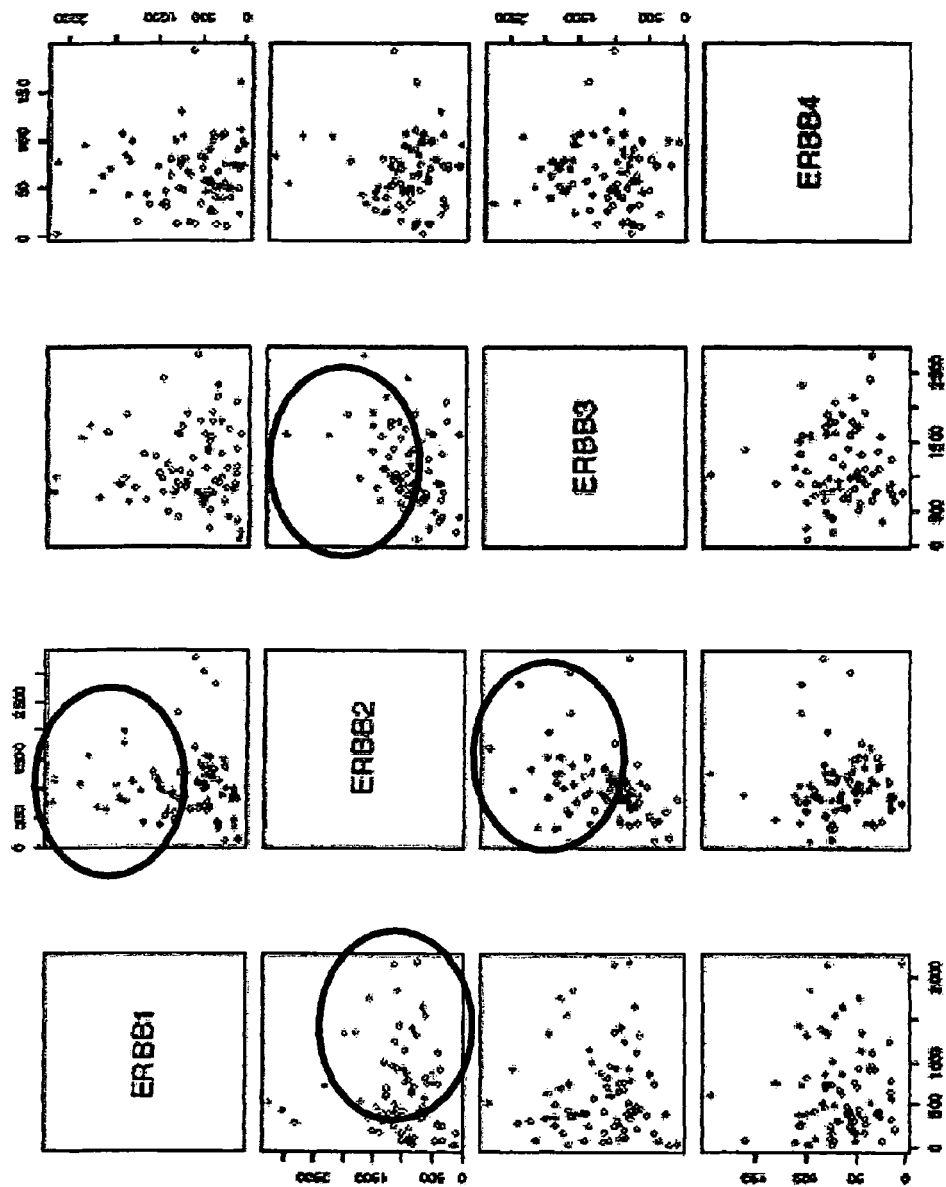
Figure 12C:
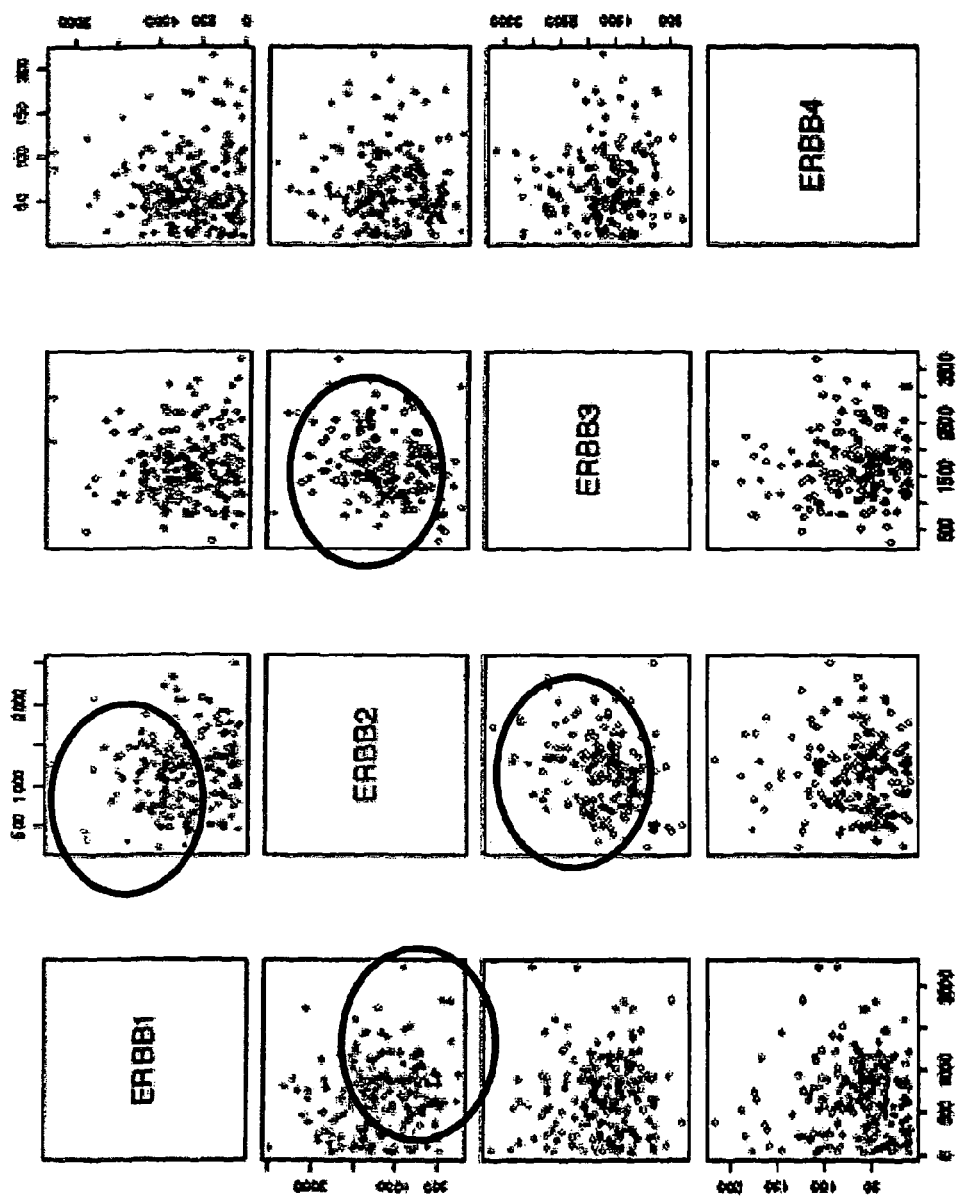

The results for lung, pancreatic and colon cancer are shown in FIGS. 12A, B and C, respectively.

The lung cancer scatterplots indicate that the addition of tarceva to erlotinib might be beneficial primarily by blocking the formation of HER2/HER3 heterodimers in addition to the EGFR/HER2 heterodimers blocked by erlotinib.

The pancreatic cancer scatterplots indicate that the combination of tarceva and erlotinib may be beneficial by blocking the formation of both EGFR/HER2 and HER2/HER3 heterodimers.

The colon cancer scatterplots predict that the addition of tarceva may potentiate the activity of erlotinib by blocking the formation of HER2/HER3 heterodimers.

Example 6

Therapy of Non-Small Cell Lung Cancer (NSCLC)

Subjects with NSCLC are treated with a combination of pertuzumab and erlotinib in this example. The subjects have HER2 expressing or HER2/3 expressing cancer. Therapy herein is provided as second or third line therapy. Second line therapy is treatment given when initial treatment (first line therapy) does not work, or stops working. Third line therapy is treatment given when both initial treatment (first line therapy) and subsequent treatment (second line treatment) do not work or stop working.

Pertuzumab is administered intravenously every three weeks at a dose of 0.5-15.0 mg/kg. Erlotinib is administered at a 50-150 mg oral dose once daily.

Activity of erlotinib in NSCLC subjects is improved by inhibiting EGFR-HER2 and HER2-HER3 heterodimers with pertuzumab. The outcome of treatment is monitored by assessing the time to death and/or time to disease (tumor) progression, and distribution of the time to death and/or time to disease progression in a patient population is estimated by generating Kaplan-Meier survival curves. Combination treatment with pertuzumab and erlotinib results in a significant increase at least one of time to death and time to progression.

Example 7

Therapy of Pancreatic Cancer

Human subjects with pancreatic cancer are treated with a combination of pertuzumab and erlotinib in this example. Gemcitabine is optionally added as a third anti-cancer agent.

Pertuzumab is administered intravenously every three weeks at a dose of 0.5-15.0 mg/kg. Erlotinib is administered at a 50-150 mg oral dose once daily.

Gemcitabine is administered as an intravenous injection at a standard dose of 1000 mg/m2 on days 1, 8, 15, etc. of treatment.

The outcome of treatment is monitored by assessing the time to death and/or time to disease (tumor) progression, and distribution of the time to death and/or time to disease (tumor) progression in a patient population is estimated by generating Kaplan-Meier survival curves. Modest activity of erlotinib in pancreatic cancer is improved by inhibiting EGFR-HER2 and HER2-HER3 heterdodimers with pertuzumab, especially as measured by assessing the time to death or time to diseases progression.

Example 8

Therapy of Colon Cancer

Human subjects are treated with a combination of pertuzumab and cetuximab in this example. The population of treated subjects are third line or unsuitable for chemotherapy, where third line therapy is treatment given when both initial treatment (first line therapy) and subsequent treatment (second line treatment) do not work or stop working.

Pertuzumab is administered intravenously every three weeks at a dose of 0.5-15.0 mg/kg.

Cetuximab is administered as an infusion, at a dose of and 400 mg/m$^2$, for example, starting with a loading dose of 400 mg/m$^2$, followed by 250 mg/m$^2$ of cetuximab weekly.

Further inhibiting EGFR-HER2 or HER2-HER3 heterodimers with pertuzumab and cetuximab will be more effective than cetuximab alone. The outcome of treatment is monitored by assessing the time to death and/or time to disease (tumor) progression, and distribution of the time to death and/or time to disease (tumor) progression in a patient population is estimated by generating Kaplan-Meier survival curves. Combination treatment with pertuzumab and cetuximab results in a significant increase at least one of time to death and time to progression.

Example 9

Preparation of Compound of Formula 4

Reaction:

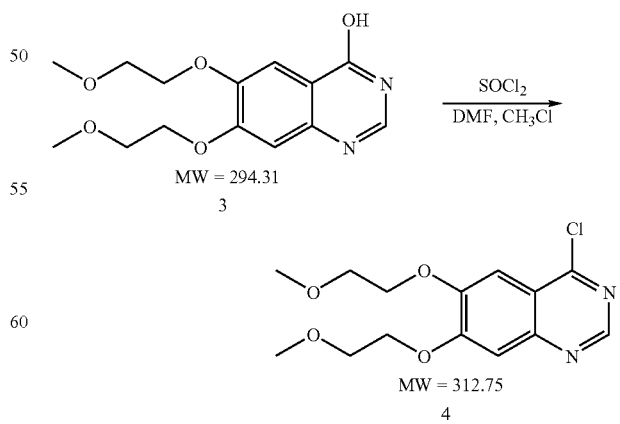

The following materials were used in the synthesis of the compound of formula 4:

| Materials | Quantity | Units | Equivalents/Volumes |
|---|---|---|---|
| Compound of formula 3 | 88.0 | kg | 1 equivalent |
| Thionyl chloride | 89.0 | kg | 2.5 equivalents |
| Dimethylformamide | 11 | kg | 0.5 equivalent |
| methylene chloride | 880.0 | L | 10 L/kg |
| 50% NaOH soln | as required | L | 1 equivalent |
| Heptane | 880.0 | L | 10 L/kg |

The following procedure is exemplary of the procedure to follow in the synthesis of the formula 4 compound:

88.0 kg of the compound of formula 3, 880.0 L methylene chloride, and 11.0 kg of dimethylformamide were charged to a clean, dry, glass-lined vessel under nitrogen atmosphere. 89 Kg of thionyl chloride were added to the mix while it is maintained at a temperature of a less than 30° C. during the charge. The contents of the reaction vessel were then heated for a minimum of five hours at reflux temperature before sampling for reaction completion and the pH is adjusted to be maintained between 7.0 to 8.0, by using 50 % NaOH, as required and the temperature of the reaction mixture is maintained at less than 25° C. The biphasic mixture is stirred for fifteen to twenty minutes and allowed to settle for a minimum of thirty minutes. The layers were separated and the organic layer was concentrated to ⅓ of its volume by removing methylene chloride. 880 L heptane was added with continued distillation of the remaining methylene chloride until the distillate reaches a temperature between 65 and 68° C. The mixture was then cooled to between 10 to 15° C. over hours and granulated for a minimum of 1 hour with the solids being isolated by filtration and washed with 220 L heptane. The solids (formula 4 compound) were dried in a vacuum drier at 45 to 50° C.

Example 10

Alternative Preparation of Compound of Formula 4

In the reaction shown in Example 4, sodium bicarbonate may successfully be used instead of sodium hydroxide as shown in this Example.

| Materials | Quantity | Units | Equivalents/Volumes |
|---|---|---|---|
| Compd 3 | 30.0 | kg | 1 equivalent |
| Thionyl chloride | 36.4 | kg | 3 equivalents |
| Dimethyl formamide | 3.75 | kg | 0.5 equivalent |
| methylene chloride | 300 | L | 10 L/kg |
| 50% NaOH soln | as required | L | |
| Heptane | 375 | L | 12.5 L/kg |
| Heptane (wash) | 90 | L | 3 L/kg |
| Sodium Bicarbonate | 64.2 | Kg | 7.5 equivalents |

30.0 kg of the compound of formula 3, 300.0 L methylene chloride, and 3.75 kg of dimethylformamide were charged to a clean, dry, glass-lined vessel under a nitrogen atmosphere. 36.4 kg of thionyl chloride was added to the mix while it was maintained at a temperature of less than 30° C. during the charge. The contents of the reaction vessel were then heated at reflux temperature for 13 h before sampling for reaction completion. The reaction mixture was cooled to 20-25° C. and added slowly to a stirred solution of sodium bicarbonate 64.2 kg and water 274 L cooled to 4° C. so that the temperature was maintained at less than 10° C. The final pH of the mixture was adjusted to within the range 7.0 to 8.0 by using 50% sodium hydroxide solution as required. The biphasic mixture was stirred for fifteen to twenty minutes and allowed to settle for a minimum of thirty minutes at 10-20° C. The layers were separated and the organic layer was concentrated to ⅓ of its volume by removing methylene chloride. 375 L of heptane was added with continued distillation of the remaining methylene chloride until the distillate reached a temperature between 65 and 68° C. The mixture was then cooled to 0 to 5° C. over 4 hours and granulated for a minimum of 1 hour with the solids being isolated by filtration and washed with 90 L heptane. The solids (formula 4 compound) were dried in a vacuum drier to 50° C.

Example 11

Preparation of Compounds 6 and 2 (Step 2)

Reaction:

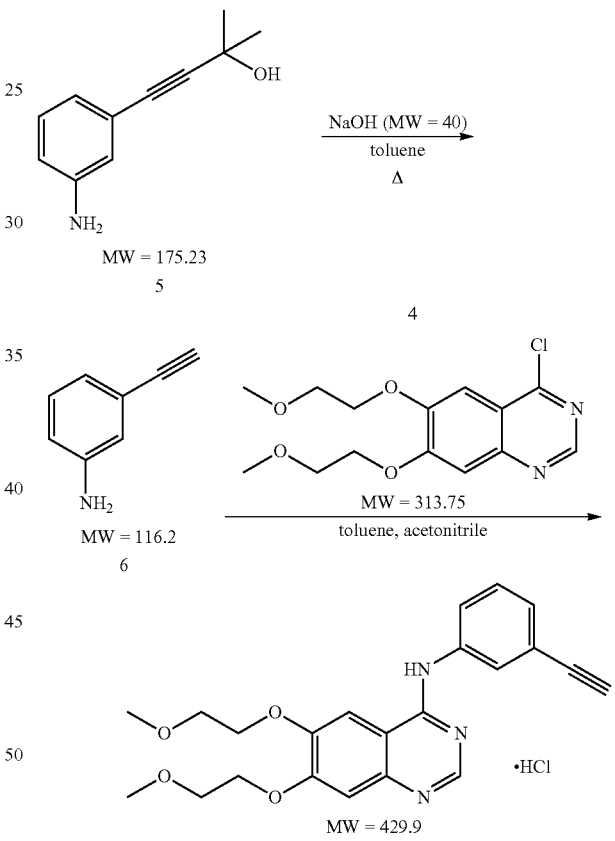

The following materials were used in the synthesis of the compound of formula 6, as intermediate, and the compound of formula 2:

| Materials | Quantity | Units | Equivalents/Volumes |
|---|---|---|---|
| Comp 5 | 61.1 | kg | 1.2 equivalents |
| Toluene | 489 | L | 8 L/kg (WRT to comp 5) |
| NaOH pellets | 4.5 | kg | 0.16 equivalents |
| Filteraid | 0.5 | kg | 0.017 kg/kg (WRT to comp 5) |

-continued

| Materials | Quantity | Units | Equivalents/Volumes |
|---|---|---|---|
| Comp 4 | 90.8 | kg | 1.0 equivalent |
| Acetonitrile | 732 | L | 12 L/kg (WRT to compd 5) |

The following procedure is exemplary of the procedure to follow in the synthesis of the formula 2 compound and intermediate compound of formula 6:

61.1 kg of formula 5 compound, 4.5 kg sodium hydroxide pellets and 489 L toluene were charged to a clean, dry, reaction vessel under nitrogen atmosphere and the reaction temperature is adjusted to between 105 to 108° C. Acetone was removed over four hours by atmospheric distillation while toluene is added to maintain a minimum volume of 6 L of solvent per kg of formula 5 compound. The reaction mixture was then heated at reflux temperature, returning distillates to pot, until the reaction was complete. The mixture was then cooled to between 20 to 25° C., at which time a slurry of 40.0 L toluene and 0.5 kg filteraid was charged to the reaction mixture and the mixture was agitated for ten to fifteen minutes. The resultant material was filtered to remove filteraid, and the cake is washed with 30 L toluene (compound of formula 6).

The filtrate (compound of formula 6) was placed in a clean, dry reaction vessel under nitrogen atmosphere, and 90.8 kg of the compound of formula 4 was charged into the reaction vessel together with 732 L acetonitrile. The reaction vessel was heated to reflux temperature and well agitated. Agitator speed was lowered when heavy solids appear. When the reaction was complete, the contents of reaction vessel were cooled to between to 25° C. over three to four hours and the contents were agitated for at least one hour at a temperature between 20 and 25° C. The solids (compound of formula 2, polymorph A form, or mixture of polymorph A and B) were then isolated by filtration and the filter cake was washed with two portions of 50 L acetonitrile and dried under vacuum at a temperature between 40 and 45° C.

It has been discovered that the production of the A polymorph is favored by the reduction of the amount of acetonitrile relative to toluene, and particularly favored if isopropanol is used in place of acetonitrile. However, the use of isopropanol or other alcohols as cosolvents is disfavored because of the propensity to form an ether linkage between the alcoholic oxygen and the 4-carbon of the quinazoline, instead of the desired ethynyl phenyl amino moiety.

It has been further discovered that adjusting the pH of the reaction to between pH 1 and pH 7, particularly between pH 2 and pH 5, for example, between pH 2.5 and pH 4, such as pH 3, will improve the rate of the reaction.

Example 12

Recrystallization of Compound of Formula 2 (which May be in Polymorph A Form or a Mixture of Polymorphs A and B) to Polymorph B (Step 3)

Reaction:

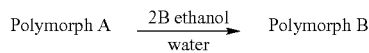

The following materials were used in the conversion of polymorph A (or mixtures of polymorphs A and B) to polymorph B of the compound of formula 2:

| Materials | Quantity | Units | Equivalents/Volumes |
|---|---|---|---|
| Polymorph A (comp 2) | 117.6 | kg | 1 equivalent |
| 2B-ethanol | 1881.6 | L | 16 L/kg |
| Water | 470.4 | L | 4 L/kg |

The following procedure is exemplary of procedures used to convert polymorph A (or mixtures of polymorphs A and B) into the more thermodynamically stable polymorph B of the compound of formula 2:

117.6 kg of the polymorph A (or mixtures of polymorphs A and B) were charged to a clean, dry, reaction vessel together 1881.6 L 2B-ethanol and 470.4 L water under a nitrogen atmosphere. The temperature was adjusted to reflux (~80° C.) and the mixture was agitated until the solids dissolve. The solution was cooled to between 65 and 70° C. and clarified by filtration. With low speed agitation, the solution was further cooled to between 50 and 60° C. over a minimum time of 2 hours and the precipitate was granulated for 2 hours at this temperature. The mixture was further cooled to between 0 and 5° C. over a minimum time of 4 hours and granulated for a minimum of 2 hours at this temperature. The solids (polymorph B) were isolated by filtration and washed with at least 100 L 2B-ethanol. The solids were determined to be crystalline polymorph B form of [6,7-bis(2-methoxyethoxy) quinazolin-4-yl]-(3-ethynyiphenyl)-amine hydrochloride substantially free of the polymorph A form. The solids obtained by this method are substantially homogeneous polymorph B form crystals relative to the polymorph A form. The method allows for production of polymorph B in an amount at least 70% by weight, at least 80% by weight, at least 90% by weight, at least 95% by weight, and at least 98% by weight relative to the weight of the polymorph A. It is to be understood that the methods described herein are only exemplary and are not intended to exclude variations in the above parameters which allow the production of polymorph B in varying granulations and yields, according to the desired storage, handling and manufacturing applications of the compound. The solids were vacuum dried at a temperature below 50° C. and the resultant product was milled to provide the polymorph B in usable form.

Polymorph B exhibits an X-ray powder diffraction pattern having characteristic peaks expressed in degrees 2-theta at approximately 6.26, 12.48, 13.39, 16.96, 20.20, 21.10, 22.98, 24.46, 25.14 and 26.91.

All references cited throughout the disclosure, and references cited therein, are hereby expressly incorporated by reference.

While the present invention is described with reference to certain embodiments, the invention is not so limited. One skilled in the art will appreciate that various modifications are possible without substantially altering the invention. All such modifications, which can be made without undue experimentation, are intended to be within the scope of the invention.

What is claimed is:

1. A method for the treatment of lung tumor comprising administering to a human subject with a lung tumor expressing EGFR and HER2, an effective amount of a HER2 antibody which is a HER2-dimerization inhibitor and an EGFR inhibitor, wherein the subject's tumor does not show a complete response to treatment with said HER2 antibody or said EGFR inhibitor when administered as a single agent, and is refractory to chemotherapy and/or radiation therapy.

2. The method of claim 1 wherein said tumor shows a partial response to treatment with said EGFR inhibitor administered as a single agent.

3. The method of claim 1 wherein said tumor shows a partial response to treatment with said HER2 antibody administered as a single agent.

4. The method of claim 1 wherein said tumor additionally expresses HER3.

5. The method of claim 1 wherein said tumor displays HER2 receptor overexpression or amplification.

6. The method of claim 1 wherein said tumor does not display HER2 receptor overexpression or amplification.

7. The method of claim 1 wherein said treatment increases the time to tumor progression and/or the time to death relative to treatment with said HER2 antibody or said EGFR inhibitor when administered as a single agent.

8. The method of claim 1 wherein said lung cancer is selected from the group consisting of small-cell lung cancer (SCLC), non-small cell lung cancer (NSCLC), adenocarcinoma of the lung, and squamous carcinoma of the lung.

9. The method of claim 8 wherein said lung cancer is non-small cell lung cancer (NSCLC).

10. The method of claim 9 wherein said treatment is provided as a second or third line therapy.

11. The method of claim 1 wherein said HER2 antibody binds to domain II of HER2 extracellular domain.

12. The method of claim 1 wherein said HER2 antibody binds to a junction between domains I, II and III of HER2 extracellular domain.

13. The method of claim 1 wherein said HER2 antibody is a humanized 2C4 antibody.

14. The method of claim 13 wherein said HER2 antibody comprises the variable light and variable heavy amino acid sequences in SEQ ID Nos. 11 and 12, respectively.

15. The method of claim 14 wherein said HER2 antibody is rhuMAb 2C4 (pertuzumab).

16. The method of claim 1 wherein said EGFR inhibitor is a non-peptide small molecule.

17. The method of claim 16 wherein said EGFR inhibitor has formula I:

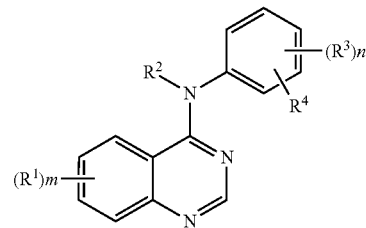

wherein:

X is halo or hydroxy;

m is 1, 2, or 3;

each $R^1$ is independently selected from the group consisting of hydrogen, halo, hydroxy, hydroxyamino, carboxy, nitro, guanidino, ureido, cyano, trifluoromethyl, and —($C_1$-$C_4$ alkylene)-W-(phenyl) wherein W is a single bond, O, S or NH;

or each $R^1$ is independently selected from $R^9$ and $C_1$-$C_4$ alkyl substituted by cyano, wherein $R^9$ is selected from the group consisting of $R^5$, —$OR^6$, —$NR^6R^6$, —C(O)$R^7$, —$NHOR^5$, —OC(O)$R^6$, cyano, A and —$YR^5$; $R^5$ is $C_1$-$C_4$ alkyl; $R^6$ is independently hydrogen or $R^5$; $R^7$ is $R^5$, —$OR^6$ or —$NR^6R^6$; A is selected from piperidino, morpholino, pyrrolidino, 4-$R^6$-piperazin-1-yl, imidazol-1-yl, 4-pyridon-1-yl, —($C_1$-$C_4$ alkylene)(CO2H), phenoxy, phenyl, phenylsulfanyl, $C_2$-$C_4$ alkenyl, and —($C_1$-$C_4$ alkylene)C(O)$NR^6R^6$; and Y is S, SO, or $SO_2$; wherein the alkyl moieties in $R^5$, —$OR^6$ and —$NR^6R^6$ are optionally substituted by one to three halo substituents and the alkyl moieties in $R^5$, —$OR^6$ and —$NR^6R^6$ are optionally substituted by 1 or 2 $R^9$ groups, and wherein the alkyl moieties of said optional substituents are optionally substituted by halo or $R^9$, with the proviso that two heteroatoms are not attached to the same carbon atom;

or each $R^1$ is independently selected from —$NHSO_2R^5$, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $R^{10}$—($C_2$-$C_4$)-alkanoylamino wherein $R^{10}$ is selected from halo, —$OR^6$, $C_2$-$C_4$ alkanoyloxy, —C(O)$R^7$, and —$NR^6R^6$; and wherein said —$NHSO_2R^5$, phthalimido-($C_1$-$C_4$-alkylsulfonylamino, benzamido, benzenesulfonylamino, 3-phenylureido, 2-oxopyrrolidin-1-yl, 2,5-dioxopyrrolidin-1-yl, and $R^{10}$—($C_2$-$C_4$)-alkanoylamino $R^1$ groups are optionally substituted by 1 or 2 substituents independently selected from halo, $C_1$-$C_4$ alkyl, cyano, methanesulfonyl and $C_1$-$C_4$ alkoxy;

or two $R^1$ groups are taken together with the carbons to which they are attached to form a 5-8 membered ring that includes 1 or 2 heteroatoms selected from O, S and N;

R² is hydrogen or C₁-C₆ alkyl optionally substituted by 1 to 3 substituents independently selected from halo, C₁-C₄ alkoxy, —NR⁶R⁶, and —SO₂R⁵;

n is 1 or 2 and each R³ is independently selected from hydrogen, halo, hydroxy, C₁-C₆ alkyl, —NR⁶R⁶, and C₁-C₄ alkoxy, wherein the alkyl moieties of said R³ groups are optionally substituted by 1 to 3 substituents independently selected from halo, C₁-C₄ alkoxy, —NR⁶R⁶, and —SO₂R; and, R⁴ is azido or -(ethynyl)-R¹¹ wherein R¹¹ is hydrogen or C₁-C₆ alkyl optionally substituted by hydroxy, —OR⁶, or —NR⁶R⁶.

18. The method of claim 17 wherein the EGFR inhibitor is a compound of formula I selected from the group consisting of:

(6,7-dimethoxyquinazolin-4-yl)-(3-ethynylphenyl)-amine; (6,7-dimethoxyquinazolin-4-yl)-[3-(3'-hydroxypropyn-1-yl)phenyl]-amine; [3-(2'-(aminomethyl)-ethynyl)phenyl]-(6,7-dimethoxyquinazolin-4-yl)-amine; (3-ethynylphenyl)-(6-nitroquinazolin-4-yl)-amine; (6,7-dimethoxyquinazolin-4-yl)-(4-ethynylphenyl)-amine; (6,7-dimethoxyquinazolin-4-yl)-(3-ethynyl-2-methylphenyl)-amine; (6-aminoquinazolin-4-yl)-(3-ethynylphenyl)-amine; (3-ethynylphenyl)-(6-methanesulfonylaminoquinazolin-4-yl)-amine; (3-ethynylphenyl)-(6,7-methylenedioxyquinazolin-4-yl)-amine; (6,7-dimethoxyquinazolin-4-yl)-(3-ethynyl-6-methylphenyl)-amine; (3-ethynylphenyl)-(7-nitroquinazolin-4-yl)-amine; (3-ethynylphenyl)-[6-(4'-toluenesulfonylamino)quinazolin-4-yl]-amine; (3-ethynylphenyl)-{6-[2'-phthalimido-eth-1'-yl-sulfonylamino]quinazolin-4-yl}-amine; (3-ethynylphenyl)-(6-guanidinoquinazolin-4-yl)-amine; (7-aminoquinazolin-4-yl)-(3-ethynylphenyl)-amine; (3-ethynylphenyl)-(7-methoxyquinazolin-4-yl)-amine; (6-carbomethoxyquinazolin-4-yl)-(3-ethynylphenyl)-amine; (7-carbomethoxyquinazolin-4-yl)-(3-ethynylphenyl)-amine; [6,7-bis(2-methoxyethoxy)quinazolin-4-yl]-(3-ethynylphenyl)-amine; (3-azidophenyl)-(6,7-dimethoxyquinazolin-4-yl)-amine; (3-azido-5-chlorophenyl)-(6,7-dimethoxyquinazolin-4-yl)-amine; (4-azidophenyl)-(6,7-dimethoxyquinazolin-4-yl)-amine; (3-ethynylphenyl)-(6-methansulfonyl-quinazolin-4-yl)-amine; (6-ethansulfanyl-quinazolin-4-yl)-(3-ethynylphenyl)-amine; (6,7-dimethoxy-quinazolin-4-yl)-(3-ethynyl-4-fluoro-phenyl)-amine; (6,7-dimethoxy-quinazolin-4-yl)-[3-(propyn-1'-yl)-phenyl]-amine; [6,7-bis-(2-methoxy-ethoxy)-quinazolin-4-yl]-(5-ethynyl-2-methyl-phenyl)-amine; [6,7-bis-(2-methoxy-ethoxy)-quinazolin-4-yl]-(3-ethynyl-4-fluoro-phenyl)-amine; [6,7-bis-(2-chloro-ethoxy)-quinazolin-4-yl]-(3-ethynyl-phenyl)-amine; [6-(2-chloro-ethoxy)-7-(2-methoxy-ethoxy)-quinazolin-4-yl]-(3-ethynyl-phenyl)-amine; [6,7-bis-(2-acetoxy-ethoxy)-quinazolin-4-yl]-(3-ethynyl-phenyl)-amine; 2-[4-(3-ethynyl-phenylamino)-7-(2-hydroxy-ethoxy)-quinazolin-6-yloxy]-ethanol; [6-(2-acetoxy-ethoxy)-7-(2-methoxy-ethoxy)-quinazolin-4-yl]-(3-ethynyl-phenyl)-amine; [7-(2-chloro-ethoxy)-6-(2-methoxy-ethoxy)-quinazolin-4-yl]-(3-ethynyl-phenyl)-amine; [7-(2-acetoxy-ethoxy)-6-(2-methoxy-ethoxy)-quinazolin-4-yl]-(3-ethynyl-phenyl)-amine; 2-[4-(3-ethynyl-phenylamino)-6-(2-hydroxy-ethoxy)-quinazolin-7-yloxy]-ethanol; 2-[4-(3-ethynyl-phenylamino)-7-(2-methoxy-ethoxy)-quinazolin-6-yloxy]-ethanol; 2-[4-(3-ethynyl-phenylamino)-6-(2-methoxy-ethoxy)-quinazolin-7-yloxy]-ethanol; [6-(2-acetoxy-ethoxy)-7-(2-methoxy-ethoxy)-quinazolin-4-yl]-(3-ethynyl-phenyl)-amine; (3-ethynyl-phenyl)-{6-(2-methoxy-ethoxy)-7-[2-(4-methyl-piperazin-1-yl)-ethoxy]-quinazolin-4-yl}-amine; (3-ethynyl-phenyl)-[7-(2-methoxy-ethoxy)-6-(2-morpholin-4-yl)-ethoxy)-quinazolin-4-yl]-amine; (6,7-diethoxyquinazolin-1-yl)-(3-ethynylphenyl)-amine; (6,7-dibutoxyquinazolin-1-yl)-(3-ethynylphenyl)-amine; (6,7-diisopropoxyquinazolin-1-yl)-(3-ethynylphenyl)-amine; (6,7-diethoxyquinazolin-1-yl)-(3-ethynyl-2-methyl-phenyl)-amine; [6,7-bis-(2-methoxy-ethoxy)-quinazolin-1-yl]-(3-ethynyl-2-methyl-phenyl)-amine; (3-ethynylphenyl)-[6-(2-hydroxy-ethoxy)-7-(2-methoxy-ethoxy)-quinazolin-1-yl]-amine; [6,7-bis-(2-hydroxy-ethoxy)-quinazolin-1-yl]-(3-ethynylphenyl)-amine; 2-[4-(3-ethynyl-phenylamino)-6-(2-methoxy-ethoxy)-quinazolin-7-yloxy]-ethanol; (6,7-dipropoxy-quinazolin-4-yl)-(3-ethynyl-phenyl)-amine; (6,7-diethoxy-quinazolin-4-yl)-(3-ethynyl-5-fluoro-phenyl)-amine; (6,7-diethoxy-quinazolin-4-yl)-(3-ethynyl-4-fluoro-phenyl)-amine; (6,7-diethoxy-quinazolin-4-yl)-(5-ethynyl-2-methyl-phenyl)-amine; (6,7-diethoxy-quinazolin-4-yl)-(3-ethynyl-4-methyl-phenyl)-amine; (6-aminomethyl-7-methoxy-quinazolin-4-yl)-(3-ethynyl-phenyl)-amine; (6-aminomethyl-7-methoxy-quinazolin-4-yl)-(3-ethynylphenyl)-amine; (6-aminocarbonylmethyl-7-methoxy-quinazolin-4-yl)-(3-ethynylphenyl)-amine; (6-aminocarbonylethyl-7-methoxy-quinazolin-4-yl)-(3-ethynylphenyl)-amine; (6-aminocarbonylmethyl-7-ethoxy-quinazolin-4-yl)-(3-ethynylphenyl)-amine; (6-aminocarbonylethyl-7-ethoxy-quinazolin-4-yl)-(3-ethynylphenyl)-amine; (6-aminocarbonylmethyl-7-isopropoxy-quinazolin-4-yl)-(3-ethynylphenyl)-amine; (6-aminocarbonylmethyl-7-propoxy-quinazolin-4-yl)-(3-ethynylphenyl)-amine; (6-aminocarbonylmethyl-7-methoxy-quinazolin-4-yl)-(3-ethynylphenyl)-amine; (6-aminocarbonylethyl-7-isopropoxy-quinazolin-4-yl)-(3-ethynylphenyl)-amine; and (6-aminocarbonylethyl-7-propoxy-quinazolin-4-yl)-(3-ethynylphenyl)-amine; (6,7-diethoxyquinazolin-1-yl)-(3-ethynylphenyl)-amine; (3-ethynylphenyl)-[6-(2-hydroxy-ethoxy)-7-(2-methoxy-ethoxy)-quinazolin-1-yl]-amine; [6,7-bis-(2-hydroxy-ethoxy)-quinazolin-1-yl]-(3-ethynylphenyl)-amine; [6,7-bis-(2-methoxy-ethoxy)-quinazolin-1-yl]-(3-ethynylphenyl)-amine; (6,7-dimethoxyquinazolin-1-yl)-(3-ethynylphenyl)-amine; (3-ethynylphenyl)-(6-methanesulfonylamino-quinazolin-1-yl)-amine; and (6-amino-quinazolin-1-yl)-(3-ethynylphenyl)-amine.

19. The method of claim 17 wherein the EGFR inhibitor of formula I is N-(3-ethynylphenyl)-6,7-bis(2-methoxyethoxy)-4-quinazolinamine.

20. The method of claim 19 wherein the EGFR inhibitor N-(3-ethynylphenyl)-6,7-bis(2-methoxyethoxy)-4-quinazolinamine is in HCl salt form.

21. The method of claim 20 wherein the EGFR inhibitor N-(3-ethynylphenyl)-6,7-bis(2-methoxyethoxy)-4-quinazolinamine is erlotinib, which is present in a substantially homogeneous crystalline polymorph form that exhibits an X-ray powder diffraction pattern having characteristic peaks expressed in degrees 2-theta at approximately 6.26, 12.48, 13.39, 16.96, 20.20, 21.10, 22.98, 24.46, 25.14 and 26.91.

22. The method of claim 1 wherein said EGFR inhibitor is an EGFR antibody.

23. The method of claim 1 wherein said EGFR inhibitor blocks the formation of EGFR-EGFR homodimers but not the formation of EGFR-HER2 heterodimers.

24. The method of claim 1 wherein the EGFR inhibitor blocks the formation of EGFR-EGFR homodimers and EGFR-HER2 heterodimers.

25. The method of claim 24 wherein said EGFR inhibitor is an EGFR antibody.

26. The method of claim 25 wherein said EGFR antibody is cetuximab.

27. The method of claim 1 comprising administering to said human subject an effective amount of pertuzumab and erlotinib.

28. The method of claim 27 wherein said pertuzumab and erlotinib exhibit a synergistic anti-tumor activity.

29. The method of claim 27 wherein said cancer is non-small cell lung cancer (NSCLC).

30. The method of claim 29 wherein said cancer is metastatic NSCLC.

31. The method of claim 30 wherein said cancer is poor-risk stage II or stage III NSCLC.

32. The method of claim 1 comprising administering to said patient an effective amount of pertuzumab and cetuximab.

33. The method of claim 32 wherein said pertuzumab and cetuximab exhibit a synergistic anti-tumor activity.

34. The method of claim 1 wherein said HER2 antibody and said EGFR inhibitor are administered simultaneously.

35. The method of claim 1 wherein said HER2 antibody and said EGFR inhibitor are administered consecutively.

36. The method of claim 1 further comprising treating said patient with at least one chemotherapeutic agents.

37. The method of claim 1 further comprising subjecting said patient to radiation therapy.

38. The method of claim 1 further comprising subjecting said patient to standard of care treatment.

39. A method for the treatment of cancer comprising administering to a human subject, an effective amount of a HER2 antibody which is a HER2-dimerization inhibitor and an EGFR inhibitor, wherein the subject's cancer is not driven solely by EGFR, and the cancer is non-small cell lung cancer (NSCLC) which is refractory to chemotherapy.

40. A method for the treatment of cancer comprising administering to a human subject an effective amount of pertuzumab and erlotinib, wherein the subject's cancer is not driven solely by EGFR, and the cancer is non-small cell lung cancer (NSCLC) which is refractory to chemotherapy.

41. A method for the treatment of EGFR and HER2 expressing lung cancer comprising administering to a human subject, an effective amount of a HER2 antibody which is a HER2-dimerization inhibitor and an EGFR inhibitor, wherein the subject's lung cancer is refractory or responds poorly to an EGFR inhibitor and is refractory to chemotherapy.

42. A method for the treatment of EGFR and HER2 expressing lung cancer comprising administering to a human subject, an effective amount of a HER2 antibody which is a HER2-dimerization inhibitor and an EGFR inhibitor, wherein the subject's lung cancer is refractory or responds poorly to a HER2 antibody and is refractory to chemotherapy.

43. A method of treating metastatic non-small cell lung cancer (NSCLC) in a patient comprising administering pertuzumab and erlotinib to a patient with NSCLC each in amounts effective to treat the NSCLC, wherein the treatment is provided as a second or third line therapy.

44. A method of treating metastatic non-small cell lung cancer (NSCLC) in a patient comprising administering pertuzumab and erlotinib to a patient with NSCLC each in amounts effective to treat the NSCLC, wherein the NSCLC is refractory to chemotherapy.

45. A method for the treatment of non-small cell lung cancer (NSCLC) comprising administering to a human subject with NSCLC expressing EGFR and HER2, an effective amount of a HER2 antibody which is a HER2-dimerization inhibitor and an EGFR inhibitor, wherein the EGFR inhibitor is erlotinib, which is present in a substantially homogeneous crystalline polymorph form that exhibits an X-ray powder diffraction pattern having characteristic peaks expressed in degrees 2-theta at approximately 6.26, 12.48, 13.39, 16.96, 20.20, 21.10, 22.98, 24.46, 25.14 and 26.91, and wherein the NSCLC does not show a complete response to treatment with said HER2 antibody or said EGFR inhibitor when administered as a single agent.

* * * * *

SEQUENCE LISTING

<160> NUMBER OF SEQ ID NOS: 66

<210> SEQ ID NO 1
<211> LENGTH: 195
<212> TYPE: PRT
<213> ORGANISM: Homo sapiens

<400> SEQUENCE: 1

```
Thr Gln Val Cys Thr Gly Thr Asp Met Lys Leu Arg Leu Pro Ala
 1               5                  10                  15

Ser Pro Glu Thr His Leu Asp Met Leu Arg His Leu Tyr Gln Gly
                20                  25                  30

Cys Gln Val Val Gln Gly Asn Leu Glu Leu Thr Tyr Leu Pro Thr
                35                  40                  45

Asn Ala Ser Leu Ser Phe Leu Gln Asp Ile Gln Glu Val Gln Gly
                50                  55                  60

Tyr Val Leu Ile Ala His Asn Gln Val Arg Gln Val Pro Leu Gln
                65                  70                  75

Arg Leu Arg Ile Val Arg Gly Thr Gln Leu Phe Glu Asp Asn Tyr
                80                  85                  90

Ala Leu Ala Val Leu Asp Asn Gly Asp Pro Leu Asn Asn Thr Thr
                95                  100                 105

Pro Val Thr Gly Ala Ser Pro Gly Gly Leu Arg Glu Leu Gln Leu
                110                 115                 120

Arg Ser Leu Thr Glu Ile Leu Lys Gly Gly Val Leu Ile Gln Arg
                125                 130                 135

Asn Pro Gln Leu Cys Tyr Gln Asp Thr Ile Leu Trp Lys Asp Ile
                140                 145                 150

Phe His Lys Asn Asn Gln Leu Ala Leu Thr Leu Ile Asp Thr Asn
                155                 160                 165

Arg Ser Arg Ala Cys His Pro Cys Ser Pro Met Cys Lys Gly Ser
                170                 175                 180

Arg Cys Trp Gly Glu Ser Ser Glu Asp Cys Gln Ser Leu Thr Arg
                185                 190                 195
```

<210> SEQ ID NO 2
<211> LENGTH: 124
<212> TYPE: PRT
<213> ORGANISM: Homo sapiens

<400> SEQUENCE: 2

```
Thr Val Cys Ala Gly Gly Cys Ala Arg Cys Lys Gly Pro Leu Pro
 1               5                  10                  15

Thr Asp Cys Cys His Glu Gln Cys Ala Ala Gly Cys Thr Gly Pro
                20                  25                  30

Lys His Ser Asp Cys Leu Ala Cys Leu His Phe Asn His Ser Gly
                35                  40                  45

Ile Cys Glu Leu His Cys Pro Ala Leu Val Thr Tyr Asn Thr Asp
                50                  55                  60

Thr Phe Glu Ser Met Pro Asn Pro Glu Gly Arg Tyr Thr Phe Gly
                65                  70                  75

Ala Ser Cys Val Thr Ala Cys Pro Tyr Asn Tyr Leu Ser Thr Asp
                80                  85                  90

Val Gly Ser Cys Thr Leu Val Cys Pro Leu His Asn Gln Glu Val
                95                  100                 105
```

```
Thr Ala Glu Asp Gly Thr Gln Arg Cys Glu Lys Cys Ser Lys Pro
            110                 115                 120

Cys Ala Arg Val

<210> SEQ ID NO 3
<211> LENGTH: 169
<212> TYPE: PRT
<213> ORGANISM: Homo sapiens

<400> SEQUENCE: 3

Cys Tyr Gly Leu Gly Met Glu His Leu Arg Glu Val Arg Ala Val
  1               5                  10                  15

Thr Ser Ala Asn Ile Gln Glu Phe Ala Gly Cys Lys Lys Ile Phe
             20                  25                  30

Gly Ser Leu Ala Phe Leu Pro Glu Ser Phe Asp Gly Asp Pro Ala
             35                  40                  45

Ser Asn Thr Ala Pro Leu Gln Pro Glu Gln Leu Gln Val Phe Glu
             50                  55                  60

Thr Leu Glu Glu Ile Thr Gly Tyr Leu Tyr Ile Ser Ala Trp Pro
 65                  70                  75

Asp Ser Leu Pro Asp Leu Ser Val Phe Gln Asn Leu Gln Val Ile
             80                  85                  90

Arg Gly Arg Ile Leu His Asn Gly Ala Tyr Ser Leu Thr Leu Gln
             95                 100                 105

Gly Leu Gly Ile Ser Trp Leu Gly Leu Arg Ser Leu Arg Glu Leu
            110                 115                 120

Gly Ser Gly Leu Ala Leu Ile His His Asn Thr His Leu Cys Phe
            125                 130                 135

Val His Thr Val Pro Trp Asp Gln Leu Phe Arg Asn Pro His Gln
            140                 145                 150

Ala Leu Leu His Thr Ala Asn Arg Pro Glu Asp Glu Cys Val Gly
            155                 160                 165

Glu Gly Leu Ala

<210> SEQ ID NO 4
<211> LENGTH: 142
<212> TYPE: PRT
<213> ORGANISM: Homo sapiens

<400> SEQUENCE: 4

Cys His Gln Leu Cys Ala Arg Gly His Cys Trp Gly Pro Gly Pro
  1               5                  10                  15

Thr Gln Cys Val Asn Cys Ser Gln Phe Leu Arg Gly Gln Glu Cys
             20                  25                  30

Val Glu Glu Cys Arg Val Leu Gln Gly Leu Pro Arg Glu Tyr Val
             35                  40                  45

Asn Ala Arg His Cys Leu Pro Cys His Pro Glu Cys Gln Pro Gln
             50                  55                  60

Asn Gly Ser Val Thr Cys Phe Gly Pro Glu Ala Asp Gln Cys Val
             65                  70                  75

Ala Cys Ala His Tyr Lys Asp Pro Pro Phe Cys Val Ala Arg Cys
             80                  85                  90

Pro Ser Gly Val Lys Pro Asp Leu Ser Tyr Met Pro Ile Trp Lys
             95                 100                 105

Phe Pro Asp Glu Glu Gly Ala Cys Gln Pro Cys Pro Ile Asn Cys
            110                 115                 120
```

```
Thr His Ser Cys Val Asp Leu Asp Asp Lys Gly Cys Pro Ala Glu
                125                 130                 135

Gln Arg Ala Ser Pro Leu Thr
                140
```

<210> SEQ ID NO 5
<211> LENGTH: 107
<212> TYPE: PRT
<213> ORGANISM: Mus musculus

<400> SEQUENCE: 5

```
Asp Thr Val Met Thr Gln Ser His Lys Ile Met Ser Thr Ser Val
  1               5                  10                  15

Gly Asp Arg Val Ser Ile Thr Cys Lys Ala Ser Gln Asp Val Ser
                 20                  25                  30

Ile Gly Val Ala Trp Tyr Gln Gln Arg Pro Gly Gln Ser Pro Lys
                 35                  40                  45

Leu Leu Ile Tyr Ser Ala Ser Tyr Arg Tyr Thr Gly Val Pro Asp
                 50                  55                  60

Arg Phe Thr Gly Ser Gly Ser Gly Thr Asp Phe Thr Phe Thr Ile
                 65                  70                  75

Ser Ser Val Gln Ala Glu Asp Leu Ala Val Tyr Tyr Cys Gln Gln
                 80                  85                  90

Tyr Tyr Ile Tyr Pro Tyr Thr Phe Gly Gly Gly Thr Lys Leu Glu
                 95                 100                 105

Ile Lys
```

<210> SEQ ID NO 6
<211> LENGTH: 119
<212> TYPE: PRT
<213> ORGANISM: Mus musculus

<400> SEQUENCE: 6

```
Glu Val Gln Leu Gln Gln Ser Gly Pro Glu Leu Val Lys Pro Gly
  1               5                  10                  15

Thr Ser Val Lys Ile Ser Cys Lys Ala Ser Gly Phe Thr Phe Thr
                 20                  25                  30

Asp Tyr Thr Met Asp Trp Val Lys Gln Ser His Gly Lys Ser Leu
                 35                  40                  45

Glu Trp Ile Gly Asp Val Asn Pro Asn Ser Gly Gly Ser Ile Tyr
                 50                  55                  60

Asn Gln Arg Phe Lys Gly Lys Ala Ser Leu Thr Val Asp Arg Ser
                 65                  70                  75

Ser Arg Ile Val Tyr Met Glu Leu Arg Ser Leu Thr Phe Glu Asp
                 80                  85                  90

Thr Ala Val Tyr Tyr Cys Ala Arg Asn Leu Gly Pro Ser Phe Tyr
                 95                 100                 105

Phe Asp Tyr Trp Gly Gln Gly Thr Thr Leu Thr Val Ser Ser
                110                 115
```

<210> SEQ ID NO 7
<211> LENGTH: 107
<212> TYPE: PRT
<213> ORGANISM: Artificial Sequence
<220> FEATURE:
<223> OTHER INFORMATION: Sequence is synthesized

<400> SEQUENCE: 7

```
Asp Ile Gln Met Thr Gln Ser Pro Ser Ser Leu Ser Ala Ser Val
```

```
            1               5                  10                 15
Gly Asp Arg Val Thr Ile Thr Cys Lys Ala Ser Gln Asp Val Ser
                    20                 25                 30

Ile Gly Val Ala Trp Tyr Gln Gln Lys Pro Gly Lys Ala Pro Lys
                    35                 40                 45

Leu Leu Ile Tyr Ser Ala Ser Tyr Arg Tyr Thr Gly Val Pro Ser
                    50                 55                 60

Arg Phe Ser Gly Ser Gly Ser Gly Thr Asp Phe Thr Leu Thr Ile
                    65                 70                 75

Ser Ser Leu Gln Pro Glu Asp Phe Ala Thr Tyr Tyr Cys Gln Gln
                    80                 85                 90

Tyr Tyr Ile Tyr Pro Tyr Thr Phe Gly Gln Gly Thr Lys Val Glu
                    95                 100                105

Ile Lys

<210> SEQ ID NO 8
<211> LENGTH: 119
<212> TYPE: PRT
<213> ORGANISM: Artificial Sequence
<220> FEATURE:
<223> OTHER INFORMATION: Sequence is synthesized

<400> SEQUENCE: 8

Glu Val Gln Leu Val Glu Ser Gly Gly Gly Leu Val Gln Pro Gly
  1               5                  10                 15

Gly Ser Leu Arg Leu Ser Cys Ala Ala Ser Gly Phe Thr Phe Thr
                    20                 25                 30

Asp Tyr Thr Met Asp Trp Val Arg Gln Ala Pro Gly Lys Gly Leu
                    35                 40                 45

Glu Trp Val Ala Asp Val Asn Pro Asn Ser Gly Gly Ser Ile Tyr
                    50                 55                 60

Asn Gln Arg Phe Lys Gly Arg Phe Thr Leu Ser Val Asp Arg Ser
                    65                 70                 75

Lys Asn Thr Leu Tyr Leu Gln Met Asn Ser Leu Arg Ala Glu Asp
                    80                 85                 90

Thr Ala Val Tyr Tyr Cys Ala Arg Asn Leu Gly Pro Ser Phe Tyr
                    95                 100                105

Phe Asp Tyr Trp Gly Gln Gly Thr Leu Val Thr Val Ser Ser
                    110                115

<210> SEQ ID NO 9
<211> LENGTH: 107
<212> TYPE: PRT
<213> ORGANISM: Artificial Sequence
<220> FEATURE:
<223> OTHER INFORMATION: Sequence is synthesized

<400> SEQUENCE: 9

Asp Ile Gln Met Thr Gln Ser Pro Ser Ser Leu Ser Ala Ser Val
  1               5                  10                 15

Gly Asp Arg Val Thr Ile Thr Cys Arg Ala Ser Gln Ser Ile Ser
                    20                 25                 30

Asn Tyr Leu Ala Trp Tyr Gln Gln Lys Pro Gly Lys Ala Pro Lys
                    35                 40                 45

Leu Leu Ile Tyr Ala Ala Ser Ser Leu Glu Ser Gly Val Pro Ser
                    50                 55                 60

Arg Phe Ser Gly Ser Gly Ser Gly Thr Asp Phe Thr Leu Thr Ile
                    65                 70                 75
```

Ser Ser Leu Gln Pro Glu Asp Phe Ala Thr Tyr Tyr Cys Gln Gln
            80                  85                  90

Tyr Asn Ser Leu Pro Trp Thr Phe Gly Gln Gly Thr Lys Val Glu
            95                  100                 105

Ile Lys

<210> SEQ ID NO 10
<211> LENGTH: 119
<212> TYPE: PRT
<213> ORGANISM: Artificial Sequence
<220> FEATURE:
<223> OTHER INFORMATION: Sequence is synthesized

<400> SEQUENCE: 10

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu
            35                  40                  45

Glu Trp Val Ala Val Ile Ser Gly Asp Gly Gly Ser Thr Tyr Tyr
            50                  55                  60

Ala Asp Ser Val Lys Gly Arg Phe Thr Ile Ser Arg Asp Asn Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Gly Arg Val Gly Tyr Ser Leu
            95                  100                 105

Tyr Asp Tyr Trp Gly Gln Gly Thr Leu Val Thr Val Ser Ser
            110                 115

<210> SEQ ID NO 11
<211> LENGTH: 214
<212> TYPE: PRT
<213> ORGANISM: Artificial sequence
<220> FEATURE:
<223> OTHER INFORMATION: Sequence is synthesized

<400> SEQUENCE: 11

Asp Ile Gln Met Thr Gln Ser Pro Ser Ser Leu Ser Ala Ser Val
1               5                   10                  15

Gly Asp Arg Val Thr Ile Thr Cys Lys Ala Ser Gln Asp Val Ser
            20                  25                  30

Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Tyr Ile Tyr Pro Tyr Thr Phe Gly Gln Gly Thr Lys Val Glu
            95                  100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

```
Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 12
<211> LENGTH: 448
<212> TYPE: PRT
<213> ORGANISM: Artificial sequence
<220> FEATURE:
<223> OTHER INFORMATION: Sequence is synthesized

<400> SEQUENCE: 12

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
            20                  25                  30

Asp Tyr Thr Met Asp Trp Val Arg Gln Ala Pro Gly Lys Gly Leu
            35                  40                  45

Glu Trp Val Ala Asp Val Asn Pro Asn Ser Gly Gly Ser Ile Tyr
            50                  55                  60

Asn Gln Arg Phe Lys Gly Arg Phe Thr Leu Ser Val Asp Arg Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Asn Leu Gly Pro Ser Phe Tyr
            95                 100                 105

Phe Asp Tyr Trp Gly Gln Gly Thr Leu Val Thr Val Ser Ser Ala
            110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly
            440                 445

<210> SEQ ID NO 13
<211> LENGTH: 217
<212> TYPE: PRT
<213> ORGANISM: Artificial sequence
<220> FEATURE:
<223> OTHER INFORMATION: Sequence is synthesized

<400> SEQUENCE: 13

Val His Ser Asp Ile Gln Met Thr Gln Ser Pro Ser Ser Leu Ser
  1               5                  10                  15

Ala Ser Val Gly Asp Arg Val Thr Ile Thr Cys Lys Ala Ser Gln
             20                  25                  30

Asp Val Ser Ile Gly Val Ala Trp Tyr Gln Gln Lys Pro Gly Lys
             35                  40                  45

Ala Pro Lys Leu Leu Ile Tyr Ser Ala Ser Tyr Arg Tyr Thr Gly
             50                  55                  60

Val Pro Ser Arg Phe Ser Gly Ser Gly Ser Gly Thr Asp Phe Thr
             65                  70                  75

Leu Thr Ile Ser Ser Leu Gln Pro Glu Asp Phe Ala Thr Tyr Tyr
             80                  85                  90

Cys Gln Gln Tyr Tyr Ile Tyr Pro Tyr Thr Phe Gly Gln Gly Thr
             95                 100                 105

Lys Val Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val
            125                 130                 135

Val Cys Leu Leu Asn Asn Phe Tyr Pro Arg Glu Ala Lys Val Gln
            140                 145                 150

Trp Lys Val Asp Asn Ala Leu Gln Ser Gly Asn Ser Gln Glu Ser
            155                 160                 165
```

-continued

Val Thr Glu Gln Asp Ser Lys Asp Ser Thr Tyr Ser Leu Ser Ser
            170                 175                 180

Thr Leu Thr Leu Ser Lys Ala Asp Tyr Glu Lys His Lys Val Tyr
            185                 190                 195

Ala Cys Glu Val Thr His Gln Gly Leu Ser Ser Pro Val Thr Lys
            200                 205                 210

Ser Phe Asn Arg Gly Glu Cys
            215

<210> SEQ ID NO 14
<211> LENGTH: 449
<212> TYPE: PRT
<213> ORGANISM: Artificial sequence
<220> FEATURE:
<223> OTHER INFORMATION: Sequence is synthesized

<400> SEQUENCE: 14

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Thr
             20                  25                  30

Asp Tyr Thr Met Asp Trp Val Arg Gln Ala Pro Gly Lys Gly Leu
             35                  40                  45

Glu Trp Val Ala Asp Val Asn Pro Asn Ser Gly Gly Ser Ile Tyr
             50                  55                  60

Asn Gln Arg Phe Lys Gly Arg Phe Thr Leu Ser Val Asp Arg Ser
             65                  70                  75

Lys Asn Thr Leu Tyr Leu Gln Met Asn Ser Leu Arg Ala Glu Asp
             80                  85                  90

Thr Ala Val Tyr Tyr Cys Ala Arg Asn Leu Gly Pro Ser Phe Tyr
             95                 100                 105

Phe Asp Tyr Trp Gly Gln Gly Thr Leu Val Thr Val Ser Ser Ala
            110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser

```
                    290                 295                 300
Thr Tyr Arg Val Val Ser Val Leu Thr Val Leu His Gln Asp Trp
                305                 310                 315
Leu Asn Gly Lys Glu Tyr Lys Cys Lys Val Ser Asn Lys Ala Leu
                320                 325                 330
Pro Ala Pro Ile Glu Lys Thr Ile Ser Lys Ala Lys Gly Gln Pro
                335                 340                 345
Arg Glu Pro Gln Val Tyr Thr Leu Pro Pro Ser Arg Glu Glu Met
                350                 355                 360
Thr Lys Asn Gln Val Ser Leu Thr Cys Leu Val Lys Gly Phe Tyr
                365                 370                 375
Pro Ser Asp Ile Ala Val Glu Trp Glu Ser Asn Gly Gln Pro Glu
                380                 385                 390
Asn Asn Tyr Lys Thr Thr Pro Pro Val Leu Asp Ser Asp Gly Ser
                395                 400                 405
Phe Phe Leu Tyr Ser Lys Leu Thr Val Asp Lys Ser Arg Trp Gln
                410                 415                 420
Gln Gly Asn Val Phe Ser Cys Ser Val Met His Glu Ala Leu His
                425                 430                 435
Asn His Tyr Thr Gln Lys Ser Leu Ser Leu Ser Pro Gly Lys
                440                 445

<210> SEQ ID NO 15
<211> LENGTH: 214
<212> TYPE: PRT
<213> ORGANISM: Artificial sequence
<220> FEATURE:
<223> OTHER INFORMATION: Sequence is synthesized

<400> SEQUENCE: 15

Asp Ile Gln Met Thr Gln Ser Pro Ser Ser Leu Ser Ala Ser Val
  1               5                  10                  15
Gly Asp Arg Val Thr Ile Thr Cys Arg Ala Ser Gln Asp Val Asn
                 20                  25                  30
Thr Ala Val Ala Trp Tyr Gln Gln Lys Pro Gly Lys Ala Pro Lys
                 35                  40                  45
Leu Leu Ile Tyr Ser Ala Ser Phe Leu Tyr Ser Gly Val Pro Ser
                 50                  55                  60
Arg Phe Ser Gly Ser Arg Ser Gly Thr Asp Phe Thr Leu Thr Ile
                 65                  70                  75
Ser Ser Leu Gln Pro Glu Asp Phe Ala Thr Tyr Tyr Cys Gln Gln
                 80                  85                  90
His Tyr Thr Thr Pro Pro Thr Phe Gly Gln Gly Thr Lys Val Glu
                 95                 100                 105
Ile Lys Arg Thr Val Ala Ala Pro Ser Val Phe Ile Phe Pro Pro
                110                 115                 120
Ser Asp Glu Gln Leu Lys Ser Gly Thr Ala Ser Val Val Cys Leu
                125                 130                 135
Leu Asn Asn Phe Tyr Pro Arg Glu Ala Lys Val Gln Trp Lys Val
                140                 145                 150
Asp Asn Ala Leu Gln Ser Gly Asn Ser Gln Glu Ser Val Thr Glu
                155                 160                 165
Gln Asp Ser Lys Asp Ser Thr Tyr Ser Leu Ser Ser Thr Leu Thr
                170                 175                 180
Leu Ser Lys Ala Asp Tyr Glu Lys His Lys Val Tyr Ala Cys Glu
                185                 190                 195
```

```
Val Thr His Gln Gly Leu Ser Ser Pro Val Thr Lys Ser Phe Asn
                200                 205                 210

Arg Gly Glu Cys
```

<210> SEQ ID NO 16
<211> LENGTH: 449
<212> TYPE: PRT
<213> ORGANISM: Artificial sequence
<220> FEATURE:
<223> OTHER INFORMATION: Sequence is synthesized

<400> SEQUENCE: 16

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
                 20                  25                  30

Asp Thr Tyr Ile His Trp Val Arg Gln Ala Pro Gly Lys Gly Leu
                 35                  40                  45

Glu Trp Val Ala Arg Ile Tyr Pro Thr Asn Gly Tyr Thr Arg Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ser Arg Trp Gly Gly Asp Gly Phe Tyr
                 95                 100                 105

Ala Met Asp Tyr Trp Gly Gln Gly Thr Leu Val Thr Val Ser Ser
                110                 115                 120

Ala Ser Thr Lys Gly Pro Ser Val Phe Pro Leu Ala Pro Ser Ser
                125                 130                 135

Lys Ser Thr Ser Gly Gly Thr Ala Ala Leu Gly Cys Leu Val Lys
                140                 145                 150

Asp Tyr Phe Pro Glu Pro Val Thr Val Ser Trp Asn Ser Gly Ala
                155                 160                 165

Leu Thr Ser Gly Val His Thr Phe Pro Ala Val Leu Gln Ser Ser
                170                 175                 180

Gly Leu Tyr Ser Leu Ser Ser Val Val Thr Val Pro Ser Ser Ser
                185                 190                 195

Leu Gly Thr Gln Thr Tyr Ile Cys Asn Val Asn His Lys Pro Ser
                200                 205                 210

Asn Thr Lys Val Asp Lys Lys Val Glu Pro Lys Ser Cys Asp Lys
                215                 220                 225

Thr His Thr Cys Pro Pro Cys Pro Ala Pro Glu Leu Leu Gly Gly
                230                 235                 240

Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp
                305                 310                 315

Trp Leu Asn Gly Lys Glu Tyr Lys Cys Lys Val Ser Asn Lys Ala
```

```
                        320                 325                 330
Leu Pro Ala Pro Ile Glu Lys Thr Ile Ser Lys Ala Lys Gly Gln
                    335                 340                 345

Pro Arg Glu Pro Gln Val Tyr Thr Leu Pro Pro Ser Arg Glu Glu
                350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
        380                 385                 390

Glu Asn Asn Tyr Lys Thr Thr Pro Pro Val Leu Asp Ser Asp Gly
    395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
                425                 430                 435

His Asn His Tyr Thr Gln Lys Ser Leu Ser Leu Ser Pro Gly
                    440                 445

<210> SEQ ID NO 17
<211> LENGTH: 10
<212> TYPE: PRT
<213> ORGANISM: Artificial Sequence
<220> FEATURE:
<223> OTHER INFORMATION: Humanized Antibody Sequence
<220> FEATURE:
<221> NAME/KEY: VARIANT
<222> LOCATION: 10
<223> OTHER INFORMATION: Xaa is preferably Asp or Ser

<400> SEQUENCE: 17

Gly Phe Thr Phe Thr Asp Tyr Thr Met Xaa
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Humanized Antibody Sequence

<400> SEQUENCE: 18

Asp Val Asn Pro Asn Ser Gly Gly Ser Ile Tyr Asn Gln Arg Phe Lys
1               5                   10                  15
Gly

<210> SEQ ID NO 19
<211> LENGTH: 10
<212> TYPE: PRT
<213> ORGANISM: Artificial Sequence
<220> FEATURE:
<223> OTHER INFORMATION: Humanized Antibody Sequence

<400> SEQUENCE: 19

Asn Leu Gly Pro Ser Phe Tyr Phe Asp Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Humanized Antibody Sequence

<400> SEQUENCE: 20
```

Lys Ala Ser Gln Asp Val Ser Ile Gly Val Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Humanized Antibody Sequence
<220> FEATURE:
<221> NAME/KEY: VARIANT
<222> LOCATION: 5
<223> OTHER INFORMATION: Xaa is preferably Arg or Leu
<220> FEATURE:
<221> NAME/KEY: VARIANT
<222> LOCATION: 6
<223> OTHER INFORMATION: Xaa is preferably Tyr or Glu
<220> FEATURE:
<221> NAME/KEY: VARIANT
<222> LOCATION: 7
<223> OTHER INFORMATION: Xaa is preferably Thr or Ser

<400> SEQUENCE: 21

Ser Ala Ser Tyr Xaa Xaa Xaa
1               5

<210> SEQ ID NO 22
<211> LENGTH: 9
<212> TYPE: PRT
<213> ORGANISM: Artificial Sequence
<220> FEATURE:
<223> OTHER INFORMATION: Humanized Antibody Sequence

<400> SEQUENCE: 22

Gln Gln Tyr Tyr Ile Tyr Pro Tyr Thr
1               5

<210> SEQ ID NO 23
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 23
tcctgtctat cacaatcagc ctctg                                         25

<210> SEQ ID NO 24
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 24
caaccccgag tatctcaaca ctgtc                                         25

<210> SEQ ID NO 25
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 25
gtgtcaacag cacattcgac agccc                                         25

<210> SEQ ID NO 26

```
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 26
aaattagcct ggacaaccct gacta                                              25

<210> SEQ ID NO 27
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 27
ctgactacca gcaggacttc tttcc                                              25

<210> SEQ ID NO 28
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 28
atggcatctt taagggctcc acagc                                              25

<210> SEQ ID NO 29
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 29
gcagaatacc taagggtcgc gccac                                              25

<210> SEQ ID NO 30
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 30
aaaatccaga ctctttcgat accca                                              25

<210> SEQ ID NO 31
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 31
cattagctct tagacccaca gactg                                              25

<210> SEQ ID NO 32
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 32
```

```
gttttgcaac gtttacaccg actag                                          25

<210> SEQ ID NO 33
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 33
tccacctcgg gcacattttg ggaag                                          25

<210> SEQ ID NO 34
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 34
gcaccttcaa agggacacct acggc                                          25

<210> SEQ ID NO 35
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 35
agtacctggg tctggacgtg ccagt                                          25

<210> SEQ ID NO 36
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 36
gccatgccag gaacctgtcc taagg                                          25

<210> SEQ ID NO 37
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 37
cctgcttgag ttcccagatg gctgg                                          25

<210> SEQ ID NO 38
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 38
gagtctttgt ggattctgag gccct                                          25

<210> SEQ ID NO 39
<211> LENGTH: 25
<212> TYPE: DNA
<213> ORGANISM: Artificial Sequence
<220> FEATURE:
```

```
<223> OTHER INFORMATION: Synthetic Oligonucleotide Probe

<400> SEQUENCE: 39
ggccctgccc aatgagactc taggg                                              25

<210> SEQ ID NO 40
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 40
gactctaggg tccagtggat gccac                                              25

<210> SEQ ID NO 41
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 41
ctttccttcc agatcctggg tactg                                              25

<210> SEQ ID NO 42
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 42
aagcgaccca ttcagagact gtccc                                              25

<210> SEQ ID NO 43
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 43
agactgtccc tgaaacctag tactg                                              25

<210> SEQ ID NO 44
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 44
ggtgtcagta tccaggcttt gtaca                                              25

<210> SEQ ID NO 45
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 45
cttatggtat gtagccagct gtgca                                              25

<210> SEQ ID NO 46
```

```
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 46
cttcttcaca ggcactcctg gagat                                              25

<210> SEQ ID NO 47
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 47
gaaggattac tctccatatc ccttc                                              25

<210> SEQ ID NO 48
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 48
ctctcaggct cttgactact tggaa                                              25

<210> SEQ ID NO 49
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 49
ggaactaggc tcttatgtgt gcctt                                              25

<210> SEQ ID NO 50
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 50
tttgtttccc atcagactgt caaga                                              25

<210> SEQ ID NO 51
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 51
tggtttatga ctcttaaccc cctag                                              25

<210> SEQ ID NO 52
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 52
``` ttaacccct agaaagacag aagct                                            25

<210> SEQ ID NO 53
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 53
tcagcactta actatgagcc aggca                                           25

<210> SEQ ID NO 54
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 54
catcatacta aacttcacct acatt                                           25

<210> SEQ ID NO 55
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 55
taaacttcac ctacattatc tcact                                           25

<210> SEQ ID NO 56
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 56
gagacagttc tctgtggttc aggaa                                           25

<210> SEQ ID NO 57
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 57
gatactttca ggggtggccc aatga                                           25

<210> SEQ ID NO 58
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 58
gaaacacact ggattgggta tgtct                                           25

<210> SEQ ID NO 59
<211> LENGTH: 25
<212> TYPE: DNA
<213> ORGANISM: Artificial Sequence
<220> FEATURE:

<223> OTHER INFORMATION: Synthetic Oligonucleotide Probe

<400> SEQUENCE: 59
gggtatgtct acctggcaga tactc                                   25

<210> SEQ ID NO 60
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 60
ggaaccttgc aacggtatcc aggga                                   25

<210> SEQ ID NO 61
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 61
gggactatga tgagaggcca gcaca                                   25

<210> SEQ ID NO 62
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 62
gaggccagca cattatcttc atatg                                   25

<210> SEQ ID NO 63
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 63
tcttcatatg tcacctttgc tacgc                                   25

<210> SEQ ID NO 64
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 64
aatttgttca gttcgtatac ttcgt                                   25

<210> SEQ ID NO 65
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 65
gtagaaggta actctttgca cataa                                   25

<210> SEQ ID NO 66

```
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 66
gcttagggat aggtccttgg gtcaa                                          25
```